US009441237B2

(12) United States Patent (10) Patent No.: US 9,441,237 B2
Ozga et al. (45) Date of Patent: Sep. 13, 2016

(54) AUXIN RECEPTORS

(75) Inventors: Jocelyn Ozga, Edmonton (CA); Dennis Reinecke, Edmonton (CA); Courtney Nadeau, Vienna (AT)

(73) Assignee: THE GOVERNORS OF THE UNIVERSITY OF ALBERTA, Edmonton, Alberta (CA)

( * ) Notice: Subject to any disclaimer, the term of this patent is extended or adjusted under 35 U.S.C. 154(b) by 432 days.

(21) Appl. No.: 12/875,814

(22) Filed: Sep. 3, 2010

(65) Prior Publication Data

US 2012/0060236 A1 Mar. 8, 2012

(51) Int. Cl.
*C12N 15/82* (2006.01)
*C12N 15/00* (2006.01)
*C12N 5/04* (2006.01)
*A01H 5/00* (2006.01)
*C07K 14/415* (2006.01)

(52) U.S. Cl.
CPC ......... *C12N 15/8271* (2013.01); *C07K 14/415* (2013.01)

(58) Field of Classification Search
USPC ....................................................... 800/283
See application file for complete search history.

(56) References Cited

PUBLICATIONS

Dharmasiri N. et al., Develop. Cell (2005) 9:109-119.*
Parry G. et. al, Proc. Natl. Acad. Sci (2009) 106:22540-22545.*
Colliver et al, Differential modification' of flavonoid and isoflavonoid biosynthesis with an antisense chalcone synthase construct in transgenic Lotus corniculatus, Plant Mol. Biol. (1997) 35:509-599.*
Senthil-Kumar et al, A systematic study to determine the extent of gene silencing in Nicotiana benthamiana and other Solanaceae species when heterologous gene sequences are used for virus-induced gene silencing New Phytologist (2007) 176: 782-791.*
Bandurski, Robert S. et al.; Concentration of Indole-3-acetic Acid and Its Derivatives in Plants; Plant Physiol.; 1977; vol. 60; pp. 211-213; Michigan, USA.
Bandurski, Robert S. et al.; Hormone Biosynthesis and Metabolism; Plant Hormones; 1995; pp. 39-65; Kluwer Academic Publishers; Netherlands.
Bartel, Bonnie; Auxin Biosynthesis; Plant Physiol. Plant Mol. Biol.; 1997; vol. 48; pp. 51-66; Annual Reviews Inc.
Bialek, Krystyna et al.; Quantitation of Indoleacetic Acid Conjugates in Bean Seeds by Direct Tissue Hydrolysis; Plant Physiol.; 1989; vol. 90; pp. 398-400.
Cannon, Steven B. et al.; Legume Genome Evolution Viewed Through the Medicago Truncatula and Lotus Japonicus Genomes; PNAS; Oct. 3, 2006; vol. 13, No. 40; pp. 14959-14964; The National Academy for Sciences, USA.
Davidson, Sandra E. et al.; The Pea Gene NA Encodes ent-Kaurenoic Acid Oxidase; Plant Physiology; Jan. 2003; vol. 131; pp. 335-344; American Society of Plant Biologists.
Davies, D. Roy; Studies of Seed Development in Pisum sativum, I. Seed Size in Reciprocal Crosses; Planta (Berl); 1975; vol. 124; pp. 297-302; Springer-Verlag; Norwich, United Kingdom.

Dharmasiri, Nihal et al.; Auxin Signaling and Regulated Protein Degradation; Trends in Plant Science; Science Direct; Jun. 2004; vol. 9, No. 6; pp. 302-308; Elsevier Ltd.; Indiana, USA.
Dharmasisi, Nihal et al.; The F-Box Protein TIRI is an Auxin Receptor; Nature; May 2005; vol. 435, No. 26; pp. 441-445; Nature Publishing Group; Indiana, USA.
Dharmasiri, Nihal et al.; Plant Development Is Regulated by a Family of Auxin Receptor F Box Proteins; Developmental Cell; Jul. 2005; vol. 9; pp. 109-119; Elsevier Inc.; Indiana, USA.
Gagne, Jennifer M. et al.; The F-box Subunit of the SCF E3 Complex is Encoded by a Diverse Superfamily of Genes in Arabidopsis; PNAS; Aug. 20, 2002; vol. 99, No. 17; pp. 11519-11524;.
Gray, William M. et al.; Identification of an SCF Ubiquitin-Ligase Complex Required for Auxin Response in Arabidopsis Thaliana; Genes & Developments; 1999; vol. 13; pp. 1678-1691; Cold Spring Harbor Laboratory Press; New York, USA.
Gray, William M. et al.; Auxin Regulates SCF TIR1-dependent Degradation of AUX/IAA Proteins; Nature; Nov. 15, 2001; vol. 414; pp. 271-276; Macmillan Magazines Ltd.; Australia.
Hagen, Gretchen et al.; Auxin-Receptors Gene Expression: Genes, Promoters and Regulatory Factors; Plant Molecular Biology; 2002; vol. 49; pp. 373-385; Kluwer Academic Publishers; Netherlands.
Jacobsen, John V. et al; Abscisic Acid, Phaseic Acid and Gibberellin Contents Associated With Dormancy and Germination in Barley; Physiol. Plant.; 2002; vol. 115; pp. 428-441; Physiologia Plantarum; Denmark.
Jakubowska, Anna et al.; The Auxin Conjugate 1-O-indole-3-acetyl-B-D-glucose is Synthesized in Immature Legume Seeds by IAGLc Synthase and May be Used for Modification of Some High Molecular Weight Compounds; Journal of Experimental Botany; Apr. 2004; vol. 55, No. 398; pp. 791-801; Society for Experimental Botany.
Jenik, Pablo D. et al.; Embryonic Patterning in Arabidopsis Thaliana; Annu. Rev. Cell Dev. Biol.; 2007; vol. 23; pp. 207-236; Annual Reviews; Georgia, USA.
Johnstone, Marilyn M.G. et al.; The Auxins IAA and 4Cl-IAA Differentially Modify Gibberellin Action via Ethylene Response in Developing Pea Fruit; K. Plant Growth Regul; 2005; vol. 24; pp. 214-225; Springer Science-Business Medica, Inc.
Kapoor, B.M.; Contributions to the Cytology of Endosperm in Angiosperms—XII. Pisum Satvum L.; Genetica; 1966; vol. 37; pp. 557-568; Delhi, India.
Katayama, Masato et al.; Identification of 4-Chloroindole-3-acetic Acid and Its Methyl Ester in Immature Seeds of Vicia amurensis (the Tribe Vicieae), and Their Absence from Three Species of Phaseoleae; Plant Cell Physiol.; 1987; vol. 28, No. 2; pp. 383-386; JSPP.
Katayama, Masato et al.; Localization of 4-Chloroindole-3-acetic Acid in Seeds of Pisum sativum and Its Absence from All Other Organs; Plant Cell Physiol.; 1988; vol. 29, No. 5; pp. 889-891; JSPP.
Kepinski, Stefan et al.; The Arabidopsis F-box Protein TIR1 is an Auxin Receptor; Nature; May 2005; vol. 435; pp. 446-451; Nature Publishing Group; Sweden.
Koshioka, Masaji et al.; Purification and Separation of Plant Gibberellins from Their Precursors and Glucosyl Conjugates; Plant Physiol.; 1983; vol. 73; pp. 398-406; Waters Scientific Ltd.; Mississauga, Ontario, Canada.

(Continued)

*Primary Examiner* — Mykola Kovalenko
(74) *Attorney, Agent, or Firm* — Foley & Lardner LLP

(57) ABSTRACT

The invention is directed to isolated polynucleotide and polypeptides of the PsAFB2 and PsAFB6 genes from *Pisum sativum*; nucleic acid constructs, vectors and host cells incorporating the polynucleotide sequences; and methods of producing and using same. Also provided are transformed cells, and transgenic seeds and plants with enhanced abiotic stress tolerance.

5 Claims, 16 Drawing Sheets

(56) References Cited

PUBLICATIONS

Letunic, Ivica et al.; Smart 5: Domains in the Context of Genomes and Networks; Nuclein Acids Research; 2006; vol. 34; Database Issue pp. D257-D260; Oxford University Press.

Leyser, Ottoline; Molecular Genetics of Auxin Signaling; Annu. Rev. Plant Biol.; 2002; vol. 53; pp. 377-398; Annual Reviews.

Livak, Kenneth J. et al.; Analysis of Relative Gene Expression Data Using Real-Time Quantitative PCR and the 2 Method; Methods; 2001; vol. 25; pp. 402-408; Elsevier Science, USA.

Lur, Huu-Sheng et al.; Role of Auxin in Maize Endosperm Development, Timing of Nuclear DNA Endoreduplication, Zein Expression, and Cytokinin; Plant Physiol.; 1993; vol. 103; pp. 273-280.

Magnus, Volker et al.; 4-Chloroindole-3-Acetic and Indole-3-Acetic Acids in Pisum Sativum; Phytochemistry; vol. 46, No. 4; pp. 675-681; Elsevier Science Ltd.; Great Britain, United Kingdom.

Marumo, Shingo et al.; Isolation of D-4-Chlorotryptophane Derivatives as Auxin-Related Metabolites from Immature Seens of Pisum Sativum; Planta (Berl.); 1970; vol. 90; pp. 208-211.

Nordstrom, Ann-Caroline et al.; Effect of Exogenous Indole-3-Acetic Acid and Indole-3-Butyric Acid on Internal Levels of the Respective Auxins and Their Conjugation with Aspartic Acid During Adventitious Root Formation in Pea Cuttings; Plant Physiol.; 1991; vol. 96; pp. 856-861.

Orzaez, D. et al.; Programme of Senescence in Petals and Carpels of *Pisum Satvum* L. Flowers and Its Control by Ethylene; Planta; 1999; vol. 208; pp. 220-226; Springer-Verlag.

Ozga, Jocelyn A. et al.; Developmental and Hormonal Regulation of Gibberellin Biosynthesis and Catabolism in Pea Fruit 1[OA]; Plant Physiology; May 2009; vol. 150; pp. 448-462; American Society of Plant Biologists; USA.

Ozga, Jocelyn A. et al.; Interaction of 4-Chloroindole-3-Acetic Acid and Gibberellins in Early Pea Fruit Development; Plant Growth Regulation; 1999; vol. 27; pp. 33-38; Kluwer Academic Publishers; Netherlands.

Ozga, Jocelyn A. et al.; Seed Effects on Gibberellin Metabolism in Pea Pericarp 1,2; Plant Physiol.; 1992; vol. 100; pp. 88-97.

Ozga, Jocelyn A. et al.; Pollimation-, Development-, and Auxin-Specific Regulation of Gibberellin 3B-Hydrozylase Gene Expression in Pea Fruit and Seeds; Plant Physiology; Mar. 2003; vol. 131; pp. 1137-1146; American Society of Plant Biologists; USA.

Park, Jin-Young et al.; Mutation in Domain II of IAA1 Confers Diverse Auxin-Related Phenotypes and Represses Auxin-Activated Expression of Aux/IAA Genes in Steroid Regulator-Inducible System; The Plant Journal; 2002; vol. 32; pp. 669-683; Blackwell Publishing Ltd.

Patterson, Sara E.; Update on Abscission and Dehiscence in Arabidopsis, Cutting Loose. Abscission and Dehiscence in Arabidopsis; Plant Physiology; Jun. 2001; vol. 126; pp. 494-500; American Society of Plant Physiologists.

Reid, James B. et al.; A Mutant-Based Approach, Using Pisum Sativum, to Understanding Plant Growth; Chicago Journals; Int. J. Plant Sci.; 1993; vol. 154, No. 1; pp. 22-34; University of Chicago.

Reinecke, Dennis M. et al.; Effect of Halogen Substitution of Indole-3-Acetic Acid on Biological Activity in Pea Fruit; Pergamon; Phytochemistry; 1995; vol. 40, No. 5; pp. 1361-1366; Elsevier Science Ltd.; Great Britain, United Kingdom.

Reinecke, Dennis M. et al.; Molecular Properties of 4-Substituted Indole-3-Acetic Acids Affecting Pea Pericarp Elongation; Plant growth Regulation; 1999; vol. 27; pp. 39-48; Kluwer Academic Publishers; Netherlands.

Rose, Timothy M. et al.; CODEHOP (COnsensis-DEgenerate Hybrid Oligonucleotide Primer) PCR Primer Design; Nucleaic Acids Research; 2003; vol. 31, No. 13; pp. 3763-3766; Oxford University Press.

Schneider, Elnora A. et al.; Gas Chromatography-Mass Spectrometry Evidence for Several Endogenous Auxins in Pea Seedling Organs; Planta; 1985; vol. 165; pp. 232-241; Springer-Verlag.

Schultz, Jorg et al.; Smart, a Simple Modular Architecture Research Tool: Identification of Signaling Domains; Proc. Natl. Acad. Sci. USA; May 1998; vol. 95; pp. 5857-5864; The National Academy of Sciences.

TABm Xu et al.; Mechanism of Auxin Perception by the TIR1 Ubiquitin Ligase; Nature; Apr. 2007; vol. 446; pp. 640-645; Nature Publishing Group.

Tiwari, Shiv B. et al.; AUX/IAA Proteins Are Active Repressors, and Their Stability and Activity Are Modulated by Auxin; The Plant Cell; Dec. 2001; vol. 13; pp. 2309-2822; American Society of Plant Biologists; USA.

Triques, Karine et al.; Characterization of Arabidopsis Thaliana Mismatch Specific Endonucleases: Application to Mutation Discovery by TILLING in Pea; The Plant Journal; 2007; vol. 51; pp. 1116-1125; The Authors Journal Compilation; Blackwell Publishing Ltd.

Ulmasov, Tim et al.; Composite Structure of Auxin Response Elements; The Plant Cell; vol. 7; pp. 1611-1623; American Society of Plant Physiologists; USA.

Ulmasov, Tim et al.; Dimerization of DNA Binding of Auxin Response Factors; The Plant Journal; 1999; vol. 19, No. 3; pp. 309-319; Blackwell Science Ltd.; USA.

Van Huizen, Rika et al.; Seed and 4-Chloroindole-3-Acetic Acid Regulation of Giberellin Metabolism in Pea Pericarp; Plant Physiol.; 1995; vol. 109; pp. 1213-1217.

Van Huizen, Rika et al.; Seed and Hormonal Regulation of Gibberellin 20-Oxidase Expression in Pea Pericarp; Plant Physiol. 1997; vol. 115; pp. 123-128.

Woodward, Andrew W. et al.; Auxin: Regulation, Action, and Interaction; Annals of Botany Company; 2005; vol. 95; pp. 707-735; Oxford University Press.

Ozga, J. et al.; The Effect of 4-CL-IAA on Growth and GA Metabolism in Deseeded Pea Pericarp; Plant Physiol.; 1992; vol. 99: S-12.

Yang et al., "Overexpression of *ZmAFB2*, the maize homologue of *AFB2* gene, enhances salt tolerance in transgenic tobacco," Plant Cell Tiss. Organ Cult., vol. 112, pp. 171-179, 2013.

\* cited by examiner

FIG. 6A

PsAFB2 cDNA Sequence

```
   1- ATGAATTATT TTCCAGACGA GGTAATAGAA CATGTGTTTG ACTATGTGGT GTCACATAGC
              ---------------------------F-BOX-------------------

61- GACAGAAACA GTTTGTCTTT GGTATGCAAA AGTTGGTATA GAATAGAGGG ATTTACAAGG
      ------------------F-BOX--------------------------------------

121- AAAAGGGTGT TCATAGGAAA CTGTTACTCT ATTAGTCCTG AGAGGTTGGT AGAGAGGTTT
      ------F-BOX-----

181- CCTGATTTCA AATCTTTAAC TCTAAAGGGA AAACCTCATT TTGCTGACTT CAGTTTGGTT

241- CCTCATGGTT GGGGTGGTTT TGTTTATCCA TGGATTGAAG CTCTTGCTAA GAGTAGAGTT
                                                              --LRR-

301- GGGTTGGAGG AGCTTAGGTT GAAGAGGATG GTTGTGTCAG ATGAGAGCCT GGAGCTACTG
      ---------------------------LRR------------------------------

361- TCTCGTTCTT TCATGAATTT TAAGTCTTTA GTTCTTGTTA GCTGTGAAGG GTTCACCACT
      --------------------------LRR----------------------------

421- GATGGACTTG CTGCTGTAGC TGCAAATTGC AGGTCTCTTA GGGAGCTAGA TTTGCAAGAG
      --------LRR------------------

481- AATGAAGTTG AAGATCACAA AGGACAGTGG CTAAGTTGTT TTCCGGAAAA CTGTACATCA

541- CTCGTCGCTC TTAATTTTGC TTGCCTTAAA GGAGAGATTA ACGTGGGAGC ACTTGAGAGA

601- CTTGTGGCAA GATCACCTAA CCTCAAGACT CTAAGGTTAA ACCGTTCCGT GCCGGCTGAT

661- GCACTTCAAA GGATACTAAT GCGAGCGCCT CAAATAGCAG ATTTGGGTAT TGGATCATTT

721- ATCCATGATC TCAATTCAGA GGCCTACATA AAGCTTAAGA ATACCATTCT TAGATGCCGG

781- TCAATAACGA GTTTGTCCGG ATTTTTGGAA GTGGCTCCTT TTAGCCTTGC TGCTGTGTAT

841- CCAATTTGCC GGAACTTAAC ATCCTTGAAC TTGAGCTATG CAGCAAGCAT TCAGGGCGCT
                                 ---------------------LRR----------------------------

901- GAGCTTATTA AACTTATTCG CCATTGCGGC AAACTACAGC GCTTATGGAT AATGGATTGC
      ---------------------------LRR------------------------------

961- ATTGGAGACA AAGGACTAGT TGCTGTAGCT ACTATATGTA AAGAGTTGCA AGAATTGAGG
      ---------------------------LRR------------------------------

1021- GTATTTCCAT CGGCACCATT TGGAAATCAA GCAGCTGTTA CCGAAGTAGG ACTTGTTGCG
      ---------------------------LRR------------------------------

1081- ATATCAAAGG GATGCCCAAA GCTCCACTCG TTACTCTACT TCTGCCACCA GATGACAAAT
      ---------------------------LRR------------------------------

1141- GCTGCTCTCA TAACAGTAGC CAAGAACTGT CCAAATTTTA TCCGATTTAG GTTATGCATC
      ------------LRR--------------
```

FIG. 6B

```
      ----FWD Validation--->

1201- CTCGATGCAA CAAAACCTGA CTCCGACACA ATGCAGCCAC TGGATGAAGG TTTTGGGGCA
      ------FWD Primer------>              -----Probe-----

1261- ATCGTACAGT CATGCAAACG ACTGAGGCGG CTATCACTCT CCGGTCAGTT GACCGACCAG
                     ---------------LRR-----------------------------
      <------REV Primer------             <----REV Validation---

1321- GTCTTCCTTT ACATTGGAAT GTACGCGGAG CAGCTTGAAA TGCTATCTAT TGCTTTTGCT
      ----------LRR-------------

1381- GGCGAGAGTG ACAAGGGAAT GCTCTATGTA TTGAATGGTT GCAAAAAGCT TCGCAAGCTC
                                             -----------LRR---------

1441- GAGATAAGAG ACTGCCCTTT CGGCGACACA GCACTTCTGA CAGACGTAGG AAGTATGAA
      --------------------------------LRR-----------------------------

1501- ACAATGCGAT CCCTTTGGAT GTCGTCGTGT GAGGTGACTG TAGGAGCATG CAAGACATTG

1561- GCGAAGAAGA TGCCGAGTTT GAATGTGGAG ATCTTCAATG AAAGTGAACA AGCAGATTGT

1621- TATGTGGAAG ATGGGCAAAG AGTGGAGAAG ATGTATTTGT ATCGTTCTGT GGCTGGTAAA

1681- AGGGAAGATG CACCAGACTA TGTATGGACT CTGTAG
```

FIG. 7A
*PsAFB6A* cDNA Sequence

```
   1- ATGGAACCAC AAACCATGAA TCCCAGTTCA GTCTTTCCAG ATGAAGTGCT GGAGAGAATT
                         ----------------F-BOX--------------------

61- CTCAGCATGG TGAAGTCACG CAAAGACAAG AGTTCGGTTT CATTGGTTTG CAAAGACTGG

121- TTCGACGCTG AAAGATGGTC GAGAAAGAAT GTGTTCATAG GTAACTGTTA TTCCGTTACA

181- CCAGAGATCT TGACTCAAAG ATTTCCGAAT GTTCGAAGTG TTACATTGAA AGGGAAGCCA

241- CGTTTCTCTG ATTTCAACTT GGTTCCTGCT AATTGGGGTG CTGATATTCA TCCATGGCTT

301- GTTGTTTTCG CTGAAAAGTA CCCTTTTCTT GAAGAGTTAA GGCTTAAGAG AATGGTTGTT
                         --------------------LRR---------------------

361- ACTGATGAGA GTTTAGAGTT TCTGGCTTTT TCGTTTCCGA ATTTTAAAGC TCTTTCTCTT
                         ---------------------LRR---------------------

421- TTGAGCTGTG ATGGATTTAG CACTGATGGT TTAGCTGCTG TTGCTACTAA TTGCAAGAAC
                         -------------LRR-----------------------------

481- TTAACTGAGC TTGACATACA AGAGAATGGT ATCGAAGACA AAGCGGTAA CTGGTTGAGT

541- TGCTTCCCAG AAAGCTTTAC ATCATTGGAA GTGTTGAACT TTGCCAACCT AACCAATGAA

601- GTAAACATCG ACGCGCTAGA GAAACTGTT GGTAGGTGCA AATCATTGAA GACTTTGAAG

661- GTTAACAAAA GCGTAACGCT GGAACAGTTG AAAAAACTTC TTGTTCGCGC CCCTCAGTTA

721- TGTGAGCTTG GCAGTGGCTC ATTTTCGCAA GAGCTGACAT CTCAGCAGTA TGCAGAGCTC

781- GAAACCGCGT TCAAAAATTG TAAAAGCCTT CACACCCTGT CTGGTTTATG GGTGGCTTCA

841- GCGCGATATC TTCAAGTTCT ATACCCTGCG TGCGCGAATC TGACTTTTTT GAATTTTAGC

901- TATGCTCCTC TTGACAGTGA AGATCTTACC AAGATTCTTG TTCACTGTCC TAATCTTCGA
                                                    ------LRR-------

961- CGTCTTTGGG TTGTTGACAC CGTTGAAGAC AAGGGACTTG AAGCGGTTGG ATCGAACTGT
                         -------------------LRR-----------------------

1021- CCATTGCTTG AGGAACTGCG TGTTTTTCCT GCAGATCCGT TGACGAGGA AGCTGAAGGC

1081- GGGGTGACTG AATCGGGGTT TGTTGCTGTC TCTGAAGGAT GCCGGAAGCT TCACTATGTT
                                                           ---------LRR------

1141- CTCTACTTTT GTCGTCAAAT GACCAATGCT GCTGTCGCTA CCGTAGTCCA AAACTGCCCC
                         ----------------------LRR---------------------
                         ----FWD Validation----> ------FWD Primer-----> --Probe 1201- GACTTTACTC ATTTCCGCCT CTGCATAATG AACCCTGGCC AGCAAGATTA CCTGACGGAC
      Probe-- <---REV Primer-----                          <----REV Validation
```

FIG. 7B

1261- GAACCTATGG ACGAGGCCTT CGGAGAAGTT GTTAAGAACT GCACTAAACT TCAGAGGCTC
                                                          ---------------LRR------

1321- GCTGTATCAG GTTATCTAAC GGACCTCACA TTCGAGTATA TAGGAAAGTA TGCCAAAAAC
      ------------------------------LRR----------------------

1381- TTGGAAACGC TTTCGGTGGC TTTTGCAGGA AGCAGTGATT GGGGAATGGA GTGTGTACTG

1441- GTCGGATGTC CGAAACTGAG AAAACTCGAG ATAAGAGACA GTCCATTCGG AAATGCAGCG
                    ------------------------------------LRR------------------

1501- CTTTTGGCAG GTTGGAGAA GTACGAGTCG ATGAGGTCAC TTTGGATGTC GTCCTGCAGA
            -------------LRR-------

1561- CTGACGATGA ATGGATGTAG ATTTTTGGCA GGAGAAAAGC CGAGGTTGAA TGTCGAAGTA

1621- ATGCAGGAAG AAGGAGGCGA TGATAGTCGG GCCGAAAAAC TTTATGTTTA TCGATCTGTT

1681- GCCGGGCCAA GAAGGGATGC ACCTCCTTTT GTTCTCACTC TCTGA

FIG. 13A
Alignment of AFB2/3 Proteins

```
              ....|....| ....|....| ....|....| ....|....| ....|....|
                       10         20         30         40         50
PsAFB2        -------MNY FPDEVIEHVF DYVVSHSDRN SLSLVCKSWY RIEGFTRKRV
AtAFB2        -------MNY FPDEVIEHVF DFVTSHKDRN AISLVCKSWY KIERYSRQKV
AtAFB3        -------MNY FPDEVIEHVF DFVASHKDRN SISLVCKSWH KIERFSRKEV
PtrAFB2A      -------MNY FPDEVLEHIF DFVTSQRDRN SVSQVCKPWY KIESSSRQKV
PtrAFB2B      -------MNY FPDEVLEHIF DFVTSQRDRN SVSQVCKPWY KIESTSRQKV
MtAFB2        -------MNY FPDEVIEHVF DYVVSHSDRN SLSLVCKSWY RIERFTRQRV
OsAFB2A       -------MTY FPEEVVEHIF SFLPAQRDRN TVSLVCKVWY EIERLSRRGV
OsAFB2B       -------MVF FPEEVVEHIL GFLASHRDRN AVSLVCREWY RVERLSRRSV

....|....| ....|....| ....|....| ....|....| ....|....|
                       60         70         80         90        100
PsAFB2        FIGNCYSISP ERLVERFPDF KSLTLKGKPH FADFSLVPHG WGGFVYPWIE
AtAFB2        FIGNCYAINP ERLLRRFPCL KSLTLKGKPH FADFNLVPHE WGGFVLPWIE
AtAFB3        FIGNCYAINP ERLIRRFPCL KSLTLKGKPH FADFNLVPHE WGGFVHPWIE
PtrAFB2A      FVGNCYAISP QRVIERFPGL KSITLKGKPH FADFNLVPND WGGFVYPWIE
PtrAFB2B      FVGNCYAISP ERVIERFPGL KSITLKGKPH FADFNLVPHD WGGFVYPWIE
MtAFB2        FIGNCYSISP ERLVERFPDL KSLTLKGKPH FADFSLVPHG WGGFVYPWIE
OsAFB2A       FVGNCYAVRA GRVAARFPNV RALTVKGKPH FADFNLVPPD WGGYAGPWIE
OsAFB2B       LVRNCYAARP ERVHARFPGL RSLSVKGRPR F-----VPAG WGAAARPWVA

....|....| ....|....| ....|....| ....|....| ....|....|
                      110        120        130        140        150
PsAFB2        ALAKSRVGLE ELRLKRMVVS DESLELLSRS FMNFKSLVLV SCEGFTTDGL
AtAFB2        ALARSRVGLE ELRLKRMVVT DESLELLSRS FVNFKSLVLV SCEGFTTDGL
AtAFB3        ALARSRVGLE ELRLKRMVVT DESLDLLSRS FANFKSLVLV SCEGFTTDGL
PtrAFB2A      AFARNSVGLE ELKLKRMIIS DECLELISRS FPNFKSLVLV SCEGFTADGL
PtrAFB2B      AFARNNMGLE ELKLKRMIIS DECLELISRS FANFKSLVLV SCEGFSTDGL
MtAFB2        ALAKNKVGLE ELRLKRMVVS DESLELLSRS FVNFKSLVLV SCEGFTTDGL
OsAFB2A       AAARGCHGLE ELRMKRMVVS DESLELLARS FPRFRALVLI SCEGFSTDGL
OsAFB2B       ACVAACPGLE ELRLKRMVVT DGCLKLLACS FPNLKSLVLV GCQGFSTDGL

....|....| ....|....| ....|....| ....|....| ....|....|
                      160        170        180        190        200
PsAFB2        AAVAANCRSL RELDLQENEV EDHKGQWLSC FPENCTSLVA LNFACLKGEI
AtAFB2        ASIAANCRHL RDLDLQENEI DDHRGQWLSC FPDTCTTLVT LNFACLEGET
AtAFB3        ASIAANCRHL RELDLQENEI DDHRGQWLNC FPDSCTTLMS LNFACLKGET
PtrAFB2A       AAIASNCRFL RELDLQENDV EDHRGHWLSC FPDTCTSLVS LNFACLKGEV
PtrAFB2B       AAIASNCRFL RELDLQENDV EDHRGHWLSF FPDTCTSLVS LNFACLKGDV
MtAFB2        AAVAANCRSL RELDLQENEV EDHKGQWLSC FPESCTSLVS LNFACLKGDI
OsAFB2A       AAVASHCKLL RELDLQENEV EDRGPRWLSC FPDSCTSLVS LNFACIKGEV
OsAFB2B       ATVATNCRFM KELDLQESLV EDRDSRWLGC FPKPSTLLES LNFSCLTGEV

....|....| ....|....| ....|....| ....|....| ....|....|
                      210        220        230        240        250
PsAFB2        NVGALERLVA RSPNLKTLRL NRSVPADALQ RILMRAPQIA DLGIGSFIHD
AtAFB2        NLVALERLVA RSPNLKSLKL NRAVPLDALA RLMACAPQIV DLGVGSYEND
```

FIG. 13B

```
AtAFB3     NVAALERLVA RSPNLKSLKL NRAVPLDALA RLMSCAPQLV DLGVGSYENE
PtrAFB2A   NVAALERLIA RSPNLRSLRL NHAVPLDVLQ KILIRAPHLV DLGVGSYVND
PtrAFB2B   NLAALERLVA RSPNLRSLRL NHAVPLDILQ KILMRAPHLV DLGVGSYVHD
MtAFB2     NLGALERLVS RSPNLKSLRL NRSVPVDALQ RILTRAPQLM DLGIGSFFHD
OsAFB2A    NAGSLERLVS RSPNLRSLRL NRSVSVDTLA KILLRTPNLE DLGTGNLTDD
OsAFB2B    NSPALEILVA RSPNLRSLRL NRSVPLDVLA RILCRRPRLV DLCTGSFVRG

....|....| ....|....| ....|....| ....|....| ....|....|
                     260        270        280        290        300
PsAFB2     LNSEAYIKLK NTILRCRSIT SLSGFLEVAP FSLA-AVYPI CRN--LTSLN
AtAFB2     PDSESYLKLM AVIKKCTSLR SLSGFLEAAP HCLS-AFHPI CHN--LTSLN
AtAFB3     PDPESFAKLM TAIKKYTSLR SLSGFLEVAP LCLP-AFYPI CQN--LISLN
PtrAFB2A   PDSETYNKLV MAIQKCMSVK SLSGFLEVAP HCLS-AFHLI CPN--LTSLN
PtrAFB2B   PDSETYNKLV TALQKCKSVK SLSGFLEAAP QCLS-AFHLI CPN--LTSLN
MtAFB2     LNSDAYAMFK ATILKCKSIT SLSGFLEVAP FSLA-AIYPI CQN--LTSLN
OsAFB2A    FQTESYFKLT SALEKCKMLR SLSGFWDASP VCLS-FIYPL CAQ--LTGLN
OsAFB2B    NIVGAYAGLF NSFQHCSLLK SLSGFWDATS LFIP-VIAPV CKN--LTCLN

....|....| ....|....| ....|....| ....|....| ....|....|
                     310        320        330        340        350
PsAFB2     LSYAASIQGA ELIKLIRHCG KLQRLWIMDC IGDKGLVAVA TICKELQELR
AtAFB2     LSYAAEIHGS HLIKLIQHCK KLQRLWILDS IGDKGLEVVA STCKELQELR
AtAFB3     LSYAAEIQGN HLIKLIQLCK RLQRLWILDS IGDKGLAVVA ATCKELQELR
PtrAFB2A   LSYAPGIHGA ELIKLIRHCM KLQRLWILDC IGDQGLEVVA STCKDLQEIR
PtrAFB2B   LSYAPGIHGT ELIKLIRHCR KLQRLWILDC IGDEGLEVVA STCKHLQEIR
MtAFB2     LSYAAGILGI ELIKLIRHCG KLQRLWIMDR IGDLGLGVVA STCKELQELR
OsAFB2A    LSYAPTLDAS DLTKMISRCV KLQRLWVLDC ISDKGLQVVA SSCKDLQELR
OsAFB2B    LSSAPMVRSA YLIEFICQCK KLQQLWVLDH IGDEGLKIVA SSCIQLQELR

....|....| ....|....| ....|....| ....|....| ....|....|
                     360        370        380        390        400
PsAFB2     VFPSAPFG-- -NQAAVTEVG LVAISKGCPK LHSLLYFCHQ MTNAALITVA
AtAFB2     VFPSDLLG-- GGNTAVTEEG LVAISAGCPK LHSILYFCQQ MTNAALVTVA
AtAFB3     VFPSDVHGEE DNNASVTEVG LVAISAGCPK LHSILYFCKQ MTNAALIAVA
PtrAFB2A   VFPSDPHV-- -GNAAVTEVG LVALSSGCRK LHSILYFCQQ MTNVALITVA
PtrAFB2B   VFPSDPFV-- -GNAAVTEVG LVALSSGCRN LHSILYFCQQ MTNAALITVA
MtAFB2     VFPSAPFG-- -NQAAVTEKG LVAISMGCPK LHSLLYFCHQ MTNAALIAVA
OsAFB2A    VFPSDFYVA- -GYSAVTEEG LVAVSLGCPK LNSLLYFCHQ MTNAALVTVA
OsAFB2B    VFPANANAR- -AST-VTEEG LVAISAGCNK LQSVLYFCQR MTNSALITVA

....|....| ....|....| ....|....| ....|....| ....|....|
                     410        420        430        440        450
PsAFB2     KNCPNFIRFR LCILDATKPD SDTMQPLDEG FGAIVQSCKR LRRLSLSGQL
AtAFB2     KNCPNFIRFR LCILEPNKPD HVTSQPLDEG FGAIVKACKS LRRLSLSGLL
AtAFB3     KNCPNFIRFR LCILEPHKPD HITFQSLDEG FGAIVQACKG LRRLSVSGLL
PtrAFB2A   KNCPNFTRFR LCILDPTKPD AVTNQPLDEG FGAIVHSCKG LRRLSMTGLL
PtrAFB2B   KNCPNFTRFR LCILDPTKPD ADTNQPLDEG FGAIVHSCKG LRRLSMSGLL
MtAFB2     KNCPNFIRFR LCILDATKPD PDTMQPLDEG FGAIVQSCKR LRRLSLSGQL
OsAFB2A    KNCPNFTRFR LCILEPGKPD VVTSQPLDEG FGAIVRECKG LQRLSISGLL
OsAFB2B    KNCPRFTSFR LCVLDPGSAD AVTGQPLDEG YGAIVQSCKG LRRLCLSGLL

```
                  460        470        480        490        500
PsAFB2     TDQVFLYIGM YAEQLEMLSI AFAGESDKGM LYVLNGCKKL RKLEIRDCPF
AtAFB2     TDQVFLYIGM YANQLEMLSI AFAGDTDKGM LYVLNGCKKM KKLEIRDSPF
AtAFB3     TDQVFLYIGM YAEQLEMLSI AFAGDTDKGM LYVLNGCKKM RKLEIRDSPF
PtrAFB2A   TDKVFLYIGM YAEQLEMLSI AFAGDTDKGM QYLLNGCKKL RKLEIRDCPF
PtrAFB2B   TDQVFLYIGM YAEQLEMLSI AFAGDTDKGM QYLLNGCKKL RKLEIRDCPF
MtAFB2     TDQVFLYIGM YAEQLEMLSI AFAGESDKGM LYVLNGCKKI RKLEIRDCPF
OsAFB2A    TDKVFMYIGK YAKQLEMLSI AFAGDSDKGM MHVMNGCKNL RKLEIRDSPF
OsAFB2B    TDTVFLYIGM YAERLEMLSV AFAGDTDDGM TYVLNGCKNL KKLEIRDSPF

....|....| ....|....| ....|....| ....|....| ....|....|
                  510        520        530        540        550
PsAFB2     GDTALLTDVG KYETMRSLWM SSCEVTVGAC KTLAKKMPSL NVEIFN-ESE
AtAFB2     GDTALLADVS KYETMRSLWM SSCEVTLSGC KRLAEKAPWL NVEIIN-END
AtAFB3     GNAALLADVG RYETMRSLWM SSCEVTLGGC KRLAQNSPRL NVEIIN-ENE
PtrAFB2A   GNAALLMDVG KYETMRSLWM SSCEVTLGGC KSLAKKMPRL NVEIIN-END
PtrAFB2B   GNAALLMDVG KYETMRSLWM SSCDITLGGC KSLAKKMPRL NVEIIN-ESD
MtAFB2     GDTALLTDIG KYETMRSLWM SSCEVTVEAC KTLAKKMPRL NVEIFS-ESE
OsAFB2A    GDAALLGNFA RYETMRSLWM SSCNVTLKGC QVLASKMPML NVEVIN-ERD
OsAFB2B    GDSALLAGMH QYEAMRSLWL SSCNVTLGGC KSLAASMANL NIEVMNRA-A

....|....| ....|....| ....|....| ....|....| ....|....|
                  560        570        580        590        600
PsAFB2     Q--------- ---------- --ADCYVEDG QRVEKMYLYR SVAGKREDAP
AtAFB2     NNR------- ---------- -MEENGHEGR QKVDKLYLYR TVVGTRMDAP
AtAFB3     NNG------- ---------- -MEQNEEDER EKVDKLYLYR TVVGTRKDAP
PtrAFB2A   Q--------- ---------- --MDASADDR QKVEKMFLYR TLAGRREDAP
PtrAFB2B   Q--------- ---------- --MDITADDG QKVEKMFLYR TLAGRRKDAP
MtAFB2     Q--------- ---------- --ADCYVEDG QRVEKMYLYR TVAGKREDAP
OsAFB2A    GSN------- ---------- -EMEENHGDL PKVEKLYVYR TTAGARDDAP
OsAFB2B    SIN------- ---------- -EADN-ANDA KKVKKLYIYR TVAGPRGDAP

....|.
PsAFB2     EYVWTL
AtAFB2     PFVWIL
AtAFB3     PYVRIL
PtrAFB2A   EFVWTL
PtrAFB2B   EFVWTL
MtAFB2     DYVWTL
OsAFB2A    NFVKIL
OsAFB2B    EFISTF
```

FIG. 14A
Alignment of AFB6 Proteins

```
            ....|....| ....|....| ....|....| ....|....| ....|....|
                    10         20         30         40         50
PsAFB6A     ---------- ----MEPQTM NPSSV----- -------FPD EVLERILSMV
PtrAFB6A    ---------- ----MKREFL DSTR------ ----SSPFPD EVLERVLSLL
PtrAFB6B    --------MD SNPKMRKEFL DSTR------ ----SSLFPD EVLERVLSLL
MtAFB6A     MNMVECKRKK ESQGEKNNNM DSNSD----- -------FPD EVLERVLGMM
MtAFB6B     ---------- ----MEECKR EK-------- ---------D EVLKQVLGTV

....|....| ....|....| ....|....| ....|....| ....|....|
                    60         70         80         90        100
PsAFB6A     KSRKDKSSVS LVCKDWFDAE RWSRKNVFIG NCYSVTPEIL TQRFPNVRSV
PtrAFB6A    KSHKDRSAVS LVCKDWYNAE SWSRTHVFIG NCYSVSPEIV ARRFPIIKSV
PtrAFB6B    KSHKDRSAVS LVCKDWYNAE SWSRTHVFIG NCYSVSPEIV ARRFPRIKSV
MtAFB6A     KSRKDRSSVS LVCKEWYNAE RWSRRNVFIG NCYAVSPEIL TRRFPNIRSV
MtAFB6B     KSRKDRNSAS LVCKQWYNAE RLSRRNVFIG NCYSVTPEIL TRRFPNIRSI

....|....| ....|....| ....|....| ....|....| ....|....|
                   110        120        130        140        150
PsAFB6A     TLKGKPRFSD FNLVPANWGA DIHPWLVVFA EKYPFLEELR LKRMVVTDES
PtrAFB6A    TLKGKPRFSD FNLVPENWGA DVHPWLVVFA TKYPFLEELR LKRMAVSDES
PtrAFB6B    TLKGKPRFSD FNLVPENWGA DVHPWFVVFA AKYPFLEELR LKRMAVSDES
MtAFB6A     TMKGKPRFSD FNLVPANWGA DIHSWLVVFA DKYPFLEELR LKRMAVSDES
MtAFB6B     TLKGKPRFSD FNLVPENWGA DIHSWLVVFA EKYPFLEELR LKRMVVTDES

....|....| ....|....| ....|....| ....|....| ....|....|
                   160        170        180        190        200
PsAFB6A     LEFLAFSFPN FKALSLLSCD GFSTDGLAAV ATNCKNLTEL DIQENGIEDK
PtrAFB6A    LEFLAVNFPN FKVLSLLSCD GFSTDGLAAI ATHCKSLTQL DIQENGIDDK
PtrAFB6B    LEFLALNFPN FKVLSLLSCD GFSTDGLAAI ATHCKNLTQL DVQENGIDDK
MtAFB6A     LEFLAFSFPN FKALSLLSCD GFSTDGLAAV ATNCKNLTEL DIQENGVDDK
MtAFB6B     LEFLAFSFHN FKALSLLSCE GFSTDGLAAV AANCKNLTEL DIQENDIDDK

....|....| ....|....| ....|....| ....|....| ....|....|
                   210        220        230        240        250
PsAFB6A     SGNWLSCFPE SFTSLEVLNF ANLTNEVNID ALEKLVGRCK -SLKTLKVNK
PtrAFB6A    SGGWLSCFPE NFTSLEVLNF ANLNTDVNFD ALERLVSRCK -SLKVLKVNK
PtrAFB6B    SGNWLSCFPE NFTSLEVLNF ANLNTDVNFD ALERLVSRCK -SLKVLKANK
MtAFB6A     SGNWLSCFPE SFTSLEILNF ANLSNDVNFD ALEKLVARCN -SLKTLKVNK
MtAFB6B     SGDWLSCFPE SFTSLEVLNF ANLNNDVNID ALEKLVGRCK -SLKTLKVNK

....|....| ....|....| ....|....| ....|....| ....|....|
                   260        270        280        290        300
PsAFB6A     SVTLEQLKKL LVRAPQLCEL GSGSFS-QEL TSQQYAELET AFKNCKSLHT
PtrAFB6A    SISLEHLQRL LVCAPQLTEL GTGSFT-PEL TTRQYAELES AFNQCKNLHT
PtrAFB6B    SISLEHLQRL LVCAPQLTEL GTGSFM-PEL TARQYAELGS SFNQLKNLNT
MtAFB6A     SVTLEQLQRL LVRAPQLCEL GTGSFS-QEL TGQQYSELER AFNNCRSLHT
MtAFB6B     SVTLEQFQRL LVLAPQLCEL GSGSFS-QDL TCQQYLELES AFKNCKSLHT

....|....| ....|....| ....|....| ....|....| ....|....|
                   310        320        330        340        350
PsAFB6A     LSGLWVASAR YL----QVLY PACANLTFLN FSYAPLDSED LTKILVHCPN
```

FIG. 14B

```
PtrAFB6A    LSGLWEATAL  YL----PVLY  PVCSNLTFLN  LSYTFLQSLE  LASLLRQCPR
PtrAFB6B    LSGLWEATAP  YL----PVLY  PACTNLTFLN  LSYAFLQSIE  LASLLCQCPR
MtAFB6A     LSGLWVASAQ  YH----QVLY  PVCTNLTFLN  FSYAPLDSEG  LSKLLVRCPN
MtAFB6B     LSGLWVASAS  AQYIQLQVLY  SACTNLTFLN  FSYALVDSED  LTDLLVHCPN

....|....|  ....|....|  ....|....|  ....|....|  ....|....|
                   360         370         380         390         400
PsAFB6A     LRRLWVVDTV  EDKGLEAVGS  NCPLLEELRV  FPADPFDEEA  EGGVTESGFV
PtrAFB6A    LRRLWVLDTV  GDKGLEAVGS  NCPLLEELRV  FPADPFDEEI  IHGVTEAGFV
PtrAFB6B    LRRLWVLDTV  GDKGLEAVGS  NCPLLEELRV  FPADPFDEEV  IHGVTEAGFL
MtAFB6A     LRRLWVLDTV  EDKGLEAVGS  YCPLLEELRV  FPGDPFEEGA  AHGVTESGFI
MtAFB6B     LRRLWVVDTV  EDKGLEAVGS  YCPLLEELRV  FPADPFDEGV  VHGVTESGFI

....|....|  ....|....|  ....|....|  ....|....|  ....|....|
                   410         420         430         440         450
PsAFB6A     AVSEGCRKLH  YVLYFCRQMT  NAAVATVVQN  CPDFTHFRLC  IMNPGQQDYL
PtrAFB6A    AVSYGCRRLH  YVLYFCRQMT  NAAVATIVQN  CPDFTHFRLC  IMNPGQPDYL
PtrAFB6B    AVSYGCRRLH  YVLYFCRQMT  NAAVATIVQN  CPDFTHFRLC  IMNPGQPDYL
MtAFB6A     AVSEGCRKLH  YVLYFCRQMT  NAAVATVVEN  CPDFTHFRLC  IMTPGQPDYQ
MtAFB6B     AVSEGCRKLH  YILYFCHQMT  NDAVATVVQN  CPDFTHFRLC  IMTPNQPDYL

....|....|  ....|....|  ....|....|  ....|....|  ....|....|
                   460         470         480         490         500
PsAFB6A     TDEPMDEAFG  EVVKNCTKLQ  RLAVSGYLTD  LTFEYIGKYA  KNLETLSVAF
PtrAFB6A    TNEPMDEAFG  AVVRTCTKLQ  RLSVSGLLTD  LTFEYIGQYA  KNLETLSVAF
PtrAFB6B    TNEPMDEAFG  AVVRTCTKLQ  RLSVSGLLTD  LTFEYIGQYA  KNLETLSVAF
MtAFB6A     TGEPMDEAFG  AVVKTCTKLQ  RLAVSGSLTD  LTFEYIGKYA  KNLETLSVAF
MtAFB6B     TNEPMDEAFG  AVVKTCTKLQ  RLSVSGYLTD  LAFEYIGKYA  KNLETLSVAF

....|....|  ....|....|  ....|....|  ....|....|  ....|....|
                   510         520         530         540         550
PsAFB6A     AGSSDWGMEC  VLVGCPKLRK  LEIRDSPFGN  AALLAGLEKY  ESMRSLWMSS
PtrAFB6A    AGSSDRGMQC  VLEGCPKLRK  LEIRDCPFGN  AALLSGLEKY  ESMRSLWMSA
PtrAFB6B    AGSSDRGMQC  MLEGCPKLRK  LEIRDCPFGN  AALLSGLEKY  ESMRSLWMSA
MtAFB6A     AGSSDWAMQC  VLVGCPKLRK  LEIRDSPFGN  AALLSGFDKY  ESMRSLWMSD
MtAFB6B     AGSSDLGMQC  VLAGCPKLKK  LEIRDCPFGD  AALLSGLEKY  ESMRSLWMSD

....|....|  ....|....|  ....|....|  ....|....|  ....|....|
                   560         570         580         590         600
PsAFB6A     CRLTMNGCRF  LAGEKPRLNV  EVMQEEGGD-  DSRAEKLYVY  RSVAGPRRDA
PtrAFB6A    CNVTMNGCRL  LAREMPRLNV  EVMKEDSD-   DSQADKVYVY  RSVAGPRRDA
PtrAFB6B    CNVTMNGCRV  LAREMPRLNV  EVMKEDSD-   DSQADKVYVY  RSVVGPRRDA
MtAFB6A     CKVTMNGCRL  LAQERPRLNV  EVMQEEGGD-  DSQAGKLYVY  RSVAGPRRDA
MtAFB6B     CQVTMNGCRL  LAKEKPRLNV  EVIKEEGSG-  DSQAEKVYVY  RSVAGPRRDA

....|....|
                   610
PsAFB6A     PPFVLTL---
PtrAFB6A    PPCVLTLSGL
PtrAFB6B    PPCVLTLSGL
MtAFB6A     PPFVLTL---
MtAFB6B     PLFVLTL---
```

AUXIN RECEPTORS

FIELD OF THE INVENTION

The invention relates to isolated polynucleotide and polypeptides of the PsAFB2 and PsAFB6 genes from *Pisum sativum*; nucleic acid constructs, vectors and host cells incorporating the polynucleotide sequences; and methods of producing and using same.

BACKGROUND OF THE INVENTION

As a class of phytohormones, auxins influence virtually every developmental program in plants. Examples of auxins include indole-3-acetic acid (IAA) which is synthesized from tryptophan, indole or indole-3-glycerol phosphate via multiple parallel biochemical pathways (reviewed in Bartel, 1997); indole-3-butyric acid in pea (Schneider et al., 1985) which can be converted to IAA in vivo (Nordstrom et al., 1991); and 4-chloroindole-3-acetic acid (4-Cl-IAA) which has been identified in a number of legumes but seems to be restricted to only certain genera including *Pisum sativum* (Marumo et al., 1968; Katayama et al., 1988) and *Vicia amurensis* (Katayama et al., 1987), but not in the closely related *Phaseoleae* genus (Katayama et al., 1987).

Auxins play vital roles in the coordination of seed and fruit growth in pea. The presence of viable, developing seeds is a prerequisite for pericarp development. Seed removal early in fruit development retards pericarp growth, eventually leading to pericarp senescence (Ozga et al., 1992). Mounting evidence supports the hypothesis that seed-derived signals promote pericarp growth in pea. While the application of bioactive $GA_3$ or $GA_1$ to the endocarp of deseeded pericarps can stimulate pericarp growth (Ozga and Reinecke, 1999), GA transport from the seeds to the pericarp is likely minimal. In the pea GA biosynthesis mutant na, which possesses a loss of function mutation in an ent-kaurene oxidase gene (PsKO1) primarily expressed in vegetative tissues (producing a severely dwarfed plant), the presence of the wildtype seed expressed PsKO2 homolog allows seeds of na mutant plants to develop with normal GA levels, while GA levels in the pod are severely reduced (Davidson et al., 2003). A similar lack of apparent seed to pericarp GA transport was observed in the ls-1 GA biosynthesis mutant (partial loss of the ability to convert GGDP to CPP early in the GA biosynthesis pathway), where pericarp $GA_1$ levels were significantly lower than in wildtype plants while seed $GA_1$ was comparable to wildtype levels (Reid and Ross, 1993).

While transport of bioactive GAs from the seeds to the pericarp as a growth-inducing signal are likely minimal, 4-Cl-IAA can substitute for seeds in many aspects of pericarp growth, and may be a primary seed-to-pericarp growth signal in pea. 4-Cl-IAA accumulates in both the seeds and pericarps of pea (Magnus et al., 1997), and in the absence of viable seeds, 4-Cl-IAA can stimulate pericarp growth (Reinecke et al., 1995). 4-Cl-IAA-stimulated pericarp growth is mediated partially by GAs through the local upregulation of the GA biosynthesis pathway in the pericarp. While $[^{14}C]$ $GA_{12}$ is efficiently metabolized to $GA_{19}$ and $GA_{20}$ by pericarps with intact seeds, in deseeded pericarps $[^{14}C]GA_{19}$ accumulates, but $[^{14}C]GA_{20}$ does not, indicating that seeds have a role in the conversion of $GA_{19}$ to $GA_{20}$ within the pericarp (Ozga et al., 1992). A similar pattern was observed in the profile of endogenous GAs in the pericarp. In pericarp with seeds, $GA_{19}$, $GA_{20}$, $GA_1$, and $GA_8$ were detected; however, in deseeded pericarps, $GA_{19}$ accumulated, while $GA_{20}$, $GA_1$, and $GA_8$ were not detected, suggesting a block in the GA pathway at the oxidation step between $GA_{19}$ and $GA_{20}$ due to seed removal (Ozga et al., 1992). When applied to the pericarp via a split-pericarp technique, $[^{14}C]GA_{19}$ was readily converted to $[^{14}C]GA_{20}$ and $[^{14}C]GA_{29}$ in fruit with seeds, while in deseeded pericarps, the production of $[^{14}C]$ $GA_{20}$ and $[^{14}C]GA_{29}$ was reduced (van Huizen et al., 1995). Steady-state pericarp transcript abundance of PsGA20ox1, the enzyme product of which can convert $GA_{19}$ to $GA_{20}$, was lower in deseeded pericarps than in pericarps with seeds, confirming the results of the $[^{14}C]GA_{12}$ metabolism studies which indicate that seeds are important for pericarp $GA_{20}$ biosynthesis (van Huizen et al., 1997).

The application of 4-Cl-IAA to deseeded pericarps stimulated the conversion of radiolabelled $GA_{12}$ or $GA_{19}$ to $GA_{20}$ (van Huizen et al., 1995; Ozga et al., 2009), and increased steady-state transcript levels of PsGA20ox1 (van Huizen et al., 1997; Ozga et al., 2009), mimicking the presence of the seeds. In addition to promoting the production of pericarp $GA_{20}$, seeds are also involved in the regulation of GA 3β-hydroxylase activity, as indicated by the reduction of steady-state PsGA3ox1 in deseeded pericarps in comparison to controls with viable seeds. The application of 4-Cl-IAA to deseeded pericarps once again increased steady-state PsGA3ox1 mRNA levels (Ozga et al., 2003), much as with PsGA20ox1. Additionally, upon treatment with 4-Cl-IAA, deseeded pericarps were able to convert $[^{14}C]GA_{12}$ to $[^{14}C]$ $GA_1$, which did not occur in the absence of 4-Cl-IAA treatment, indicating the restoration of GA pathway flux in the pericarp by this auxin (Ozga et al., 2009). Transcript abundance of the catabolic gene PsGA2ox1 was elevated in pericarps lacking seeds, and 4-Cl-IAA, but not IAA, reduced PsGA2ox1 transcript to levels comparable to those in pericarps containing viable seeds (Ozga et al., 2009). Between 2 and 3 days after anthesis (DAA), pericarps with viable seeds displayed a transitory increase in transcript abundance of the catabolic gene PsGA2ox2, possibly as part of a regulatory mechanism to support the transition between developmental programs of fruit set and sustained pericarp growth. While PsGA2ox2 transcript levels do not increase in deseeded pericarps, the application of 4-Cl-IAA (but not IAA) to the pericarp can mimic the seed-induced transitory increase in pericarp PsGA2ox2 transcript (Ozga et al., 2009).

The presence of two natural auxins with varying developmental roles provides a unique system in which to study the relationship between physiological activity and auxin structure. Using a split-pericarp pod elongation assay, Reinecke et al. (1995) tested the ability of a variety of halogenated auxins (4-, 5-, 6-, and 7-chloro- and fluoroindole-3-acetic acid) to promote deseeded pericarp growth. While 4-Cl-IAA stimulated pericarp growth, the other auxins tested generally did not stimulate growth. Similar research using a variety of 4-substituted auxins (4-H-IAA, 4-Cl-IAA, 4-Fl-IAA, 4-Me-IAA, and 4-Et-IAA) found that 4-Me-IAA was also capable of stimulating the expansion of deseeded pericarps, but not to the same extent as 4-Cl-IAA (Reinecke et al., 1999). Recent studies of structure-activity relationships in pea pericarp suggests that the position, size, and lipophilicity of the indole-substituent are important for determining biological activity, with optimal activity obtained with a hydrophobic substituent of approximately the same size as a chlorine atom at the 4-position of the indole ring (Reinecke et al., 1999).

Auxins occur in plants as free acids and in conjugated forms. Auxin conjugates include auxin linked to single amino acids or to mono- or disaccharides (Bandurski et al., 1995). IAA can be covalently bound to proteins (Bialek and Cohen, 1989). Auxin conjugation has been implicated as a storage mechanism, where, in addition to de novo synthesis, free auxin can be generated upon cleavage from these bound forms (Bandurski et al., 1995; Woodward and Bartel, 2005). Conjugated auxins in pea include amide conjugates such as indole-3-acetylaspartic acid (Law and Hamilton, 1982) and esterified compounds, such as 1-O-indole-3-acetyl-β-D-glucose (Jakubowska and Kowalczyk, 2004). The ratio between amide and ester conjugates varies between tissues (Bandurski and Schulze, 1977; Magnus et al. 1997), suggesting a developmental role for auxin conjugation in pea. In pea, 4-Cl-IAA has been implicated as a fruit growth promoting auxin (Reinecke et al., 1995; Reinecke et al., 1999; Ozga and Reinecke, 2003).

Most research in auxin signalling has been performed in *Arabidopsis*. Shortly after application of auxins to *Arabidopsis* seedlings, a group of transcriptional repressors (the Aux/IAA genes) are upregulated (Leyser, 2002). Aux/IAA proteins are transcriptional repressors and contain an N-terminal transcriptional repressor called domain I (Tiwari et al., 2001), domain II, involved in protein stability and degradation (Park et al., 2002), and two C-terminal dimerization domains III and IV.

Auxin Response Factors (ARF) are similar to the Aux/IAA proteins in structure (Ulmasov et al., 1999), and contain an N-terminal DNA-binding domain, an RNA polymerase II interaction domain (Hagen and Guilfoyle, 2002), and two dimerization domains similar in structure to domains III and IV of the Aux/IAA repressors. The DNA-binding domain recognizes a sequence that consists minimally of a conserved sequence (5'-TGTCTC). This sequence, combined with a secondary constitutive element in some genes (Ulmasov et al., 1995), constitutes the auxin responsive element (ARE), which is necessary and sufficient to confer auxin inducibility to reporter genes. While the Aux/IAA proteins are transcriptional repressors, ARFs can act as transcriptional repressors or activators (Hagen and Guilfoyle, 2002). These two groups of proteins are capable of both homo- and heterodimerization freely with one another. In the absence of auxin, a heterodimer consisting of one Aux/IAA repressor and one ARF protein (either a repressor or an activator) is bound at the ARE of an auxin-inducible gene, inhibiting transcription. Upon auxin induction, the Aux/IAA protein of that dimmer is degraded, which allows the formation of a new homo- or heterodimer, effecting changes in gene transcription.

The degradation of Aux/IAA proteins relies on the SCF complex composed of Skp1, Cullin, and F-box (Gray et al., 1999; FIG. 1). The SCF complex is an E3 ubiquitin ligase involved in several signal transduction pathways, including those for gibberellin and jasmonic acid. Skp1 is a scaffold protein, and interacts with two of the other complex members. Cullin transfers ubiquitin subunits from an E2 ubiquitin conjugating enzyme to a specific target protein, and functions as a heterodimer with a fourth protein, RBX1. The F-box proteins are a diverse family of proteins containing a protein-protein interaction domain which interacts with Skp1 called the F-box, and a variety of C-terminal protein-protein interaction domains which confer target specificity to the complex (leucine rich repeats for the AFB family of F-box proteins (Gagne et al., 2002), although a variety of other domain types are present in other groups of F-box proteins).

In addition to contributing target specificity to the SCF complex, the F-box proteins TIR1, AFB2, and AFB3, function as auxin receptors (Dharmasiri et al., 2005a). The AFB F-box proteins bind auxins directly, and the formation of the auxin-AFB complex is necessary for the binding of Aux/IAA proteins by the SCF (Kepinski and Leyser, 2005). The crystal structure of the TIR1 protein in *Arabidopsis* in the presence and absence of auxin was obtained (Tan et al., 2007). While the F-box region of the AFB proteins interact with the SCF scaffold protein (ASK1 in *Arabidopsis*), the C-terminal LRRs form an open pocket. The auxin molecule sits in the proximal end of the pocket and acts as a molecular glue, mediating contact between the AFB protein and the targeted Aux/IAA protein. This binding is likely promoted by van der Waals, hydrophobic, and hydrogen-bonding interactions, and may explain why a number of relatively hydrophobic molecules of approximately the same size and general structure can serve as auxins.

Upon the introduction of auxin into the nucleus, events unfold which culminate in the alteration of transcription profiles of auxin-regulated genes. Initially, auxin binds to the LRR region of the AFB protein of the SCF complex. The auxin molecule mediates interactions between the AFB protein of the SCF complex and the target Aux/IAA protein, which may be part of an inhibitory Aux/IAA-ARF heterodimer. The Cullin subunit of SCF then transfers, iteratively, ubiquitin peptides from E2 ubiquitin conjugating enzymes to a site in domain II of the Aux/IAA protein (Dharmasiri and Estelle, 2004). The ubiquitinated Aux/IAA protein is shuttled to the 26s proteasome for degradation (Gray et al., 2001), freeing the formerly bound ARF protein to interact with other subunits. Another ARF subunit or a second Aux/IAA protein (if more are available) can then dimerize with the pre-existing ARF protein, either promoting or inhibiting transcription of the auxin-responsive gene, leading to a variety of physiological and developmental changes (Dharmasiri et al., 2005b; FIG. 2). In the absence of an appropriate auxin, an ARF-Aux/IAA heterodimer binds the upstream ARE sequence, preventing transcription. Upon degradation of the Aux/IAA protein by the auxin-activated SCF complex, an ARF homodimer can form, recruiting RNApol II and increasing transcription.

SUMMARY OF THE INVENTION

Without restriction to a theory, we believe that abiotic stresses modulate auxin receptor abundance in plant flowers, seeds and ovaries, and the resultant auxin receptor population will determine the fate of the developing fruit. Therefore, modulation of the auxin receptor population at the transcript level or protein level can ameliorate abiotic stress symptoms in reproductive tissues in species that contain this auxin receptor clade.

In one aspect, the invention may comprise plants modified to underexpress PsABF6 (using either transgenic or non-trangenic approaches), which will then be resistant to flower and fruit abortion when grown under normal and abiotic stress conditions (including water stresses such as drought or water logging, heat and cold temperature stress, and salt stress).

In another aspect, the invention may comprise plants modified to reduce the proportion of PsAFB6 receptors, which are negative regulators of growth, to other auxin receptors which are positive regulors of growth, such as AFB2. In one embodiment, plants that overexpress the auxin receptor PsAFB2, or express PsAFB2 in greater proportion to PsAFB6, during abiotic stress conditions (for example plants transformed with AFB2 linked to a stress-induced promoter) will be resistant to flower and/or fruit abortion when grown under abiotic stress conditions. The combination of increasing auxin receptors that are positive regulators of growth, such as PsAFB2, with decreasing auxin receptors that are negative regulators of growth, such as PsAFB6, during abiotic stress may lead to greater retention of flowers and fruits than modulation of only one auxin receptor gene. The increase or decrease in auxin receptors may be accomplished by modulating mRNA abundance of these genes through conventional transgenic or non-transgenic methods.

Therefore, in another aspect, the present invention relates to isolated polynucleotide and polypeptides of the PsAFB2 and PsAFB6 genes from *Pisum sativum*; nucleic acid constructs, vectors and host cells incorporating the polynucleotide sequences; and methods of producing and using same.

In one aspect, the invention comprises an isolated polynucleotide encoding a polypeptide comprising an amino acid sequence selected from:
  (a) at least 300, at least 400 or at least 500 contiguous residues of the amino acid sequence of SEQ ID NO: 2 or of an amino acid sequence having at least 85% sequence identity therewith; or
  (b) at least 300, at least 400 or at least 500 contiguous residues of the amino acid sequence of SEQ ID NO: 4 or of an amino acid sequence having at least 85% sequence identity therewith,
wherein expression of the polynucleotide in a plant modulates abiotic stress tolerance in the plant.

In one embodiment, the polynucleotide comprises the nucleotide sequence of SEQ ID NO: 1 and expression of the polynucleotide increases abiotic stress tolerance.

In one embodiment, the polynucleotide comprises the nucleotide sequence of SEQ ID NO: 3 and expression of the polynucleotide decreases abiotic stress tolerance.

In one embodiment, the encoded polypeptide comprises the amino acid sequence of SEQ ID NO: 2.

In one embodiment, the encoded polypeptide comprises the amino acid sequence of SEQ ID NO: 4.

In one embodiment, the encoded polypeptide comprises an amino acid sequence having at least 90%, at least 95%, at least 96%, at least 97%, at least 98%, or at least 99% sequence identity to SEQ ID NO: 2.

In one embodiment, the encoded polypeptide comprises an amino acid sequence having at least 90%, at least 95%, at least 96%, at least 97%, at least 98%, or at least 99% sequence identity to SEQ ID NO: 4.

In another aspect, the invention comprises a polynucleotide construct comprising any of the above polynucleotides operably linked to a promoter expressible in bacterial, yeast, fungal, mammalian or plant cells.

In another aspect, the invention comprises a vector comprising any of the above polynucleotides.

In another aspect, the invention comprises a microbial cell comprising any of the above polynucleotides. In one embodiment, the microbial cell is selected from *Aspergillus, Pichia pastoris, Saccharomyces cerevisiae, E. coli*, or *Bacillus subtilis*.

In another aspect, the invention comprises a transgenic plant, plant cell, plant seed, callus, plant embryo, microspore-derived embryo, or microspore, comprising any of the above polynucleotides. In one embodiment, the transgenic plant, plant cell, plant seed, callus, plant embryo, microspore-derived embryo, or microspore is flax, canola, oats, wheat, triticale, barley, corn, a legume plant (including soybean).

In yet another aspect, the invention comprises a method for producing a transgenic plant comprising the steps of introducing into a plant cell or a plant tissue any of the above polynucleotides to produce a transformed cell or plant tissue; and cultivating the transformed plant cell or transformed plant tissue to produce the transgenic plant, wherein the transgenic plant exhibits an increased tolerance to an abiotic stress compared to an untransformed plant of the same species. In one embodiment, the plant is selected from a flax, canola, oats, wheat, triticale, barley, corn, or legume plant. In one embodiment, the abiotic stress is selected from drought, water logging, salt, cold, heat, frost, wind, and acid rain. In one embodiment, the transgenic plant exhibits a lower rate of seed or fruit abortion as compared to an untransformed plant of the same species.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings:

FIGS. 6A-B show the cDNA sequence of the putative coding region of PsAFB2 (sense strand) (SEQ ID NO: 1). Regions corresponding to putative F-box and LRR domains in the predicted protein are identified underneath the sequence (Table 1; FIGS. 13A-C), and qRT-PCR primer an probe binding sites are additionally underlined (Table 8).

FIGS. 7A-B show the cDNA sequence of the putative coding region of PsAFB6 (sense strand) (SEQ ID NO: 2). Regions corresponding to putative F-box and LRR domains in the predicted protein are identified underneath the sequence (Table 1; FIGS. 14A-B), and qRT-PCR primer andprobe binding sites are additionally underlined (Table 1).

FIGS. 13A-C show putative PSAFB2 protein (SEQ ID NO: 2) aligned with AFB2/3 homologues from other species (Ps=*Pisum sativum*, At=*Arabidopsis thaliana*, Ptr=*Populus trichocarpa*, Mt=*Medicago truncatula*, Gm=*Glycine max*, Os=*Oryza sativa*. F-box is underlined and in bold, while predicted leucine rich repeats are underlined and italicized).

FIGS. 14A-B show putative PSAFB6 protein (SEQ ID NO: 4) aligned with AFB6 homologues from other species (Ps=*Pisum sativum*, Mt=*Medicago truncatula*, Ptr=*Populus trichocarpa*. F-box is underlined and in bold, while predicted leucine rich repeats are underlined and italicized).

DETAILED DESCRIPTION OF PREFERRED EMBODIMENTS

Figure 1:
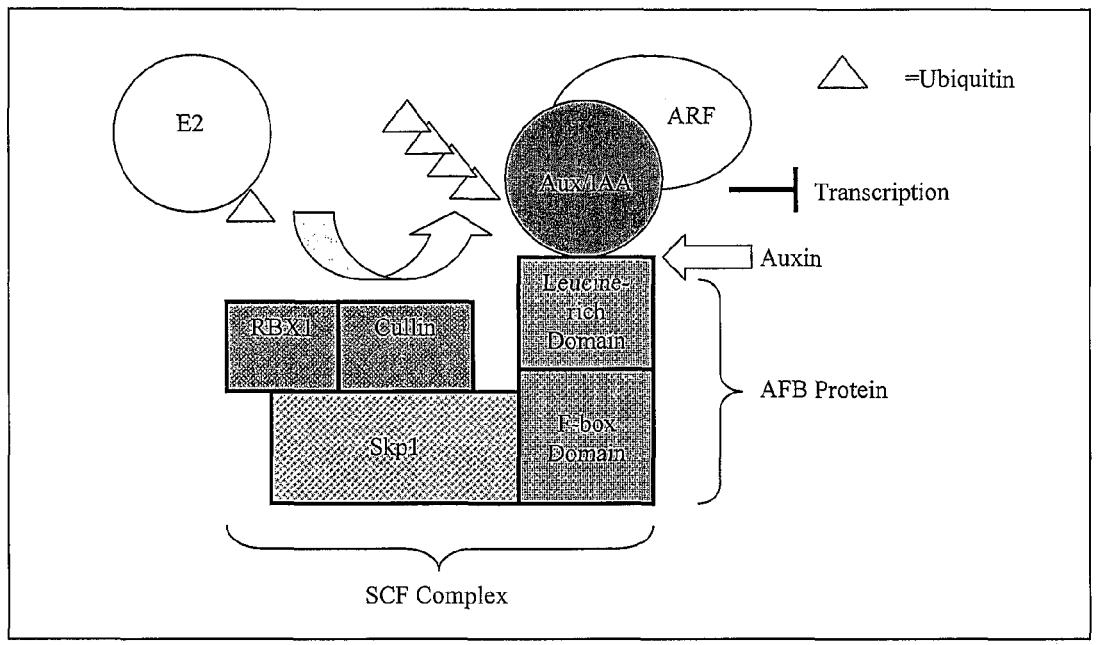
FIG. 1 is a schematic diagram of SCF complex indicating interactions with key components of the auxin signalling pathway.
Figure 2:
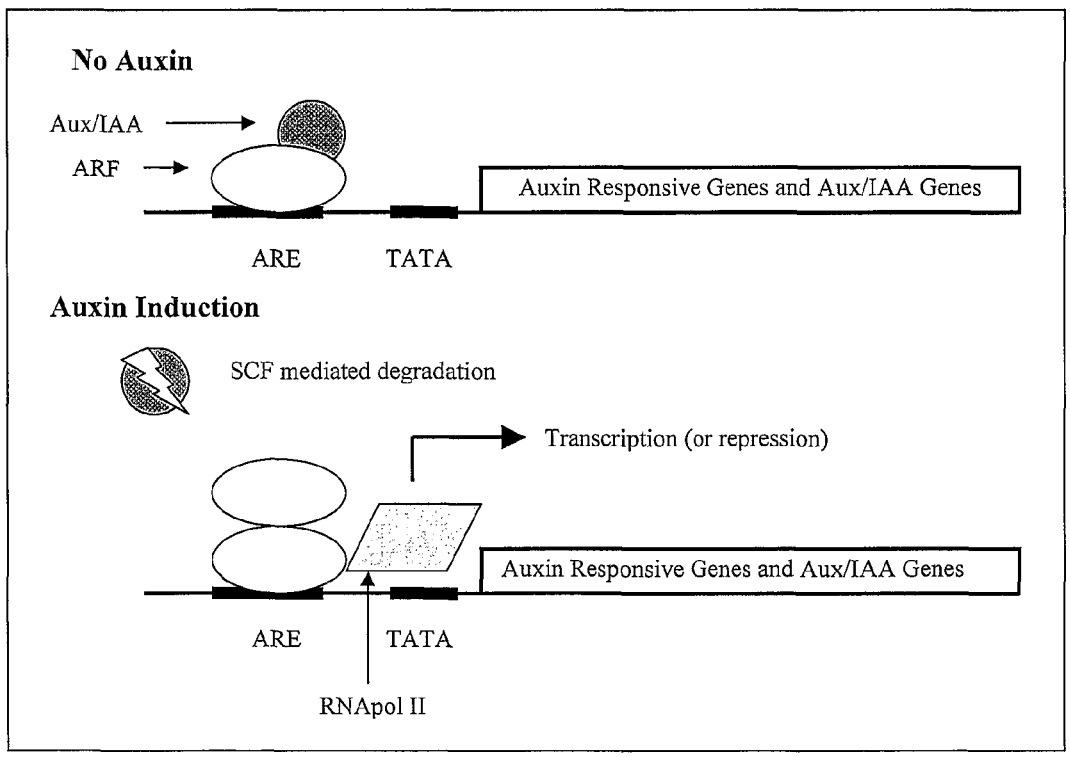
FIG. 2 is a schematic diagram of auxin regulation of gene transcription.

The present invention relates to plants which have modulated auxin receptor expression profiles and which are resistant to flower and fruit abortion, particularly under abiotic stress conditions. In particular, the present invention relates to isolated polynucleotides encoding polypeptides of the PsAFB2 and PSAFB6 genes from *Pisum sativum*; nucleic acid constructs, vectors, host cells and plants incorporating the polynucleotide sequences; and methods of producing and using same.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims. To facilitate understanding of the invention, the following definitions are provided.

"Abiotic stress" is an environmental factor which can have harmful effects on plants including, for example, drought, water logging, mild to extreme cold or heat, frost, high winds, high salt environment and acid rain.

"Auxin" is a class of plant growth substances and morphogens (phytohormones or plant hormones) which promote and regulate the growth and development of plants including cell division and elongation, differentiation, tropisms, apical dominance, senescence, abscission and flowering.

An "auxin modulator" is a polypeptide capable of binding auxin and initiating a cascade of events related to the growth and development of plants.

A "cDNA" is a polynucleotide which is complementary to a molecule of mRNA. The "cDNA" is formed of a coding sequence flanked by 5' and 3' untranslated sequences.

A "coding sequence" or "coding region" or "open reading frame (ORF)" is part of a gene that codes for an amino acid sequence of a polypeptide.

A "complementary sequence" is a sequence of nucleotides which forms a duplex with another sequence of nucleotides according to Watson-Crick base pairing rules where "A" pairs with "T" and "C" pairs with "G."

A "construct" is a polynucleotide which is formed by polynucleotide segments isolated from a naturally occurring gene or which is chemically synthesized. The "construct" is combined in a manner that otherwise would not exist in nature, and is usually made to achieve certain purposes. For instance, the coding region from "gene A" can be combined with an inducible promoter from "gene B" so the expression of the recombinant construct can be induced.

"Downstream" means on the 3' side of a polynucleotide while "upstream" means on the 5' side of a polynucleotide.

"Expression" refers to the transcription of a gene into RNA (rRNA, tRNA) or messenger RNA (mRNA) with subsequent translation into a protein.

Two polynucleotides or polypeptides are "identical" if the sequence of nucleotides or amino acids, respectively, in the two sequences is the same when aligned for maximum correspondence as described here. Sequence comparisons between two or more polynucleotides or polypeptides can be generally performed by comparing portions of the two sequences over a comparison window which can be from about 20 to about 200 nucleotides or amino acids, or more. The "percentage of sequence identity" may be determined by comparing two optimally aligned sequences over a comparison window, wherein the portion of a polynucleotide or a polypeptide sequence may include additions (i.e., insertions) or deletions (i.e., gaps) as compared to the reference sequence. The percentage is calculated by determining the positions at which identical nucleotides or identical amino acids are present, dividing by the number of positions in the window and multiplying the result by 100 to yield the percentage of sequence identity. Polynucleotide and polypeptide sequence alignment may be performed by implementing specialized algorithms or by inspection. Examples of sequence comparison and multiple sequence alignment algorithms are: BLAST and ClustalW softwares. Identity between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. Hybridization methods are described in Ausubel et al. (1995).

"Isolated" means that a substance or a group of substances is removed from the coexisting materials of its natural state.

A "legume" plant is from the family Fabaceae or Leguminosae, and includes, without limitation, plants such as alfalfa, clover, pea, bean, lentil, lupin, chickpea, faba bean, mesquite, carob, soybean, or peanut.

A "polynucleotide" is a linear sequence of ribonucleotides (RNA) or deoxyribonucleotides (DNA) in which the 3' carbon of the pentose sugar of one nucleotide is linked to the 5' carbon of the pentose sugar of another nucleotide. The deoxyribonucleotide bases are abbreviated as "A" deoxyadenine; "C" deoxycytidine; "G" deoxyguanine; "T" deoxythymidine; "I" deoxyinosine. Some oligonucleotides described herein are produced synthetically and contain different deoxyribonucleotides occupying the same position in the sequence. The blends of deoxyribonucleotides are abbreviated as "W" A or T; "Y" C or T; "H" A, C or T; "K" G or T; "D" A, G or T; "B" C, G or T; "N" A, C, G or T.

A "polypeptide" is a linear sequence of amino acids linked by peptide bonds. The amino acids are abbreviated as "A" alanine; "R" arginine; "N" asparagine; "D" aspartic acid; "C" cysteine; "Q" glutamine; "E" glutamic acid; "G" glycine; "H" histidine; "I" isoleucine; "L" leucine; "K" lysine; "M" methionine; "F" phenylalanine; "P" proline; "S" serine; "T" threonine; "W" tryptophan; "Y" tyrosine and "V" valine.

A "promoter" is a polynucleotide usually located within 20 to 5000 nucleotides upstream of the initiation of translation site of a gene. The "promoter" determines the first step of expression by providing a binding site to DNA polymerase to initiate the transcription of a gene. The promoter is said to be "inducible" when the initiation of transcription occurs only when a specific agent or chemical substance is presented to the cell. For instance, the GAL "promoter" from yeast is "inducible by galactose," meaning that this GAL promoter allows initiation of transcription and subsequent expression only when galactose is presented to yeast cells.

A "recombinant" polynucleotide is a novel polynucleotide sequence formed in vitro through the ligation of two DNA molecules.

"Transformation" means the directed modification of the genome of a cell by external application of a polynucleotide, for instance, a construct. The inserted polynucleotide may or may not integrate with the host cell chromosome. For example, in bacteria, the inserted polynucleotide usually does not integrate with the bacterial genome and might replicate autonomously. In plants, the inserted polynucleotide integrates with the plant chromosome and replicates together with the plant chromatin.

A "transgenic" organism is the organism that was transformed with an external polynucleotide. The "transgenic" organism encompasses all descendants, hybrids and crosses thereof, whether reproduced sexually or asexually and which continue to harbor the foreign polynucleotide.

A "vector" is a polynucleotide that is able to replicate autonomously in a host cell and is able to accept other polynucleotides. For autonomous replication, the vector contains an "origin of replication." The vector usually contains a "selectable marker" that confers the host cell resistance to certain environment and growth conditions. For instance, a vector that is used to transform bacteria usually contains a certain antibiotic "selectable marker" which confers the transformed bacteria resistance to such antibiotic.

In one aspect, the invention provides isolated PsAFB2 and PsAFB6 polynucleotides and PsAFB2 and PsAFB6 polypeptides. PsAFB2 and PsAFB6 polynucleotides include, without limitation (1) single- or double-stranded DNA, such as cDNA or genomic DNA including sense and antisense strands; and (2) RNA, such as mRNA. PsAFB2 and PsAFB6 polynucleotides include at least a coding sequence which codes for the amino acid sequence of the specified polypeptide, but may also include 5' and 3' untranslated regions and transcriptional regulatory elements such as promoters and enhancers found upstream or downstream from the transcribed region.

In one embodiment, the invention provides a PsAFB2 polynucleotide which is a cDNA comprising the nucleotide sequence depicted in SEQ ID NO: 1, and which was isolated from *Pisum sativum*. The cDNA comprises a coding region of 1716 base pairs. The auxin receptor encoded by the coding region (designated as AFB2, SEQ ID NO: 2) is a 571 amino acid polypeptide.

In one embodiment, the invention provides a PsAFB6 polynucleotide which is a cDNA comprising the nucleotide sequence depicted in SEQ ID NO: 3, and which was isolated from *Pisum sativum*. The cDNA comprises a coding region of 1725 base pairs. The auxin receptor encoded by the coding region (designated as AFB6A, SEQ ID NO: 4) is a 574 amino acid polypeptide.

Those skilled in the art will recognize that the degeneracy of the genetic code allows for a plurality of polynucleotides to encode for identical polypeptides. Accordingly, the invention includes polynucleotides of SEQ ID NOS: 1 and 3, and variants of polynucleotides encoding polypeptides of SEQ ID NOS: 2 and 4. In one embodiment, polynucleotides having at least 85%, at least 90%, at least 95%, at least 96%, at least 97%, at least 98%, or at least 99% sequence identity to the nucleotide sequences depicted in SEQ ID NO: 1 and SEQ ID NO: 3 are included in the invention. Methods for isolation of such polynucleotides are well known in the art (Ausubel et al., 1995).

In one embodiment, the invention provides isolated polynucleotides which encode auxin receptors having amino acid sequences having at least 85%, at least 90%, at least 95%, at least 96%, at least 97%, at least 98%, or at least 99% sequence identity to the amino acid sequences depicted in SEQ ID NO: 2 and SEQ ID NO: 4.

In one embodiment, the invention provides isolated polynucleotides which encode auxin receptors having amino acid sequences having a length of at least 300, at least 400 or at least 500 contiguous residues of the amino acid sequence depicted in SEQ ID NO: 2. In one embodiment, the invention provides isolated polynucleotides which encode auxin receptors having amino acid sequences having a length of at least 300, at least 400 or at least 500 contiguous residues of the amino acid sequence depicted in SEQ ID NO: 4.

The above described polynucleotides of the invention may be used to express polypeptides in recombinantly engineered cells including, for example, bacterial, yeast, fungal, mammalian or plant cells. In one embodiment, the invention provides polynucleotide constructs, vectors and cells comprising PsAFB2 or PsAFB6 polynucleotides, or both. Those skilled in the art are knowledgeable in the numerous systems available for expression of a polynucleotide. All systems employ a similar approach, whereby an expression construct is assembled to include the protein coding sequence of interest and control sequences such as promoters, enhancers, and terminators, with signal sequences and selectable markers included if desired. Briefly, the expression of isolated polynucleotides encoding polypeptides is typically achieved by operably linking, for example, the DNA or cDNA to a constitutive or inducible promoter, followed by incorporation into an expression vector. The vectors can be suitable for replication and integration in either prokaryotes or eukaryotes. Typical expression vectors include transcription and translation terminators, initiation sequences, and promoters useful for regulation of the expression of the DNA. High level expression of a cloned gene is obtained by constructing expression vectors which contain a strong promoter to direct transcription, a ribosome binding site for translational initiation, and a transcription/translation terminator. Vectors may further comprise transit and targeting sequences, selectable markers, enhancers or operators. Means for preparing vectors are well known in the art. Typical vectors useful for expression of polynucleotides in plants include for example, vectors derived from the Ti plasmid of *Agrobacterium tumefaciens* and the pCaM-VCN transfer control vector. Promoters suitable for plant cells include for example, the nopaline synthase, octopine synthase, and mannopine synthase promoters, and the caulimovirus promoters.

Those skilled in the art will appreciate that modifications (i.e., amino acid substitutions, additions, deletions and post-translational modifications) can be made to a polypeptide of the invention without eliminating or diminishing its biological activity. Conservative amino acid substitutions (i.e., substitution of one amino acid for another amino acid of similar size, charge, polarity and conformation) or substitution of one amino acid for another within the same group (i.e., nonpolar group, polar group, positively charged group, negatively charged group) are unlikely to alter protein function adversely. Some modifications may be made to facilitate the cloning, expression or purification. Variant PsAFB2 and PsAFB6 polypeptides may be obtained by mutagenesis of the polynucleotides depicted in SEQ ID NOS: 1 and 3 using techniques known in the art including, for example, oligonucleotide-directed mutagenesis, region-specific mutagenesis, linker-scanning mutagenesis, and site-directed mutagenesis by PCR (Ausubel et al., 1995).

Various methods for transformation or transfection of cells are available. For prokaryotes, lower eukaryotes and animal cells, such methods include for example, calcium phosphate precipitation, fusion of the recipient cells with bacterial protoplasts containing the DNA, treatment of the recipient cells with liposomes containing the DNA, DEAE dextran, electroporation, biolistics and microinjection. The transfected cells are cultured, and the produced AFB2 and AFB6 polypeptides may be isolated and purified from the cells using standard techniques known in the art. Various industrial strains of microorganisms including for example, *Aspergillus, Pichia pastoris, Saccharomyces cerevisiae, E. coli, Bacillus subtilis* may be used to produce AFB2 and AFB6 polypeptides.

Methods for transformation of plant cells include for example, electroporation, PEG poration, particle bombardment, *Agrobacterium tumefaciens*- or *Agrobacterium rhizogenes*-mediated transformation, and microinjection. The transformed plant cells, seeds, callus, embryos, microspore-derived embryos, microspores, organs or explants are cultured or cultivated using standard plant tissue culture techniques and growth media to regenerate a whole transgenic plant which possesses the transformed genotype. Transgenic plants may pass polynucleotides encoding PsAFB2 or PsAFB6 polypeptides to their progeny, or can be further crossbred with other species. Accordingly, in one embodiment, the invention provides methods for producing transgenic plants, plant cells, callus, seeds, plant embryos, microspore-derived embryos, and microspores comprising PsAFB2 or PsAFB6 polynucleotides.

In one embodiment, the invention provides transgenic plants, plant cells, callus, seeds, plant embryos, microspore-derived embryos, and microspores comprising PsAFB2 or PsAFB6 polynucleotides. Plant species of interest for transformation include, without limitation, flax, canola, oats, wheat, triticale, barley, corn, and legume plants including soybean and pea.

The auxin receptor polynucleotides, polypeptides, and methods of the invention have agricultural applications since plants with increased abiotic stress tolerance may be developed. Altered auxin receptor transcript or protein abundance may lead to a low rate of seed or fruit abortion under abiotic stress conditions. Plants may be modified to underexpress PsAFB6 using molecular techniques such as RNAi technology or by a non-genetically modified organism method such as targeting-induced local lesion in genomes (TILLING) (Trique et al., 2007).

Expression of PsAFB6 increases in the ovaries (pericarps) of emasculated fruit prior to ovary senescence and abscission, and in young ovaries following seed removal. When 4-Cl-IAA (the growth auxin in pea pericarps) is applied to deseeded ovaries, the increase in PsAFB6 mRNA abundance is prevented along with the prevention of fruit abortion. IAA (the growth inactive auxin in pea pericarp) application to deseeded ovaries does not prevent the increase in PsAFB6 mRNA abundance, nor does it prevent the abortion of deseeded fruits. Without being bound by theory, AFB6 appears to be involved in increasing ethylene sensitivity of the ovary which leads to pod abortion. Abiotic stresses may also modulate auxin receptor abundance in the seeds and ovaries, with the resultant auxin receptor population determining the fate of the developing fruit. Modulation of AFB6 (at the transcript level or protein level) may ameliorate abiotic stress symptoms in reproductive tissues in species that contain this auxin receptor clade, as further described.

Two members of the AFB family of auxin receptors were isolated from *Pisum sativum* L: PsAFB2 and PsAFB6. These two auxin receptors have not previously been described in the art. The interior regions of two *Pisum* AFB homologues were obtained via PCR amplification with the degenerate CODEHOP primers. Several successive experiments produced 13 clones of one gene with high sequence similarity to members of the AFB2/3 group of receptors, and one clone belonging to the AFB6 group of receptors. While the AFB2/3 clade is fairly ubiquitous amongst investigated plants, with many species possessing two or more members, AFB6 is restricted to fewer species, including the legumes *Pisum sativum* and *Medicago truncatula* (BAC sequence mth2-32 m30, Cannon et al., 2006).

The 5' region of PsAFB2 not amplified by the CODEHOP primers, consisting of putative coding sequence and part of the 5' UTR, was amplified in three independent clones. The 3' region of PsAFB2 not amplified by the CODEHOP primers, consisting of part of the putative coding region and 3' UTR, was also amplified in three independent clones. All 3' and 5' RACE products overlapped with the interior fragment isolated with the CODEHOP primers, and represented one unique 5' and one unique 3' sequence. The coding region of the entire PsAFB2 gene was amplified and cloned into the PCR8 vector for later transfer to expression systems, and 3 clones were sequenced end-to-end to confirm the sequence. The putative coding region of this cDNA is 1716 nucleotides long (FIGS. 6A-B), and codes for a protein with an expected length of 571 amino acids (FIGS. 13A-C).

The 5' region of PsAFB6 not amplified by the CODEHOP primers, consisting of putative coding sequence and part of the 5' UTR, was amplified in two independent clones. While both of these clones contained the same fragment of the coding region, one possessed an additional ~20 bp within the 5' UTR. The 3' region of PsAFB6 not amplified by the CODEHOP primers, consisting of part of the putative coding region and 3' UTR, was obtained in two independent clones. While both of the 3' RACE clones consisted of the same coding region and 3' UTR, one was slightly longer and contained part of the poly-A tail. All 3' and 5' RACE products overlapped with the interior fragment isolated with the CODEHOP primers. The putative coding region of this cDNA is 1725 nucleotides long (FIGS. 7A-B), and encodes a putative protein of 574 amino acids length (FIGS. 14A-D).

In silico translation of PsAFB2 and PsAFB6 and alignment with the 58 protein sequences used to generate the CODEHOP primers was used to name the two cDNAs according to standard *Pisum sativum* nomenclature. FIGS. 13A-C and 14A-B show the putative translated gene products of both PsAFB2 and PsAFB6 presented as alignments with putative and confirmed members of their respective sub-families of AFB proteins from other species of angiosperms. Domain prediction was performed with the SMART program (Schultz et al., 1998, Letunic et al., 2005), and identified C-terminal F-boxes and multiple LRRs (Table 1).

There were no major differences in the position or length of these putative domains between the putative AFB gene products isolated here and their corresponding homologues. The structure of the putative gene products of PsAFB2 and PsAFB6 follows that of other AFB proteins, with an F-box domain near the C-terminal and a series of leucine rich repeats towards the mid and N-terminal portions of the protein. Non-redundant domains with significant E-values for PSAFB2 and PSAFB6 are listed in Table 1. The F-box domain of PSAFB6 did not pass the threshold E-value under default settings, but is located between residues 7 and 55 (E-value=1.20e+00). It is included in Table 1 because of the high sequence similarity it shares to other AFB6 members. While this software identified corresponding numbers of LRR in PSAFB6 and ATTir1, it identified two additional LRRs in PSAFB2, which are expansions of an already identified LRR found in both other proteins.

The roles of AFB2 and AFB6 in seed and fruit development were examined through transcription profiling with qRT-PCR. Reaction efficiency for the AFB amplicons was determined for use in the calculation of relative transcript abundance. The efficiency of the PsAFB6 amplicon was somewhat higher than that of the PsAFB2 amplicon (Table 2), and in both cases the calculated regressions had $r^2$ values greater than 0.990.

TABLE 2

Reaction efficiency of PsAFB2 and PsAFB6 qRT-PCR Assays

| Amplicon | Efficiency | $r^2$ |
|---|---|---|
| PsAFB2 | 93.6% | 0.999 |
| PsAFB6 | 99.1 | 0.994 |

The transcript abundance profiles suggest that initial seed development is more sensitive to auxin than later seed developmental stages. In whole seeds, transcript abundance of both PsAFB2 (FIGS. 8 and 9A) and PsAFB6 (FIGS. 10 and 9B) was highest immediately following fertilization (0 DAA), and gradually decreased to 20 DAA, a 12.4-fold and 3.2-fold decrease over this developmental period, respectively.

Figure 8:
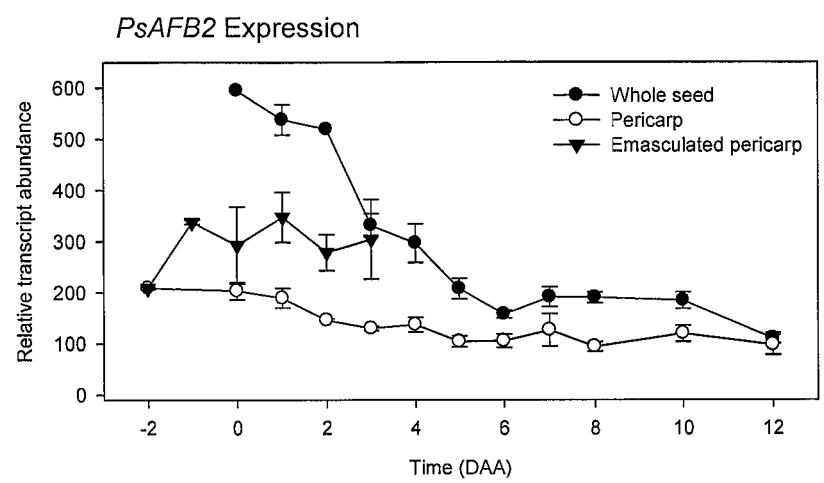
FIG. 8 is a graph of the steady-state transcript abundance of PsAFB2 during early fruit development in whole pericarps, seeds, and pericarps from flowers emasculated at −2 DAA. Data are expressed as mean±standard error. Where standard error is too small, error bars may be obscured by symbols. Samples are representative of between 2 and 3 independent replicates, except for 0 DAA whole seed (n=1) and 6 DAA pericarp (n=4).
Figure 9:
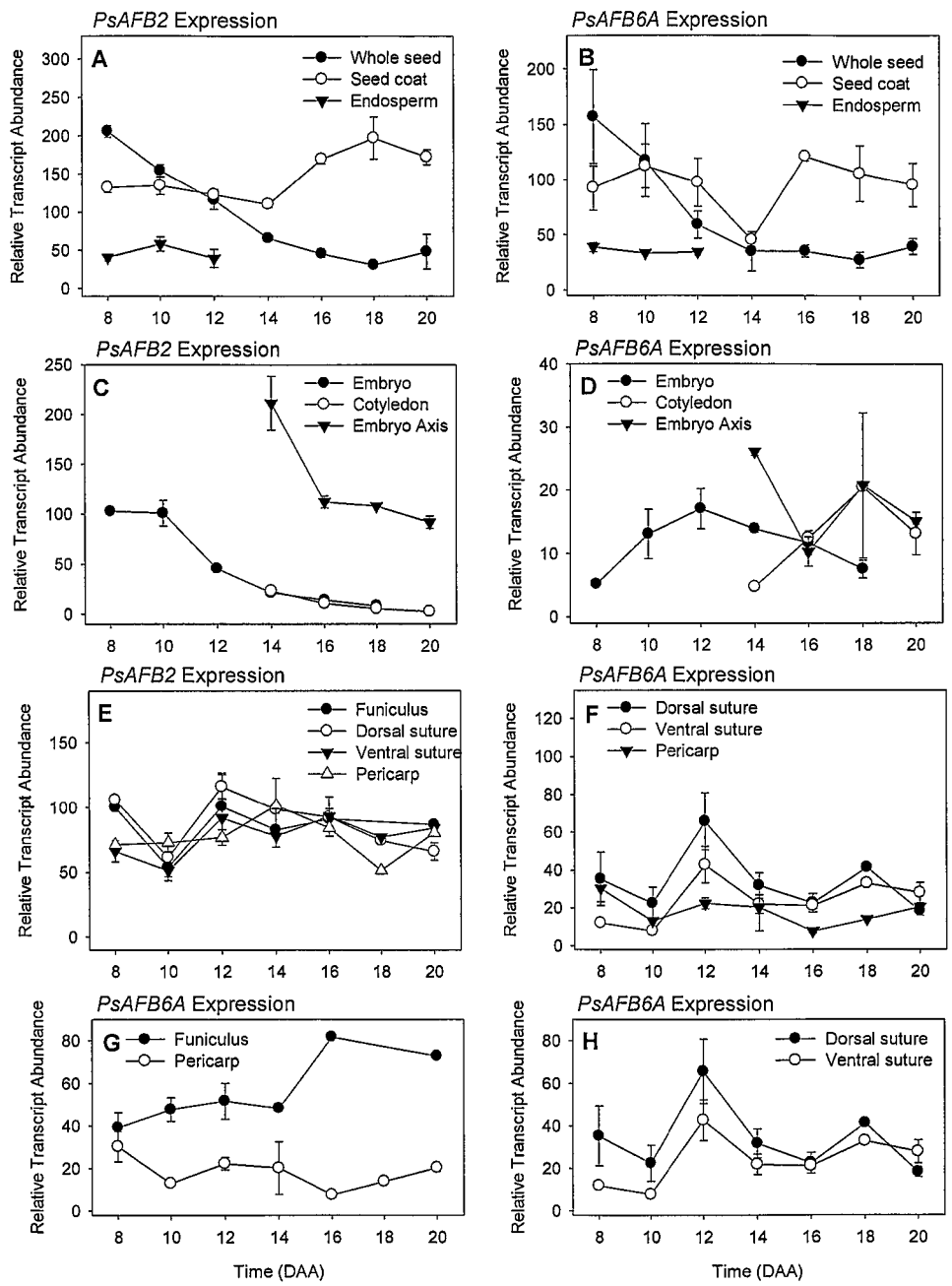
FIGS. 9A-H are graphs of the transcript abundances of the putative auxin receptor genes PsAFB2 and PsAFB6 in seed and fruit tissues during development. Data are expressed as mean±standard error. Where standard error is too small, error bars may be obscured by symbols. Samples are representative of between 2 and 5 independent samples, except for all vascular suture tissues at 18 DAA, pericarp at 8 DAA, and embryo at 8 DAA, for which n=1, and whole seed at 16 DAA, for which n=6. All samples are normalized to the same scale, allowing comparison between all tissues of the same gene.

Whole seed PsAFB2 mRNA levels decreased substantially between 2 and 6 DAA, and remained low through 12 DAA. Pericarp PsAFB2 transcript abundance was higher from −2 to 1 DAA, then decreased by 5 DAA and remained at this lower level until 20 DAA (FIGS. 8 and 9E). In pericarps from non-pollinated ovaries (flowers emasculated at −2 DAA), PsAFB2 transcript abundance was elevated from −1 DAA to 3 DAA in comparison to pericarps from pollinated ovaries (FIG. 8).

Figure 10:
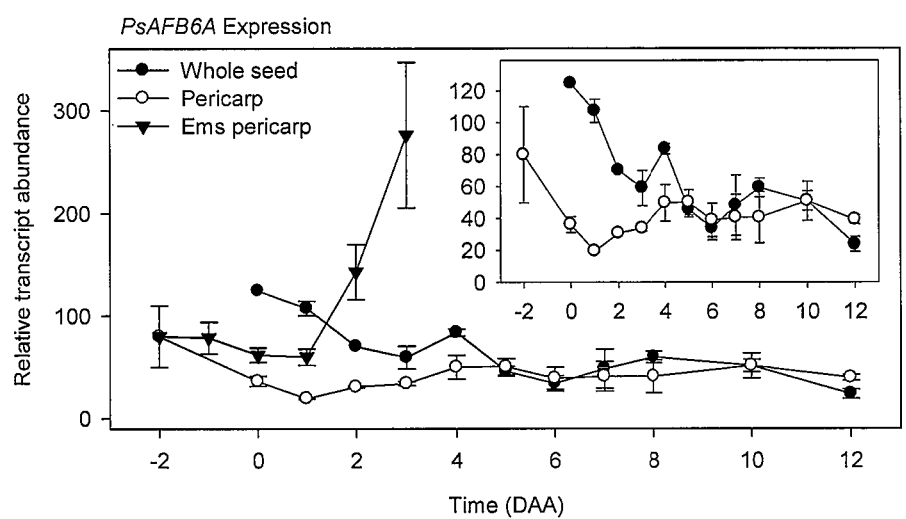
FIG. 10 is a graph of the steady-state transcript abundance of PsAFB6 during early fruit development in whole pericarp, seeds, and pericarp from flowers emasculated at −2 DAA (Ems peri). Data are expressed as mean±standard error. Where standard error is too small, error bars may be obscured by symbols. Samples are representative of between 2 and 3 independent replicates, except for 0 DAA whole seed (n=1) and 6 DAA pericarp (n=4).

Trends in transcript abundance of PsAFB6 were similar to those of PsAFB2 in seeds and pericarps from −2 to 12 DAA. Whole seed PsAFB6 transcript abundance was higher immediately after fertilization (FIG. 10) and then decreased until 20 DAA (FIGS. 10 and 9B). Pericarp PsAFB6 transcript levels were elevated prior to pollination (−2 DAA), then decreased 4.1-fold by 1 DAA, after pollination and fertilization of the ovary (FIG. 10). From 2 to 20 DAA, pericarp PsAFB6 transcript levels were relatively constant (FIGS. 10

TABLE 1

Predicted domains of PSAFB2 and PSAFB6 from SMART algorithm. LRR = leucine rich repeat. To confirm the validity of this approach, ATTIR1, for which experimental confirmation of these domains and crystal structures are available, was also analyzed.

| PSAFB2 | | | | PSAFB6 | | | | ATTIR1 | | | |
|---|---|---|---|---|---|---|---|---|---|---|---|
| Domain | Start | End | E-value | Domain | Start | End | E-value | Domain | Start | End | E-value |
| F-box | 4 | 45 | 6.97e−04 | F-box | 7 | 55 | 1.20e+00 | F-box | 9 | 50 | 7.18e−06 |
| LRR | 99 | 123 | 5.08e+02 | LRR | 107 | 131 | 2.99e+02 | LRR | 129 | 154 | 1.03e+02 |
| LRR | 124 | 149 | 8.67e+01 | LRR | 132 | 157 | 2.67e+01 | LRR | 155 | 192 | 4.38e+02 |
| LRR | 283 | 308 | 1.92e+02 | | | | | | | | |
| LRR | 309 | 332 | 8.93e+01 | LRR | 316 | 339 | 7.71e+01 | LRR | 313 | 336 | 4.01e+02 |
| LRR | 333 | 364 | 6.06e+02 | | | | | | | | |
| LRR | 365 | 389 | 3.47e+00 | LRR | 374 | 398 | 3.00e+01 | LRR | 371 | 395 | 8.09e−01 |
| LRR | 425 | 448 | 1.61e+02 | LRR | 434 | 457 | 4.27e+01 | LRR | 431 | 454 | 1.71e+02 |
| LRR | 474 | 499 | 5.57e+01 | LRR | 483 | 507 | 2.50e+02 | LRR | 480 | 504 | 2.91e+01 |

While the structural features of the AFB group of F-box proteins are very highly conserved, the C-terminals of members of the AFB6 clade are somewhat variable in length (FIGS. 14A-B). The major structural features of the AFB proteins are retained.

and 9F). PsAFB6 mRNA abundance was slightly elevated in emasculated pericarps within 24 hours of emasculation (FIG. 10), as was the case with PsAFB2. While PsAFB2 mRNA levels remained constant after this initial increase, PsAFB6 abundance markedly increased between 1 and 3

DAA in emasculated pericarps (FIG. 10), indicating that pericarp transcript levels of these two genes are regulated differentially.

Steady-state transcript abundance of both PsAFB genes was maintained at relatively low levels in the endosperm from 8 to 12 DAA (FIGS. 9A, B). In whole seeds, PsAFB2 (FIG. 8) and PsAFB6 (FIG. 10) transcript levels were higher earlier in development and decreased over time; however, mRNA levels of these two genes varied in a tissue-specific manner over development from 8 to 20 DAA.

In early development (8 DAA), PsAFB2 mRNA was present at approximately equal levels in the seed coat and embryo (FIGS. 9A, C). While embryo PsAFB2 transcript abundance decreased from 10 DAA onwards (FIG. 9C), seed coat PsAFB2 mRNA levels were maintained during this period, and slightly increased between 14 and 16 DAA (FIG. 9A). Within the embryo, PsAFB2 mRNA localized primarily to the embryo axis from 14 to 20 DAA, as steady-state abundance was significantly higher in this tissue than in cotyledon or whole embryo samples (FIG. 9C). Steady-state transcript abundance of PsAFB2 was similar in the tissues of the pericarp (dorsal and ventral vascular trace sutures and pericarp wall tissue), and pericarp PsAFB2 transcript abundance remained relatively constant from 8 to 20 DAA (FIG. 9E). PsAFB2 transcript abundance in the funiculus was also similar to that of the pericarp tissues (FIG. 9E).

While PsAFB2 mRNA levels were approximately equal in the early (8 DAA) seed coat and embryo, PsAFB6 transcript abundance was 17.9-fold greater in the seed coat than in the embryo at this time (FIGS. 9B, D). PsAFB6 mRNA was maintained at relatively constant levels in the seed coat between 8 and 20 DAA (FIG. 9B). Steady-state PsAFB6 mRNA abundance was low in the embryo at 8 DAA, then increased between 8 and 12 DAA before decreasing between 12 and 18 DAA (FIG. 9D). While PsAFB6 transcript abundance was 5.5-fold higher in the embryo axis than in the cotyledons at 14 DAA, by 16 DAA mRNA levels in these tissues were equivalent and remained so until 20 DAA (FIG. 9D).

In contrast to PsAFB2 transcript levels, PsAFB6 steady-state mRNA abundance varied in a tissue-specific manner between 8 and 20 DAA within the pericarp and funiculus tissues. PsAFB6 transcript levels were generally higher in the funiculus than in any of the pericarp (FIGS. 10F, G) or seed (FIGS. 9D, G) tissues. Additionally, funiculus PsAFB6 mRNA levels increased as the fruit matured (FIG. 9G). While PsAFB2 mRNA was present at approximately equal levels in the three pericarp tissues (FIG. 9E), PsAFB6 transcript abundance was higher in the two vascular sutures than in the pericarp wall (FIG. 9F). Furthermore, PsAFB6 transcript abundance was generally higher in the dorsal than in the ventral vascular suture of the pericarp (seeds are attached to the pericarp via the funiculus at the ventral suture; FIG. 9H).

Figure 11:
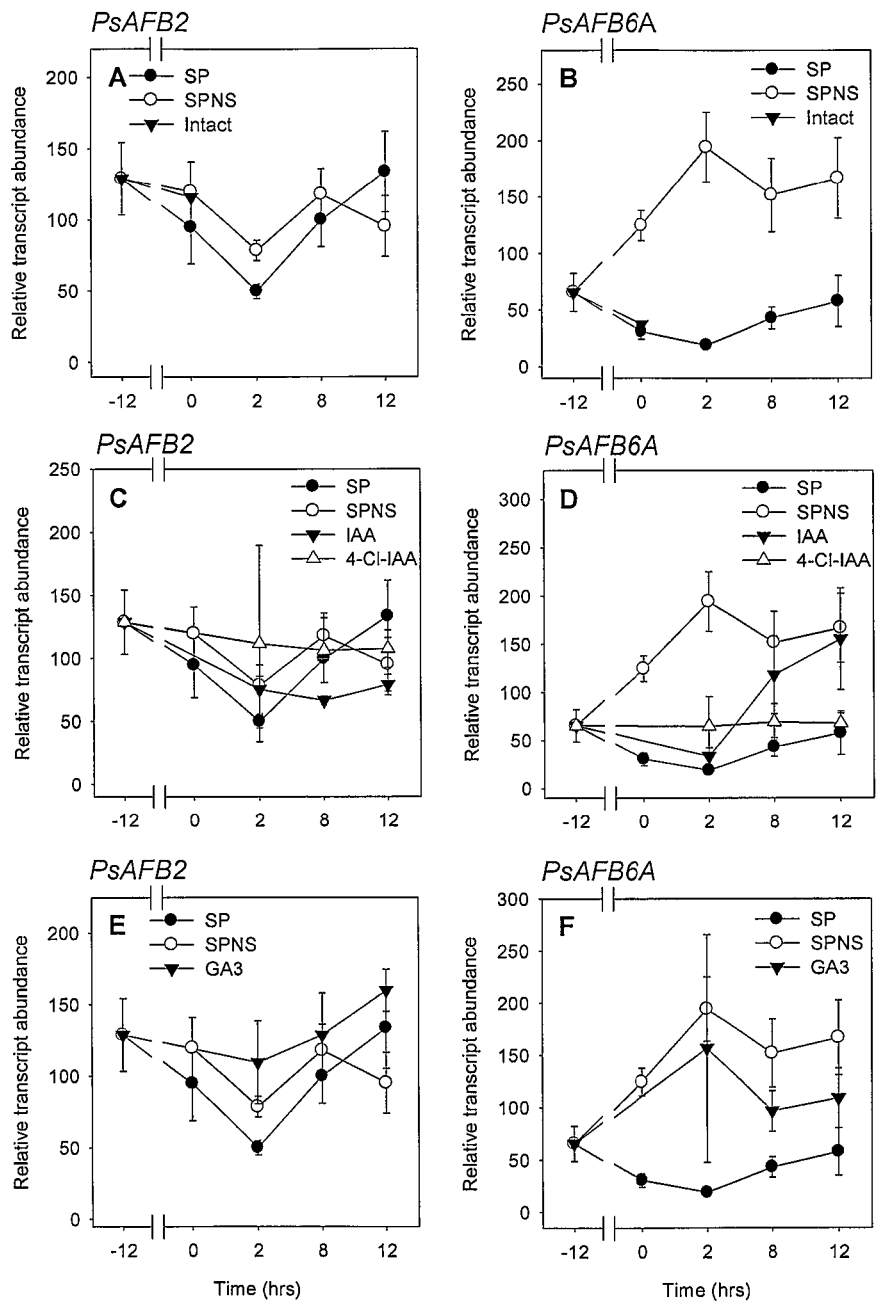
FIGS. 11A-F are graphs of the steady-state mRNA abundances of PsAFB2 (A, C, E) and PsAFB6 (B, D, F) genes in pericarps with and without seeds, and deseeded pericarps treated with hormones. Two DAA pericarps were left intact, split (SP), split and deseeded (SPNS), or split and deseeded then treated with 50 μM IAA (C, D), 4-Cl-IAA (C, D) or $GA_3$ (E, F). Hormones were applied to pericarps 12 hours after deseeding and the effects of hormone application on transcript abundance were monitored 2, 8 and 12 h after application (14, 20, and 24 h after deseeding). Data are presented as mean±standard error, n=2 to 4 at each point.

The response of steady-state mRNA levels of these genes to auxins and gibberellins was evaluated to identify possible hormone regulation of auxin sensitivity via the modulation of AFB gene transcript abundance. PsAFB2 transcript abundance was approximately equal in pericarps with (SP) or without seeds (SPNS; FIG. 11A). Treatment of deseeded pericarps with 4-Cl-IAA, IAA, or $GA_3$ did not significantly affect steady-state PsAFB2 transcript abundance (FIGS. 11A, C, E) in this tissue. These data suggest that PsAFB2 mRNA levels are largely unregulated by the presence of seeds, pericarp splitting, or the addition of IAA, 4-Cl-IAA, or $GA_3$.

PsAFB6 transcript abundance was similar in both split-pericarps with seeds (SP) and intact controls, indicating that the split-pericarp procedure did not influence steady-state abundance of this gene (FIG. 11B). Removal of seeds markedly increased PsAFB6 transcript abundance in the pericarp at all times assessed (12 to 24 hours after seed removal; FIG. 11B). Two hours after IAA was applied to deseeded pericarps, pericarp PsAFB6 mRNA abundance was similar to that of the SP control (FIG. 11D). However, 8 hours after IAA application, pericarp PsAFB6 transcript abundance increased to that observed in the SPNS pericarps, and remained at this elevated level until 12 hours after hormone treatment (FIG. 11D). In contrast to the transitory reduction of PsAFB6 steady-state mRNA abundance by IAA in deseeded pericarps, 4-Cl-IAA treatment reduced PsAFB6 mRNA abundance to levels similar to those found in SP controls throughout the developmental time course (FIG. 11D). $GA_3$ was found to have no effect on PsAFB6 steady-state transcript abundance in these experiments (FIG. 11F).

The roles of the PsAFB2 and PsAFB6 genes in fruit and seed development were elucidated by examination of the correlation between endogenous IAA and 4-Cl-IAA and auxin receptor transcript abundance in seed tissues. Embryo IAA levels were initially high at 10 DAA, and then decreased with a small peak in levels observed at 16 DAA (Table 3A). At 18 DAA, levels of IAA were 8.4-fold (based on ng $gFw^{-1}$) higher in the embryo axis than in the cotyledons. Like the embryo, seed coat IAA was also highest at 10 DAA and decreased as the seed developed.

The tissue localization and relative concentrations of 4-Cl-IAA were significantly different to those of IAA. Levels of 4-Cl-IAA were significantly higher than that of IAA in both the seed coat and embryonic tissues from 10 to 18 DAA. Embryo 4-Cl-IAA levels increased markedly between 12 and 14 DAA, during which time the endosperm is completely absorbed by the embryo as it expands to fill the seed cavity. Subsequently, embryo 4-Cl-IAA levels decreased (between 16 and 18 DAA). Like IAA, the concentration of 4-Cl-IAA was higher in the embryo axis than that in the cotyledons at 18 DAA. 4-Cl-IAA was very abundant in the seed coat at 10 DAA, and decreased as the seed developed.

The concentrations of both auxins increased between 10 and 12 DAA in the endosperm, when it reached maximum volume (Table 3B). In contrast to the other seed tissues, where 4-Cl-IAA was much more abundant than IAA, levels of IAA and 4-Cl-IAA were comparable in this tissue (Table 3B).

TABLE 3

| IAA and 4-Cl-IAA content in developing pea seed tissues from 10 to 18 DAA. | | | | | |
|---|---|---|---|---|---|
| | 10 DAA | 12 DAA | 14 DAA | 16 DAA | 18 DAA |
| A | | | | | |
| Embryo IAA | 86.22 | 28.55 ± 2.42 | 19.80 ± 1.83 | 36.35 ± 8.46 | 14.56 ± 2.36 |
| Cotyledon IAA | — | — | — | — | 8.46 ± 1.06 |
| Embryo Axis IAA | — | — | — | — | 71.20 |
| Seed Coat IAA | 54.95 ± 10.80 | 20.05 ± 1.34 | 8.47 ± 1.15 | 10.05 ± 1.96 | 5.71 ± 1.04 |

TABLE 3-continued

IAA and 4-Cl-IAA content in developing pea seed tissues from 10 to 18 DAA.

|  | 10 DAA | 12 DAA | 14 DAA | 16 DAA | 18 DAA |
| --- | --- | --- | --- | --- | --- |
| Embryo 4-Cl-IAA | 141.68 | 102.55 | 661.68 ± 261.71 | 653.97 | 137.7 ± 49.35 |
| Cotyledon 4-Cl-IAA | — | — | — | — | 84.18 ± 6.44 |
| Embryo Axis 4-Cl-IAA | — | — | — | — | 265.03 |
| Seed Coat 4-Cl-IAA | 840.99 | 486.27 | 128.41 ± 21.25 | 295.22 | 196.08 |
|  |  | B |  |  |  |
| Endosperm IAA | 89.35 ± 19.34 | 244.04 ± 11.04 | — | — | — |
| Endosperm 4-Cl-IAA | 148.67 ± 33.38 | 238.95 | — | — | — |

Results are presented as means of two independent samples ± standard error
(n.d. = not detected, although internal standard added at tissue homogenization was recovered), with a few exceptions where n = 1.
Results are expressed as ng gFw$^{-1}$ (A) for solid tissues and ng mL$^{-1}$ (B) for liquid endosperm In the seed coat, transcript levels of both PsAFB2 and PsAFB6 did not markedly change from 8 to 20 DAA (FIGS. 9A, B). During this period however, levels of free IAA and 4Cl-IAA in the seed coat changed significantly: seed coat IAA decreased 9.6-fold and seed coat 4-Cl-IAA decreased 4.3-fold between 10 and 18 DAA (Table 3). Therefore, without restriction to a theory, we believe that changes in free auxin levels may be a primary mechanism for regulating auxin-related growth and development in the seed coat during this developmental period (10 to 20 DAA).

In the embryo, PsAFB2 transcript abundance was higher earlier in development and decreased with embryo maturation (FIG. 10C). PsAFB2 transcript levels were also higher in the embryo axis than in the cotyledons from 14 to 20 DAA (FIGS. 9C, D). Experiments using end-point RT-PCR and promoter::GUS fusion constructs have demonstrated that the AtAFB2 and AtAFB3 genes are expressed in developing embryos, floral organs, and siliques in *Arabidopsis* (Dharmasiri et al., 2005b). Auxin signalling is vital to early embryo patterning (Jenik et al., 2007), and mutation of the AFB genes prevents normal embryo formation (Dharmasiri et al., 2005b). The expression studies described herein are consistent with the roles of AFB2/3 as a necessary regulator of embryo development. The PsAFB2 expression profiles suggest that higher expression of PsAFB2 occurs earlier in development (FIG. 9C) when the embryo tissues undergo rapid growth, during which time developmental patterning and cell division are important processes. In the liquid endosperm, a non-cellular multinucleate tissue with no internal spatial patterning, transcript abundance of PsAFB2 was lower than in either the seed coat or the embryo from 8 and 12 DAA (FIGS. 9A, C).

In contrast to PsAFB2 expression, PsAFB6 transcript abundance was lower in the embryo than in the endosperm from 8 to 12 DAA (FIGS. 10B, D). The embryo PsAFB6 transcript profile also differed from that of PsAFB2 in that higher transcript abundance was observed later (10 to 14 DAA) during development, and higher PsAFB6 levels were observed in the embryo axis (compared to the cotyledons) only at 14 DAA (FIG. 10D). These data suggest that transcript abundance of the auxin receptor PsAFB6 is regulated differently than that of PsAFB2 in these seed tissues.

Endogenous 4-Cl-IAA levels were higher than those of IAA in the embryo and seed coat at all development stages studied (10 to 18 DAA; Table 3A), however the levels of these endogenous auxins were approximately equal in the 10 to 12 DAA endosperm (Table 3B). The comparatively high abundance of 4-Cl-IAA in the embryo and seed coat indicates that this hormone serves a major role in auxin regulated processes in these tissues during this phase of seed development.

Embryo IAA abundance in general decreased over seed development (10 to 18 DAA) with a small peak in levels observed at 16 DAA (Table 3A). In contrast, embryo 4-Cl-IAA levels peaked at 14 to 16 DAA, and at levels 18.0- to 33.4-fold greater than those of IAA, concomitant with the transition of the embryo from the pre-storage phase (characterized primarily by growth and development) to the reserve accumulation phase (characterized by nutrient storage, although embryo growth still occurs). These endogenous auxin profiles indicate that the specific roles of 4-Cl-IAA and IAA in the embryo likely differ during the stages of growth studied, and that increases in embryo 4-Cl-IAA abundance may be involved in the regulation of embryo processes during the transition from the pre-storage to storage phase.

Seed coat IAA abundance decreased from 9.6-fold from 10 to 18 DAA (Table 3A), similar to the IAA profile of the developing embryo during this time. Seed coat 4-Cl-IAA levels were highest earlier in development (10 DAA) then decreased 6.5-fold by 14 DAA before increasing somewhat by 16 to 18 DAA. In contrast to the embryo, in which 4-Cl-IAA accumulates as the seed enters the storage phase at approximately 14 to 18 DAA, 4-Cl-IAA accumulates earlier in seed coat development and is relatively low at 14 DAA. While final seed size in pea is related to cotyledon cell number (Davies, 1975), the seed coat may also exert influences on seed growth, both as a mechanical limiter to embryo expansion and as a source of regulatory compounds. The high abundance of 4-Cl-IAA in the seed coat from 10 to 12 DAA may be important for regulating seed coat growth (seed coat fresh weight and ground parenchyma cell size increase greatly between 10 and 12 DAA; data not shown), and/or 4-Cl-IAA may be transported to either the pericarp or embryo to regulate developmental processes in those tissues.

In the endosperm, both IAA and 4-Cl-IAA levels increase from 10 to 12 DAA (Table 3B) as the endosperm reaches its maximum volume. Whereas in the embryo and seed coat 4-Cl-IAA was more abundant than IAA (Table 3A), both hormones are found at similar concentrations in the liquid endosperm (Table 3B). In *Zea mays*, the liquid endosperm produces large quantities of IAA, and early increases in liquid endosperm IAA production promote increases in chromosome endoreduplication (Lur and Setter, 1993). While the development of the endosperm in pea differs significantly from that of maize (pea endosperm is liquid, non-cellular, and absorbed by the embryo long before maturity, while maize endosperm is cellular and present in the mature seed), it is also characterized by increases in ploidy: endosperm nuclei are normally 3n, but 6n and even 12n nuclei are observed (Kapoor, 1966), and the relatively high levels of IAA may promote similar processes in pea endosperm.

Pollination and fertilization events (−2 to 1 DAA) did not affect pericarp transcript abundance of PsAFB2 (FIG. 8), but reduced transcript abundance of PsAFB6 (FIG. 10). The emasculation of flowers at −2 DAA increased transcript abundance of both PsAFB2 (FIG. 8) and PsAFB6 (FIG. 10) by anthesis (0 DAA), and additionally produced a marked increase in PsAFB6, but not PsAFB2, transcript levels after 1 DAA (FIG. 10). Between 1 and 3 DAA, transcript abundance of PsAFB6 in emasculated pericarps increased 4.6-fold, while levels in pollinated pericarps increased only 1.7-fold, and at 3 DAA transcript levels of PsAFB6 were 8.2-fold greater in non-pollinated pericarps than in pollinated pericarps (FIG. 10). By 4 DAA, non-pollinated pea fruit will normally become flaccid and subsequently senesce (Ozga et al., 2003). Therefore, in pea, the presence of fertilized seeds is required for pericarp growth (Eeuwens and Schwabe, 1975; Ozga et al., 1992), and appears to repress the expression of the auxin receptor PsAFB6 in the pericarp.

To further confirm that seeds are required for repression of pericarp PsAFB6 transcript levels, the mRNA abundance of both PsAFB genes in pericarps with and without seeds post-anthesis was monitored. Seed removal from 2 DAA fruits increased the transcript abundance of pericarp PsAFB6 (FIG. 11B), but not PsAFB2 (FIG. 11A), confirming trends observed in non-pollinated pericarps.

Application of 4-Cl-IAA, but not IAA, to 2 DAA deseeded pericarps can mimic the presence of the seeds with respect to stimulation of pericarp growth (Reinecke et al., 1995). Bioactive GAs, $GA_1$ and $GA_3$ also stimulate deseeded pericarp growth (Ozga and Reinecke, 1999). To test if the auxin 4-Cl-IAA can specifically mimic the effect of the seeds on PsAFB6 transcript abundance, and determine if bioactive GAs also can affect the expression of these auxin receptor genes, transcript abundance was monitored in deseeded pericarps treated with 4-Cl-IAA, IAA and $GA_3$. Pericarp PsAFB6 transcript levels were initially reduced by both 4-Cl-IAA and IAA treatment (2 h after hormone application; FIG. 11D). However, by 8 hours after hormone application, PsAFB6 transcript levels were significantly greater in the IAA-treated deseeded pericarps than the pericarp with seeds (SP) and transcript levels remained elevated through the 12 hour time point (FIG. 11D). In contrast, 4-Cl-IAA treated deseeded pericarps had lower levels of PsAFB6 transcript throughout the 12 hour period analyzed (FIG. 11D). Bioactive $GA_3$ had no effect on pericarp PsAFB6 transcript abundance (FIG. 12F). Pericarp PsAFB2 transcript abundance was not affected by seed removal (FIG. 12A) or treatment with IAA, 4-Cl-IAA (FIG. 11C), or $GA_3$ (FIG. 11E). These data indicate that, in addition to stimulating pericarp growth (Reinecke et al., 1999) and GA biosynthesis (Ozga et al., 2009), 4-Cl-IAA can mimic the presence of seeds in the repression of transcript levels of the putative auxin receptor PsAFB6 in the pericarp.

In pea, seed-derived 4-Cl-IAA promotes pericarp growth through several mechanisms. In addition to promoting pericarp GA biosynthesis (Ozga et al., 2002) and inhibiting pericarp GA catabolism (Ozga et al., 2009), 4-Cl-IAA also inhibits ethylene response (Johnstone et al., 2005). The application of IAA to deseeded pericarp further decreases growth as measured by fresh weight, through the stimulation of ethylene biosynthesis (Johnstone et al., 2005). While both IAA and 4-Cl-IAA stimulated pericarp ethylene evolution, 4-Cl-IAA additionally inhibited ethylene response (Johnstone et al., 2005). The ability of 4-Cl-IAA to inhibit pericarp ethylene response may involve the repression of the auxin receptor PsAFB6, the gene product of which could serve as a promoter of ethylene sensitivity or response via SCF-mediated degradation of specific Aux/IAA regulators. Orzáez et al. (1999) observed that the putative ethylene receptor PsERS was upregulated in emasculated pericarps compared to pericarps with fertilized seeds. Orzáez et al. (1999) also found that both ethylene levels and ACC oxidase transcript (codes for a key enzyme in the ethylene biosynthesis pathway) were higher in emasculated pericarps between −2 and 3 DAA, suggesting a role for ethylene in non-pollinated pea fruit senescence.

The role of 4-Cl-IAA and viable seeds in promoting pericarp GA biosynthesis and growth has been well-documented, and the seed signal(s) is required for normal pericarp development (Ozga and Brenner, 1992, Ozga et al., 2003, Ozga et al., 2009). In the absence of these signals, pericarp senescence occurs. Without restriction to a theory, we believe that the localized upregulation of PsAFB6 is a mechanism to ensure that pericarp senescence does not proceed in the presence of viable seeds. Seed-derived 4-Cl-IAA serves to limit PsAFB6 gene expression, while in the absence of this signal (absence of ovule fertilization) PsAFB6 transcript levels increase. In the case of partial ovule fertilization within the fruit, the upregulation of pericarp PsAFB6 would heighten the local pericarp tissues sensitivity to ethylene, and reduce pericarp growth locally around non-fertilized ovules as local pericarp growth is restricted around non-fertilized ovules or aborted seeds in pea. This mechanism would serve to adjust pericarp growth to the number of developing seeds.

Following fruit set, pericarp transcript abundance of both PsAFB2 (FIGS. 8 and 9E) and PsAFB6 (FIGS. 10 and 9F) was relatively constant from 2 to 20 DAA. While transcript abundance of PsAFB2 was similar in the vascular sutures, funiculus, and pericarp wall (FIG. 9E), transcript abundance of PsAFB6 was greater in the dorsal and ventral vascular sutures than in the pericarp wall (FIG. 9F). Furthermore, the pericarp dorsal vascular suture had in general slightly higher PsAFB6 mRNA levels than the pericarp ventral vascular suture (seeds are attached at the ventral vascular suture via the funiculus; FIGS. 9F, H) and the funiculus, which is rich in vascular tissue, had higher levels of PsAFB6 transcript than the pericarp tissues from 8 to 20 DAA (FIG. 9G). Both the vascular sutures and the funiculus can form abscission zones, either between each half of the pericarp (in the case of the sutures) or between the fruit and seed (in the case of the funiculus). Ethylene serves as an inducer of abscission (reviewed in Patterson, 2001), and the higher levels of PsAFB6 mRNA in the pericarp vascular suture tissues and in the funiculus may serve a developmental role in heightening auxin-induced ethylene sensitivity in these tissue, allowing for the prompt formation of abscission zones when ethylene is present.

PsAFB6 is believed to play a role in the regulation of pericarp development. Seed-derived 4-Cl-IAA is transported to the pericarp, where it has multiple actions including the upregulation of GA biosynthesis (Ozga et al., 2009) and inhibition of ethylene signalling (Johnstone et al., 2005), both of which promote pericarp growth. The modulation of auxin sensitivity through the regulation of the PsAFB6 receptor by 4-Cl-IAA may be an important factor in the regulation of both of these processes in pericarp development.

By repressing PsAFB6 transcription, 4-Cl-IAA downregulates its own signal perception, providing that PsAFB6 serves as an auxin receptor with the ability to bind 4-Cl-IAA. The downregulation of auxin perception by seed-produced 4-Cl-IAA could be a mechanism to moderate pericarp development in the presence of variable seed count. Under this hypothesis, auxin sensitivity is heightened when few seeds (and thus little 4-Cl-IAA signal) are present, allowing the pericarp to maintain growth even with low seed count. While wildtype pea fruit normally have between 4 and 7 seeds, a recently characterized line with a constitutively expressed PsGA3ox1 transgene is capable of maintaining fruit growth with fewer (1 to 3) seeds. Greater pericarp PsAFB6 transcript in fruit with fewer seeds would support the role of PsAFB6 regulation as a mechanism to adjust pericarp growth to variable seed count.

Figure 12:
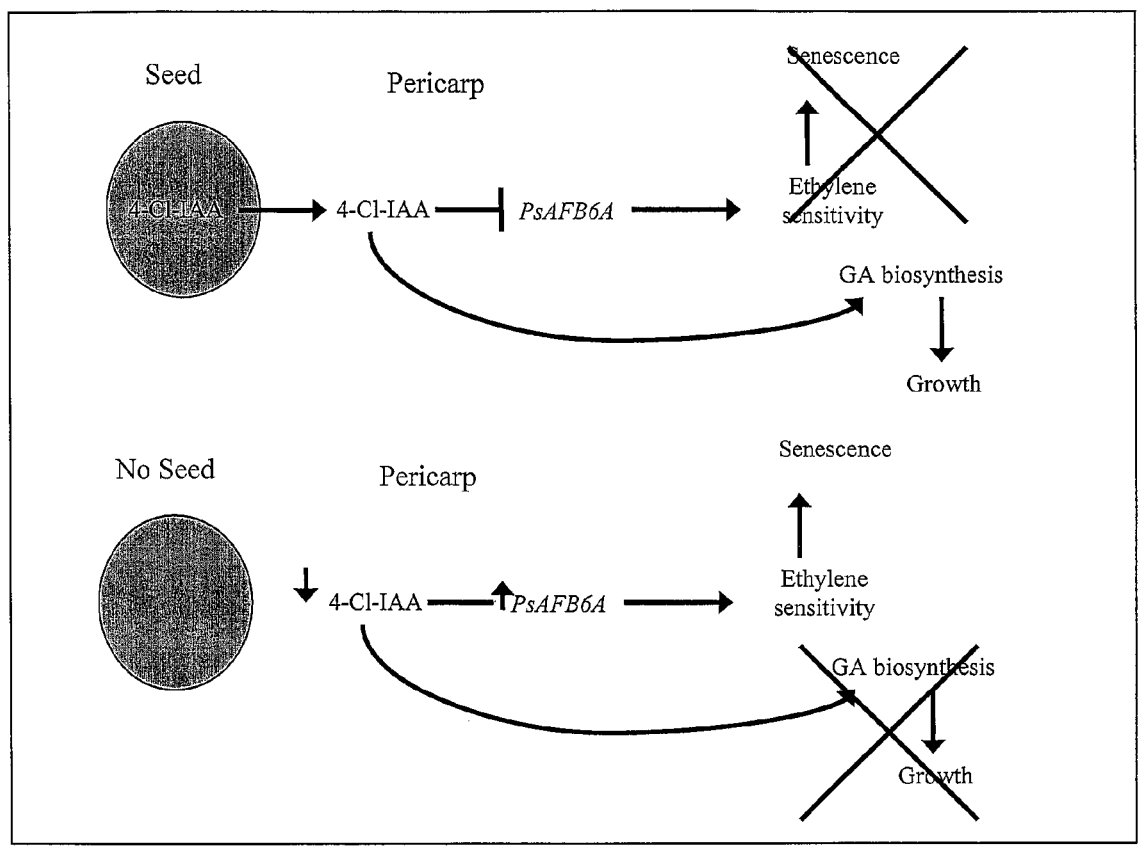
FIG. 12 is a schematic diagram of hormonal regulation during early pea fruit development.

The localization of PsAFB6 transcript to the abscission zones of the pea fruit indicates a role for this gene in the 4-Cl-IAA mediated repression of ethylene signalling. In this model, PsAFB6 promotes ethylene signalling, and the repression of PsAFB6 by 4-Cl-IAA reduces ethylene sensitivity, preventing abscission and ethylene-induced repression of GA biosynthesis. In the absence of 4-Cl-IAA, increased PsAFB6 transcript leads to increased ethylene sensitivity, priming abscission zones for ethylene perception and inhibiting pericarp GA biosynthesis (FIG. 12). The role of PsAFB6 as a regulator of ethylene response could be examined through the transcription profiling of ethylene receptors (PsERS) and members of the ethylene signal transduction pathway (Pisum orthologue(s) of AtEIN2), and by examining the response of these genes to seeds and auxin signals.

The regulation of PsAFB6 transcript levels by 4-Cl-IAA and viable seeds, while PsAFB2 remains largely unresponsive, raises the possibility that PsAFB6 serves as a 4-Cl-IAA specific receptor. Given that 4-Cl-IAA is not a naturally occurring auxin in *Arabidopsis*, the specificity of AFB receptors for alternate endogenous auxins has not been thoroughly investigated. Isolation of the gene product of PsAFB6 from a relevant protein expression system and binding assays with 4-Cl-IAA, IAA, and the other indole-substituted auxins used by Reinecke et al. (1999) should provide further insights into auxin-receptor specificity.

Exemplary embodiments of the present invention are described in the following Examples, which are set forth to aid in the understanding of the invention, and should not be construed to limit in any way the scope of the invention as defined in the claims which follow thereafter.

Example 1

Plant Material

Seeds of *Pisum sativum* L. I$_3$ Alaska-type were planted at an approximate depth of 2.5 cm in 3-L plastic pots (3 seed per pot) in Sunshine #4 ® potting mix (Sun Gro Horticulture, Vancouver, Canada). Plants were grown in a climate-controlled growth chamber with a 16 h-light/8 h-dark photoperiod (19° C./17° C.) with an average photon flux density of 383.5 µE/m$^2$s (measured with a LI-188 photometer, Li-Cor Biosciences, Lincoln, Nebr.).

To obtain RNA for cDNA generation, whole seeds at 14 days after anthesis (DAA), ovaries with seeds at 2 DAA, pericarps (seeds removed) at 2 DAA, and funiculi at 10 DAA were harvested. To determine the expression profiles of the AFB genes during early fruit development, pericarp and whole seeds were harvested at −2, −1, 0, 1, 2, 3, 4, 5, 6, 7, 8, 10, and 12 DAA. To investigate the role of fertilization and the presence of developing seeds on AFB transcript levels in the pericarp, flowers were emasculated at −2 DAA and pericarps were harvested at the equivalent to −1, 0, 1, 2, and 3 DAA for RNA extraction.

Figure 3:
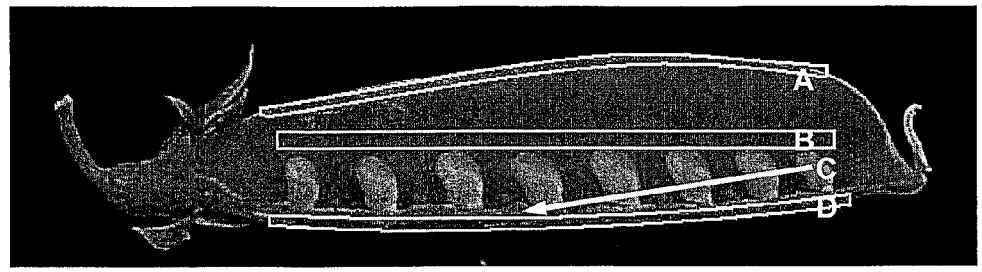
FIG. 3 is a photograph of a dissected pea indicating the location of tissues to examine the localization of transcripts in the pericarp vascular suture tissues, pericarp wall, and funiculus (RNA for qRT-PCR was isolated from the dorsal vascular suture traces (A), pericarp wall lacking vascular suture traces (B), the funiculus (between ventral trace and seed; C), and the ventral vascular suture traces (D)).

To determine the expression profiles of the AFB genes in developing seed tissues, seeds were harvested whole or dissected into seed coat, endosperm and embryo at 8, 10, and 12 DAA. At 14, 16, 18, and 20 DAA, seeds were dissected into seed coat and embryo or seed coat, cotyledons, and embryo axis. To examine the spatial expression of the AFB genes within the pericarp while seeds were rapidly expanding, pods were harvested at 8, 10, 12, 14, 16, 18, and 20 DAA and dissected into three regions (FIG. 3). The dorsal and ventral vascular suture regions were approximately 1 to 2 mm in width, and extended along most of the pericarp (regions where no seeds were present were omitted (A and D). The pericarp wall samples were approximately 2 to 3 mm in width, and were taken from the mid-pericarp wall region extending the majority of the length of the pericarp (B). Funiculi were also harvested from 8 to 20 DAA fruits. All tissues for cDNA generation and expression profiling were harvested into liquid nitrogen and stored at −80° C. until RNA extraction.

Example 2

Hormone Treatments

To examine the hormonal regulation of pericarp AFB mRNA levels, the pea split-pericarp assay was used (Ozga et al., 1992). Fruit at 2 DAA were split along the dorsal suture. Seeds were removed and pericarps were left for 12 hours prior to hormone application to reduce residual seed effects. IAA, 4-Cl-IAA, or GA$_3$ was applied to the inside of the pericarp (endocarp) at a concentration of 50 µM in 0.1% aqueous Tween 80 in a total volume of 30 µL. For split-pod, no seed controls (SPNS), 30 µL of 0.1% aqueous Tween 80 was applied. For split-pod controls (SP), seeds were not removed after the dorsal suture was opened, but 30 µL of 0.1% aqueous Tween 80 was applied 12 hours after pericarp splitting. As a further control for the split-pericarp procedure, intact pods were also harvested at the appropriate times. All fruit subjected to split-pericarp treatments were covered with plastic to maintain humidity, and all manipulations were carried out while pericarps remained on the plant. Intact controls were harvested at the 0 hour and 12 hour treatment timing, while all split-pericarp treatments were harvested at 12, 14, 20, and 24 hours after pericarp splitting (0, 2, 8, and 12 hours after hormone treatment).

Example 3

Degenerate PCR and Cloning cDNA was synthesized using multiple protocols from several tissues to maximize chances of obtaining at least one pool with high levels of the genes of interest. The first protocol utilized total RNA isolated from 14 DAA whole seeds, 2 DAA ovaries, 2 DAA pericarps, or 10 DAA funiculi. For RNA isolation, tissues were ground in liquid N$_2$ and subsamples of 20 to 300 mg Fw were removed for total RNA isolation using a guanidinium thiocyanate-phenol-chloroform extraction (Ozga et al., 2003). After extraction with either TRIZO1® (Invitrogen) or TRI REAGENT® (AMBION®) and centrifugation at 4° C. in a benchtop centrifuge to remove cellular debris, a phase separation using chloroform (0.2 mL/mL TRI REAGENT®) was performed and the organic phase discarded. RNA was precipitated from the aqueous phase with isopropanol (0.25 mL/mL TRI REAGENT®) and a high salt solution (1.2 M sodium citrate and 0.8 M NaCl) to remove polysaccharides. The RNA pellet was resuspended and RNA was precipitated with 8 M aqueous LiCl. The RNA pellet was again resuspended and a final precipitation with 3 M sodium acetate (pH=5.2, final concentration=96.77 mM) and 100% ethanol (final concentration=64.5% v/v) was performed. The RNA was pelleted and washed twice with 70% aqueous ethanol then resuspended and treated with DNAse (DNA-free kit; AMBION®). DEPC-treated water was utilized throughout this procedure to reduce RNAse contamination. RNA concentration was quantified by measuring $A_{260}$, and RNA purity was estimated with $A_{260}/A_{280}$ and $A_{260}/A_{230}$ ratios. RNA samples were diluted to 25 ng/µL and aliquoted to 96-well plates in a sterile laminar flowhood to reduce contamination.

To generate cDNA from total RNA, 1250 ng RNA was mixed with oligo-dT (12-18 bases in length, final concentration 2.14 µM), and nucleotides (0.71 mM each dNTP), brought to a final volume of 35 µL with water, heated at 65° C. for 5 minutes to minimize any secondary structures, and cooled to 4° C. for the remainder of the reaction assembly. SuperScript III reverse transcriptase (250 u; Invitrogen), dithiothreotol (DTT, final concentration 5 mM) and the supplied buffer were added to the reaction and cDNA synthesis was performed at 50° C. for one hour, after which point the reaction was halted by heating to 70° C. for 15 minutes.

The second protocol utilized RNA isolated from both 2 DAA pericarp and 6 DAA whole seeds. RNA was isolated as previously described and mRNA was selected for with a poly-T cellulose column (Poly-A purist, AMBION®) as per the manufacturer's directions. To generate cDNA from poly-A mRNA, 500 ng of RNA was mixed with oligo-dT (final concentration 2.5 µM), nucleotides (0.5 mM each dNTP), brought to a final volume of 13 µL with water, and heated as previously described. SuperScript III reverse transcriptase (400 U; Invitrogen), DTT (final concentration 5 mM), and the supplied buffer were added to the reaction and cDNA synthesis was performed as previously described. cDNA generated with either protocol was checked for concentration ($A_{260}$) and quality ($A_{260}/A_{280}$ and $A_{260}/A_{230}$) via a spectrophotometer and by agarose gel electrophoresis.

Some cDNA samples were treated with RNAse to remove RNA-cDNA duplexes that could potentially inhibit PCR. Approximately 500 ng of cDNA was incubated with 2 u of RNAse H (Invitrogen) for 80 minutes at 37° C. As the sample was already reverse transcribed, no RNAse deactivation was performed. Some cDNA samples were purified through a phenol/chloroform extraction. Samples (20 µL) were mixed with 20 µL phenol/chloroform/isoamyl alcohol (25:24:1 v/v/v, saturated with 10 mM TRIS, pH 8.0, 1 mM EDTA, Sigma-Aldrich), and the aqueous phase was removed and partitioned against 20 µL chloroform. cDNA was precipitated with sodium acetate (950 mM final concentration), glycogen (1 µL per 63 µL precipitation), and 95% ethanol (40 µL per 63 µL precipitation) at −80° C. for 2.5 hours. The precipitation was spun with a table-top microcentrifuge at 13 000 rpm for 10 minutes, then the pellet was washed twice with 100 µL 70% ethanol. The pellet was dried and resuspended in 15 µL DEPC-treated water.

PCR primers were designed by Dr. Dennis Reinecke with the CODEHOP algorithm, a program which generates degenerate primers when supplied with blocks of protein sequence (Rose et al., 2003). The protein sequences of 58 AFB genes from both angiosperms and gymnosperms were used to generate the two primers used to obtain initial sequence data (Table 4). PCR was successfully carried out with 150 ng of cDNA from 14 DAA whole seed and 2 DAA ovary tissues using Taq polymerase (0.56 µL per reaction; Invitrogen), the forward and reverse CODEHOP primers (50 µmol each per reaction), nucleotides (0.5 mM final concentration), magnesium chloride (4 mM final concentration), and the supplied buffer (final concentration 1×) in a total reaction volume of 20 µL. Reactions were carried out with the following thermocycling program: denaturation at 95° C. for 5 minutes, 35 cycles of denaturation at 94° C. for 30 seconds, annealing at 50° C. for 30 seconds, and polymerization at 72° C. for 70 seconds, followed by a final extension phase at 72° C. for 7 minutes. Products were analyzed with agarose gel electrophoresis.

TABLE 4

Degenerate primers used for amplification of interior sections of AFB genes.

| Primer | Sequence | Purpose |
|---|---|---|
| AFB-F | 5'-TGG TGT AGA AGG AAA GTG ATT GGN A (SEQ ID NO: 5) | Forward CODEHOP Primer |
| AFB-R | 5'-CAT CAG CGA AAG GAC AAT CTC TAA TYT CN (SEQ ID NO: 6) | Reverse CODEHOP Primer |

PCR products of the appropriate length were cloned via T/A overhangs into the pCR8 vector using the pCR8/GW/TOPO kit (Invitrogen). Briefly, 2 µL of the appropriate DNA was mixed with 0.5 µL high salt solution (1.2 M NaCl and 0.06 M MgCl$_2$) and 0.5 µL of the supplied linearized, topoisomerase I bound vector. The ligation reaction was held at room temperature for between 15 and 30 minutes, and then incubated with 50 µL competent TOP10 E. coli (Invitrogen) on ice for 20-40 minutes. Cells were heat shocked at 42° C. for 30 seconds and returned to 4° C. to cool, then incubated with 125 µL S.O.C. medium at 37° C. for approximately one hour. Cells were plated on LB agar plates containing 100 µg/mL spectinomycin and grown overnight at 37° C.

Individual colonies were picked from plates and grown overnight in 5 mL LB containing 100 µg mL spectinomycin at 37° C. with agitation at 250 rpm. Cells were collected by centrifugation in either an Avanti J-E centrifuge (Beckman-Coulter) or a benchtop microcentrifuge and excess media was drained off. Plasmid DNA was isolated with either the GenElute miniprep kit (Sigma-Aldrich) or QIAQUICK® spin miniprep kit (Qiagen) as recommended by the manufacturers. Plasmids were screened for insert size by restriction digestion with EcoRI followed by agarose gel electrophoresis. The inserts of clones containing appropriately sized fragments were sequenced from the T3 and T7 or M13 primer sites within the vector using the BigDye Terminator v3.1 Cycle Sequencing kit and 3730 DNA Analyzer (Applied Biosystems) at the University of Alberta Molecular Biology Service Unit as per the manufacturer's recommendations. Sequence editing and alignment was performed in BioEdit.

Example 4

Random Amplification of cDNA Ends of PsAFB2

Figure 4:
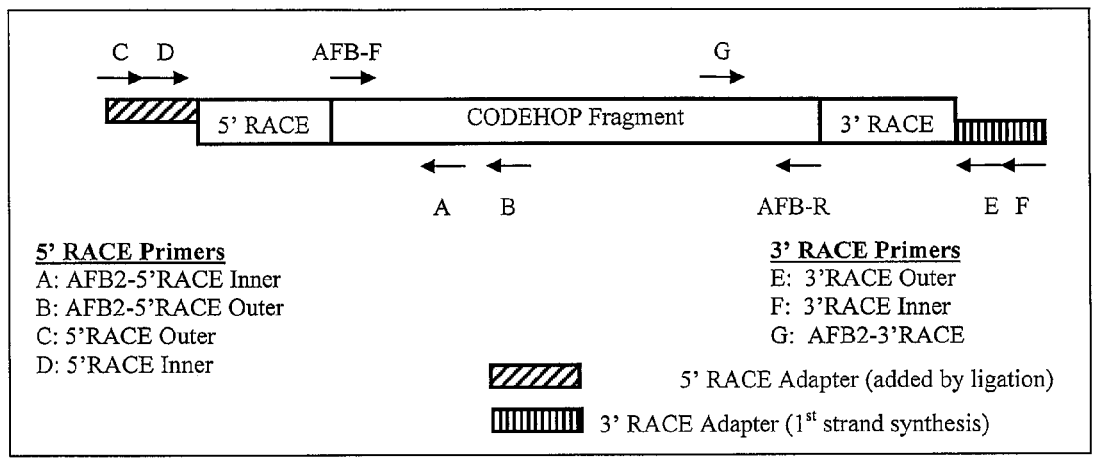
FIG. 4 is a schematic diagram of a cloning strategy to obtain PsAFB2. While displayed as one molecule, the schematic represents both the 5' (5' RACE Adapter to undetermined points within the CODEHOP fragment) and 3' (3' RACE Adapter to undetermined points within the CODEHOP fragment) cDNA pools, which are used separately for amplification of each end.

RNA-ligase mediated RACE (RLM-RACE) was used to generate cDNA for PCR amplification of the ends of PsAFB2 (FIG. 4). The 3' RACE cDNA pool was generated from 14 DAA whole seeds, 2 DAA ovaries, 2 DAA pericarps, and 10 DAA funiculi with a primer consisting of poly-T and a unique sequence (across from primers E and F), which was later used along with a gene specific primer (primer G) to amplify the unknown 3' end.

In the first stage of 5' RACE cDNA synthesis, poly-A selected RNA from 14 DAA whole seeds, 2 DAA ovaries, 2 DAA pericarps, and 10 DAA funiculi was treated with a calf intestinal phosphatase to cleave the 5' phosphate group from any remaining rRNA, tRNA, DNA, and fragmented mRNA. The sample was then treated with tobacco alkaline pyrophosphatase, which cleaves the 5' 7-methylguanine cap from full-length mRNA, leaving a free 5' phosphate. A single-strand ligation was performed between these molecules and a synthetic RNA containing a unique sequence (across from primers C and D), then cDNA synthesis was performed from random decamers. The unique sequence was later used with an internal gene specific primer (multiple internal primers were used in this study, A and B) to amplify the unknown 5' end.

The RNA used for RLM-RACE was the same poly-A selected RNA used in the previously described CODEHOP experiments. Generation of cDNA pools was performed using the FirstChoice RLM-RACE system (AMBION®) according to the manufacturer's directions.

The 5' region of PsAFB2 was amplified in three stages of nested PCR from the 5' RLM-RACE cDNA pools as follows. Template cDNA (1) was mixed with nucleotides (final concentration 0.2 mM each), 20 µmol of AFB2-5'RACE outer gene specific primer, 20 µmol of supplied 5' RACE Outer primer (FIRSTCHOICE® RLM-RACE kit, Ambion), MgCl$_2$ (final concentration 1.4 mM), 1.25 U Taq polymerase (Invitrogen), and the supplied reaction buffer in a final volume of 25 µL. Thermocycling consisted of denaturation at 94° C. for 3 minutes, 35 cycles of 94° C. for 15 seconds, 50° C. for 20 seconds, and 72° C. for 30 seconds, and final extension at 72° C. for 5 minutes. The second stage of nested PCR was carried out using 1 µL of the first reaction products. Template DNA was mixed with nucleotides (final concentration 0.2 mM each), 20 µmol of AFB2-5'RACE outer gene specific primer, 20 µmol of the 5' RACE Inner primer (FIRSTCHOICE® RLM-RACE kit, AMBION®), MgCl$_2$ (final concentration 1.8 mM), 1.25 U Taq polymerase (Invitrogen), and the supplied reaction buffer in a final volume of 25 µL. Thermocycling consisted of denaturation at 94° C. for 5 minutes, 35 cycles of 94° C. for 1 minute, 55° C. for 1 minute, and 72° C. for 1 minute, and final extension at 72° C. for 5 minutes. The third stage of nested PCR was carried out using 2 µL of the reaction products of the second stage PCR. Template DNA was mixed with nucleotides (final concentration 0.2 mM each), 20 µmol of AFB2-5'RACE inner gene specific primer, 20 µmol of 5' RACE Inner primer (FIRSTCHOICE® RLM-RACE kit, AMBION®), MgCl$_2$ (final concentration 1.8 mM), 1.25 U Taq polymerase (Invitrogen), and the supplied reaction buffer in a final volume of 25 µL. Thermocycling consisted of denaturation at 94° C. for 5 minutes, 40 cycles of 94° C. for 1 minute, 55° C. for 1 minute, and 72° C. for 1 minute, and final extension at 72° C. for 5 minutes. The 5' RACE PCR reaction products were analyzed by agarose gel electrophoresis, and bands of the appropriate size were excised. DNA was extracted using a gel extraction kit (QIAQUICK®, Qiagen), then ligation, transformation, plating, and fragment analysis proceeded as previously noted.

The 3' region of PsAFB2 was amplified in two stages of nested PCR from the 3' RLM-RACE cDNA pools as follows (primers listed in Table 5). Template cDNA (1 µL) was mixed with nucleotides (final concentration 0.8 mM each), 8 µmol of AFB2-3'RACE gene specific primer, 8 µmol of the 3' RACE Outer primer (FIRSTCHOICE® RLM-RACE kit, AMBION®), MgCl$_2$ (final concentration 1.75 mM), 0.5 U Taq polymerase (Invitrogen), and the supplied reaction buffer in a final volume of 20 µL. The thermocycling consisted of an initial denaturation of 5 minutes at 94° C. followed by 35 cycles of denaturation at 94° C. for 15 seconds, primer annealing at 55° C. for 15 seconds, and extension at 72° C. for 25 seconds, and a final elongation at 72° C. for 3 minutes. The second stage was performed using 5 µL of the first-stage reactions as template. Template DNA was mixed with nucleotides (final concentration 0.8 mM each), 20 µmol of AFB2-3'RACE gene specific primer, 20 µmol of the 3' RACE Inner primer (FIRSTCHOICE® RLM-RACE kit, Ambion), MgCl$_2$ (final concentration 1.75 mM 1.25 U Taq polymerase (Invitrogen), and the supplied reaction buffer in a final volume of 50 µl, Thermocycling for the second phase consisted of initial denaturation at 94° C. for 5 minutes, and 35 cycles of denaturation at 94° C. for 30 seconds, annealing at 55° C. for 30 seconds, and primer extension at 72° C. for 45 seconds, and a final extension at 72° C. for 5 minutes. The 3' RACE PCR reaction products were analyzed by agarose gel electrophoresis, and bands of the appropriate size were excised. DNA was extracted using a gel extraction kit (QIAQUICK®, Qiagen), then ligation, transformation, plating, and fragment analysis proceeded as previously noted.

TABLE 5

Primers used for PsAFB2 RLM-RACE.

| Primer | Sequence | Purpose |
| --- | --- | --- |
| AFB2-5'RACE outer | 5'-AGC TAC AGC AGC AAG TCC ATC AGT (SEQ ID NO: 7) | Gene specific primer for AFB2 5'RACE (B) |
| AFB2-5'RACE inner | 5'-AAC CTA AGC TCC TCC AAC CCA ACT (SEQ ID NO: 8) | Gene specific primer for AFB2 5'RACE (A) |
| AFB2-3'RACE | 5'-CAA TGC AGC CAC TGG ATG AAG GTT (SEQ ID NO: 9) | Gene specific primer for AFB2 3'RACE (G) |
| 5' RACE Adapter | 5'-GCU GAU GGC GAU GAA UGA ACA CUG CGU UUG CUG GCU UUG AUG AAA (SEQ ID NO: 10) | RNA oligo ligated to 5' end of decapped transcripts |
| 3' RACE Adapter | 5'-GCG AGC ACA GAA TTA ATA CGA CTC ACT ATA GGT12 VN (SEQ ID NO: 11) | Primer for 1$^{st}$ strand synthesis |
| 5' RACE Outer | 5'-GCT GAT GGC GAT GAA TGA ACA CTG (SEQ ID NO: 12) | 5' RACE PCR (not gene specific; C) |

TABLE 5-continued

Primers used for PsAFB2 RLM-RACE.

| Primer | Sequence | Purpose |
| --- | --- | --- |
| 5' RACE Inner | 5'-CGC GGA TCC GAA CAC TGC GTT TGC TGG CTT TGA TG (SEQ ID NO: 13) | As above (D) |
| 3' RACE Outer | 5'-GCG AGC ACA GAA TTA ATA CGA CT (SEQ ID NO: 14) | 3' RACE PCR (not gene specific; E) |
| 3' RACE Inner | 5'-CGC GGA TCC GAA TTA ATA CGA CTC ACT ATA GG (SEQ ID NO: 15) | As above (F) |

5'RACE Adapter is an RNA molecule, and thus contains uracil.
All other primers used are DNA oligonucleotides.

Example 5

Random Amplification of cDNA Ends of PsAFB6

Figure 5:
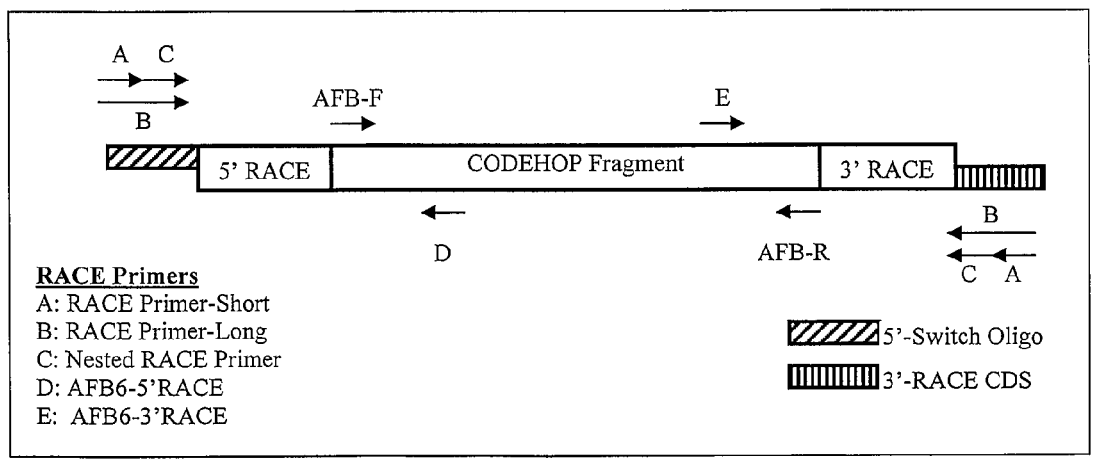
FIG. 5 is a schematic diagram of a cloning strategy to obtain PsAFB6. While displayed as one molecule, the schematic represents both the 5' (5'-Switch Oligo to undetermined points within the CODEHOP fragment) and 3' (3'-RACE CDS, complementary DNA sequence, to undetermined points within the CODEHOP fragment) cDNA pools, which are used separately for amplification of each end.

A template-switching method was used to construct cDNA for PCR amplification of the ends of PsAFB6 (FIG. 5). The 3' RACE cDNA pools were generated with a primer consisting of poly-T and a unique sequence (across from primer B), which was later used along with a gene specific primer (primer E) to amplify the unknown 3' end. The first strand synthesis of the 5' RACE cDNA pool was generated from poly-T using a reverse transcriptase which adds several non-template cytosine bases to the end of the strand. Second strand synthesis was then carried out from a primer consisting of a unique sequence (across from primer B) ending in three G bases, which allow it to pair with the first-strand cDNA. This unique sequence was later used with another gene specific primer (primer D) to amplify the unknown 5' end. Primer sequences are listed in Table 6.

Between 250 and 1200 ng of total RNA isolated from 14 DAA whole seed, 2 DAA ovaries, 2 DAA pericarps, or 10 DAA funiculi, in a total volume of 4 μL were used for both 5' and 3' RACE. For 5' RACE, 12 μmol each of the 5'-RACE CDS and 5'Switch Oligo (for second strand priming) were added to the RNA. For 3' RACE, 12 μmol of the 3'-RACE CDS and water (to a final volume of 6 μL) were added to the reaction. The reactions were incubated at 72° C. for 2 minutes to eliminate secondary structures, then were transferred to ice for the remainder of reaction assembly. Nucleotides (final concentration 1 mM each), 200 U reverse transcriptase (H— MMLC reverse transcriptase, Fermentas), and the supplied reaction buffer (final concentration 1×) were added, and the reaction was carried out at 42° C. for 90 minutes. Reactions were diluted with 100 μL water, and stopped by incubation for 10 minutes at 72° C.

The 5' region of PsAFB6 was amplified from 300 ng of 5'RACE cDNA using touchdown PCR as follows. Template was mixed with nucleotides (final concentration 0.5 mM each), 50 μmol of AFB6-5'RACE gene specific primer (D), 37.5 μmol of RACE Primer-Short, 7.5 μmol of RACE Primer-Long, MgCl$_2$ (final concentration 2.75 mM), 0.44 Taq polymerase (Invitrogen), and water in a final volume of 20 μL. The thermocycling conditions consisted of an initial denaturation at 94° C. for 3 minutes, touchdown PCR for 10 cycles (denaturation at 94° C. for 30 seconds, primer annealing for 30 seconds at 61° C. minus 0.5° C. per cycle, and extension at 72° C. for 2 minutes), followed by normal PCR for 20 cycles (denaturation at 94° C. for 30 seconds, primer annealing for 30 seconds at 55° C., and extension at 72° C. for 2 minutes), followed by a final elongation at 72° C. for 5 minutes.

The 3' region of PsAFB6 was amplified from 300 ng of 3' RACE cDNA using touchdown PCR as follows. Template was mixed with nucleotides (final concentration 0.5 mM each), 30 μmol of AFB6-3'RACE gene specific primer (E), 30 μmol of RACE Primer-Short, 6 μmol of RACE Primer-Long, MgCl$_2$ (final concentration 2.25 mM), 0.3 μL Taq polymerase (Invitrogen), and water in a final volume of 20 μL. The thermocycling consisted of an initial denaturation of 3 minutes at 94° C. followed by 30 cycles of denaturation at 94° C. for 30 seconds, primer annealing at 70° C. for 30 seconds (minus 0.5° C. per cycle), and extension at 72° C. for 2 minutes, and a final elongation at 72° C. for 5 minutes.

Both 5' and 3' RACE PCR reaction products were analyzed by agarose gel electrophoresis, and bands of the appropriate size were excised. DNA was extracted using a gel extraction kit (QIAQUICK®, Qiagen), then ligation, transformation, plating, and fragment analysis proceeded as previously noted.

TABLE 6

Primers used for PsAFB6 RACE.

| Primer | Sequence | Purpose |
| --- | --- | --- |
| 5'-RACE CDS | 5'-TTT TTT TTT TTT TTT TTT TTT TTT TVN (SEQ ID NO: 16) | First strand cDNA synthesis from poly-A tail |
| 5'-Switch Oligo | 5'-AAG CAG TCG TAT GAA CGC AGA GTA CGC GGG (SEQ ID NO: 17) | Second strand cDNA synthesis from non-template C's |
| 3'-RACE CDS | 5'-AAG CAG TCG TAT GAA CGC AGA GTA CTT TTT TTT TTT TTT TTT TTT TTT TVN (SEQ ID NO: 18) | First strand cDNA synthesis from poly-A tail |
| RACE Primer-Short | 5'-CTA ATA GCA CTC ACT ATA GGG C (SEQ ID NO: 19) | Amplification from 5' or 3' RACE cDNA (not gene specific; A) |

TABLE 6-continued

Primers used for PsAFB6 RACE.

| Primer | Sequence | Purpose |
|---|---|---|
| RACE Primer-Long | 5'-CTA ATA GCA CTC ACT ATA GGG CAA GCA GTC GTA TGA ACG CAG AGT (SEQ ID NO: 20) | Same as above, but allows second round of PCR from nested primer to amplify weak signal (B) |
| Nested RACE Primer | 5'-AAG CAG TCG TAT GAA CGC AGA GT (SEQ ID NO: 21) | Second round of PCR for weak 5' or 3' RACE products (C) |
| AFB6-5'RACE | 5'-GCT TTC TGG GAA GCA ACT CAA CCA (SEQ ID NO: 22) | Gene specific primer for AFB6 5'RACE (D) |
| AFB6-3'RACE | 5'-AGG ATG CCG GAA GCT TCA CTA TGT (SEQ ID NO: 23) | Gene specific primer for AFB6 3'RACE (E) |

Example 6

Amplification of Full-Length cDNA

Full length PsAFB2 was amplified from poly-A cDNA prepared from 2 DAA pericarps and 14 DAA seeds as described above. cDNA template (300 ng) was mixed with nucleotides (final concentration 0.5 mM each), 50 µmol of the PsAFB2 FWD primer, 50 µmol of the PsAFB2 REV primer (Table 7), MgCl$_2$ (final concentration 2.25 mM), 3.1 u Taq polymerase (Invitrogen), and the supplied buffer in a final volume of 20 µL. The thermocycling consisted of an initial denaturation of 5 minutes at 94° C. followed by 30 cycles of denaturation at 94° C. for 30 seconds, primer annealing at 50° C. for 30 seconds, and extension at 72° C. for 90 seconds, followed by a final elongation at 72° C. for 7 minutes. Products were analysed with agarose gel electrophoresis, then were cloned into the PCR8 gateway vector as previously described. Clones were analyzed as previously described, and clones containing the complete PsAFB2 gene were sequenced across completely in several overlapping fragments from both direction using the T3, T7, PsAFB2 FWD, PsAFB2 REV, and two internal primers generated to region of PsAFB2 isolated via the CODEHOP procedure using the sequencing protocols previously noted. All attempts to amplify and clone the full-length PsAFB6 gene were unsuccessful.

TABLE 7

Primers used to amplify full-length coding region of PsAFB2.

| Primer | Sequence | Purpose |
|---|---|---|
| PsAFB2 FWD | 5'-ATG AAT TAT TTT CCA GAC GAG GTA ATA GAA CA (SEQ ID NO: 24) | Amplification of full length coding region |
| PsAFB2 REV | 5'-CTA CAG AGT CCA TAC ATA GTC TGG TG (SEQ ID NO: 25) | Amplification of full length coding region |

Example 7 qRT-PCR

All transcript quantification was performed on a StepOnePlus sequence detector (Applied Biosystems). Reverse transcription and quantification was performed using TaqMan One-Step RT-PCR Master Mix (Applied Biosystems; final concentration 1×) and 200 ng of DNAse treated total RNA (final concentration 8 ng µL$^{-1}$) in duplicate in a final volume of 25 µL per well. The final concentration of forward and reverse primers was 300 nM each, and the final concentration of probe was 100 nM. Reverse transcription was carried out for 30 minutes at 48° C. DNA polymerase antibody was denatured at 95° C. for 10 minutes. Quantification was carried out for 40 cycles of the following program: denaturation at 95° C. for 15 seconds, primer annealing and extension at 60° C. for 1 minute. Probes were labelled at the 5' end with FAM (6-carboxyfluorescein) and at the 3' end with the MGB quencher (Applied Biosystems).

As an additional loading control, 18s rRNA was quantified on 3 ng of DNAse treated total RNA generated from a single dilution of the original 8 ng µL stocks (final concentration 120 pg/µL) using the same master mix, primer and probe concentrations, and thermocycling conditions. A mixture of primers containing 3' hydroxyl and C$_6$NH$_2$ chain terminators in a 1:9 ratio was used to quantify 18s transcript levels. The addition of competitive primers allows a larger amount of template to be used while maintaining an acceptable reaction profile, effectively decreasing the variation which would be introduced during the serial dilution of RNA samples. The 18s probe was labelled at the 5' end with VIC and at the 3' end with the TAMRA quencher (Applied Biosystems). RNA templates and reaction components were aliquoted to 96-well plates in a sterile laminar flow hood, and all tools and the hood itself were washed regularly with RNAse Zap (AMBION®) to reduce RNAse contamination. The coefficient of variation of 18s rRNA expression data was calculated for each plate, and any samples with exceptionally high or low Ct values were removed from further analysis.

Primers and probes for PsAFB2 and PsAFB6 were designed with the PRIMER EXPRESS® software package (Applied Biosystems). In addition to the amplicon used for quantification, a larger amplicon for each gene was generated with the same probe, but different primers which bind to regions outside of the quantification amplicon (Table 8).

TABLE 8

Primer and probe sequences used in qRT-PCR assays.

| Gene | | Sequence | Amplicon length |
|------|------|----------|-----------------|
| PsAFB2 | Forward | 5'-TCG ATG CAA CAA AAC CTG ACT (SEQ ID NO: 26) | 80 bp |
| | Reverse | 5'-TCG TTT GCA TGA CTG TAC GAT (SEQ ID NO: 27) | |
| | Probe | 5'-TGC AGC CAC TGG AT (SEQ ID NO: 28) | |
| PsAFB6 | Forward | 5'-TGT CGC TAC CGT AGT CCA AA (SEQ ID NO: 29) | 52 bp |
| | Reverse | 5'-TGC AGA GGC GGA AAT GA (SEQ ID NO: 30) | |
| | Probe | 5'-CTG CCC CGA CTT TA (SEQ ID NO: 31) | |
| PsAFB2 (validation) | Forward | 5'-CAG TAG CCA AGA ACT GTC CA (SEQ ID NO: 32) | 159 bp |
| | Reverse | 5'-TCA ACT GAC CGG AGA GTG AT (SEQ ID NO: 33) | |
| | Probe | 5'-TGC AGC CAC TGG AT (SEQ ID NO: 34) | |
| PsAFB6 (validation) | Forward | 5'-GTC GTC AAA TGA CCA ATG CTG (SEQ ID NO: 35) | 114 bp |
| | Reverse | 5'-GTT CGT CCG TCA GGT AAT CTT G (SEQ ID NO: 36) | |
| | Probe | 5'-CTG CCC CGA CTT TA (SEQ ID NO: 37) | |
| 18s rRNA | Forward | 5'-ACG TCC CTG CCC TTT GTA CA (SEQ ID NO: 38) | 62 bp |
| | Reverse | 5'-CAC TTC ACC GGA CCA TTC AAT (SEQ ID NO: 39) | |
| | Probe | 5'-ACC GCC CGT CGC TCC TAC CG (SEQ ID NO: 40) | |

Probes for PsAFB6 and PsAFB2 were labelled at the 5' end with FAM (6-carboxy-fluorescein) and at the 3' end with the MGB quencher (Applied Biosystems). Probe for 18s rRNA was labelled at the 5' end with VIC and at the 3' end with the TAMRA quencher (Applied Biosystems).

A series of samples was assayed with both the inner and outer primers in tandem, and both primer sets yielded the same trends in relative transcript abundance, increasing confidence that the correct RNA was amplified. Additionally, reactions with both the quantification and outer validation sets of primers produced single bands of the appropriate sizes when qRT-PCR reaction products were separated on a 2.5% agarose gel. Table 9 contains results of searches of the qRT-PCR amplicons (including validation primer sets) of PsAFB2 sequentially against the non-redundant nucleotide using the BLASTN 2.2.21 program (Zhang et al., 2000). Searches using the same protocol with PsAFB6 returned no hits. Additionally, the PsAFB2 amplicon could not be aligned to the nucleotide sequence of PsAFB6 using default settings, and vice versa.

TABLE 9

Results of search of nr/nt library using the PsAFB2 qRT-PCR amplicon as query. Default settings of the BLASTN 2.2.21 program were used.

| Accession | Description | Total score | E value |
|-----------|-------------|-------------|---------|
| AC133780.33 | *Medicago truncatula* clone mth2-27f3, complete sequence | 228 | 7e−57 |
| AK286220.1 | *Glycine max* cDNA, clone: GMFL01-24-D14 | 152 | 4e−34 |

Relative transcript levels were calculated using the ΔCt method (Livak and Schmittgen, 2001) using the following formula, where X is an arbitrary value equal to or greater than the highest assayed Ct value and E is the reaction efficiency for the amplicon in question:

$$\text{Transcript abundance} = (1+E)^{X-Ct} \quad (1)$$

Reaction efficiency was calculated for each amplicon after validation experiments. A single RNA sample was diluted over several log concentrations (typically from 400-500 ng/reaction to 0.05-0.08 ng/reaction), and running qRT-PCR as previously described. Data were plotted on a semi-log graph of Ct and log(input RNA) and a linear regression was calculated (Pfaffl, 2006). Assuming the $r^2$ value was sufficiently high, the slope of this equation was then used to calculate reaction efficiency (E; as a percentage) with the following formula:

$$\text{Efficiency} = (10^{[-1/slope]}-1)*100 \quad (2)$$

Example 8

Hormone Extraction, HPLC, and GC-MS

All metabolite extraction and quantification was performed by Dr. Leon Kurepin (University of Calgary, Calgary, Canada). Plant tissues were dissected and processed. Metabolite extraction used the same process as described previously, but internal standards of 400 ng [$^{13}C_6$]IAA (Cambridge Isotope Laboratories, Inc.) and 50-300 ng of [$^2H_4$]-4-Cl-IAA (gift from Dr. J. Cohen) were added to the MeOH extract prior to filtering.

Samples were dissolved in 1 mL of 10% MeoH with 1% acetic acid and injected into the HPLC (Koshioka et al., 1983). The HPLC apparatus (Waters Ltd.) consisted of two pumps (model M-45), an automated gradient controller (model 680), and a Rheodyne injector (model 7125). The solvent reservoir for pump A was filled with 10% MeOH in 1% acetic acid [H2O:MeOH:acetic acid=89:10:1, (v/v)], while pump B was 100% MeOH. A reversed phase $C_{18}$ Radial-PAK µ-Bondapak column (8 mm×10 cm) was used with a manually implemented 10-73% gradient program at a flow rate of 2 mL min$^{-1}$ i.e., 0-10 min (pump A, 100%; pump B, 0%), 10-50 min (pump A, 30%; pump B; 70%), 50-80 min (pump A, 0%); pump B, 100%), 80-90 min (pump A, 100%; pump B, 0%).

Fractions from $C_{18}$ HPLC were collected at 9.53 min for IAA and 11.11 min for 4-Cl-IAA. These fractions were subsequently methylated by ethereal $CH_2N_2$ and derivatized to their trimethylsilyl ethers for GC-MS. The derivatized sample was injected into a capillary column installed in an Agilent 6890 GC with a capillary direct interface to an Agilent 5973 mass selective detector. The dimensions of the capillary column were 0.25 µm film thickness, 0.25 mm internal diameter, 30 m DB-1701 (model J&W122-0732, J&W Scientific, Inc.). The GC temperature program was: 1 min at 60° C., followed by an increase to 240° C. at a rate of 25 C min$^{-1}$ and an increase at 5° C. min$^{-1}$ to 280° C. where it remained constant for 15 min before returning to 60° C. The interface temperature was maintained at 280° C. The dwell time was 100 ms and data was processed using HP G1034C MS ChemStation Software.

Endogenous auxins were identified by GC-MS-SIM via comparisons of GC-retention times of auxins and internal standards and by the relative intensities of molecular ion ($M^+$) pairs. Relative intensities of at least one other characteristic m/z ion pair for each auxin and its standard (IAA/[$^{13}C_6$]-IAA, 202/208 and 261/267; 4-Cl-IAA/[$^2H_4$]-4-Cl-IAA, 236/240 and 295/299) were also compared. Quantification was accomplished using the peak areas of the 202/208 ions for IAA/[$^{13}C_6$]-IAA, and the peak areas of the 236/240 ions for 4-Cl-IAA/[$^2H_4$]-4-Cl-IAA in the equations for isotope dilution analysis from Gaskin and MacMillan (1991) as adapted by DW Pearce (Jacobsen et al., 2002).

Example 9

Putative AFB Protein Sequences

Alignments were performed in ClustalW2 using NJ clustering and the BLOSUM distance matrix. Additionally, domain prediction with the SMART (Simple Modular Architecture Research Tool) program (Schultz et al., 1998, Letunic et al., 2005) was performed using the protein sequences from PsAFB2, PsAFB6, and AtTir1 (for reference).

REFERENCES

The following references are incorporated herein by reference (where permitted) as if reproduced in their entirety. All references are indicative of the level of skill of those skilled in the art to which this invention pertains.

Ausubel, F. M., Brent, R., Kingston, R. E., Moore, D. D., Deidman, J. G. and Tatham, A. S. (1995) Current Protocols in Molecular Biology. New York.

Bandurski, R., and A. Schulze (1977) Concentration of Indole-3-acetic acid and its derivatives in plants. *Plant Physiol.* 60:211-213.

Bandurski, R., J. Cohen, J. Solvin, and D. Reinecke (1995) Auxin biosynthesis and metabolism. In P J Davies, ed, *Plant Hormones: Physiology, Biochemistry and Molecular Biology* 2$^{nd}$ edition. Kluwer Academics Publishers, Dordrecht, The Netherlands pp. 649-670

Bartel, B. (1997) Auxin biosynthesis. *Ann. Rev. Plant Physiol. Plant Mol. Biol.* 48:51-66

Bialek, K., and J. Cohen (1989) Quantitation of indoleacetic acid conjugates in bean seeds by direct tissue hydrolysis. *Plant Physiol.* 90:398-400

Cannon, S., L. Sterck., S. Rombauts, S. Sato, F. Cheung, J. Gouzy, X. Wang, J. Mudge, J. Vasdewani, T. Schiex, M. Spannagl, E. Monaghan, C. Nicholson, S. Humphray, H. Schoof, K. Mayer, J. Rogers, F. Quetier, G. Oldroyd, F. Debelle, D. Cook, B. Roe, C. Town, S. Tabata, Y. van de Peer, and N. Young (2006) Legume evolution viewed through the *Medicago truncatula* and *Lotus japonicus* genomes. *Proc. Nat. Acad. Sci. USA* 103:14959-14964.

Davidson, S., R. Elliott, C. Helliwell, A. Poole, and J. Reid (2003) The pea gene NA encodes ent-kaurenoic acid oxidase. *Plant Physiol.* 131:335-344.

Davies, D. (1975) Studies of seed-development in *Pisum sativum*. I. Seed size in reciprocal crosses. *Planta* 124: 303-309.

Dharmasiri, N., and M. Estelle (2004) Auxin signalling and regulated protein degradation. Trends *Plant Sci.* 9:302-308.

Dharmasiri, N., S. Dharmasiri, and M. Estelle (2005a) The F-box protein TIR1 is an auxin receptor. *Nature* 435:441-445.

Dharmasiri, N., S. Dharmasiri, D. Weijers, E. Lechner, M. Yamada, L. Hobbie, J. Ehrismann, G Jtirgens, and M. Estelle (2005b) Plant development is regulated by a family of auxin receptor F box proteins. *Dev. Cell* 9:109-119.

Gagne, J., B. Downes, S. Shiu, A. Durski, and R. Vierstra (2002) The F-box subunit of the SCF E3 complex is encoded by a diverse superfamily of genes in *Arabidopsis*. *Proc. Nat. Acad. Sci. USA* 99:11519-11524.

Gaskin, P., and J. Macmillan (1991) GC-MS of the gibberellins and related compounds. *Methodology and a library of spectra*. Bristol, UK: University of Bristol (Cantock's Enterprises).

Gray, W., J. del Pozo, L. Walker, L. Hobbie, E. Risseeuw, T. Banks, W. Crosby, M. Yang, H. Ma, and M. Estelle (1999) Identification of an SCF ubiquitin-ligase complex required for auxin response in *Arabidopsis thaliana*. *Genes Dev.* 13:1678-1691.

Gray, W., S. Kepinski, D. Rouse, O. Leyser, and M. Estelle (2001) Auxin regulates SCF(TIR1)-dependant degradation of AUX/IAA proteins. *Nature* 414:271-276.

Hagen, G., and T. Guilfoyle (2002) Auxin-responsive gene expression: genes, promoters and regulatory factors. *Plant Mol. Biol.* 49:373-385.

Jacobsen, J., D. Pearce, A. Poole, R. Pharis, and L. Mander (2002) Abscisic acid, phaseic acid, and gibberellin contents associated with dormancy and germination in barley. *Physiologica Plantarum* 115:428-441.

Jakubowska, A., and S. Kowalczyk (2004) The auxin conjugate 1-O-indole-3-acetyl-β-D-glucose is synthesized in immature legume seeds by IAGlc synthase and may be used for modification of some high molecular weight compounds. *J. Exp. Bot.* 55:791-801.

Jenik, P., C. Gillmor, and W. Lukowitz (2007) Embryonic patterning in *Arabidopsis thaliana*. *Annu. Rev. Cell Dev. Biol.* 23:207-236.

Johnstone, M., D. Reinecke, and J. Ozga (2005) The auxins IAA and 4-Cl-IAA differentially modify gibberellin action via ethylene response in developing pea fruit. *J. Plant Growth Reg.* 24:214-225.

Kapoor, B. (1966) Contributions to the cytology of endosperm in angiosperms-XII. *Pisum sativum* L. *Genetica* 37:557-568.

Katayama, M., S. Thiruvikraman, and S. Marumo (1987) Identifiation of 4-chloroindole-3-acetic acid and its methyl ester in immature seeds of *Vicia amurensis* (the tribe Vicieae), and their absence from three species of *Phaseoleae. Plant Cell Physiol.* 28: 383-386.

Katayama, M., S. Thiruvikraman, and S. Marumo (1988) Localization of 4-chloroindole-3-acetic acid in seeds of *Pisum sativum* and its absence from all other organs. *Plant Cell Physiol.* 29:889-891.

Kepinski, S., and O. Leyser (2005) The *Arabidopsis* F-box protein TIR1 is an auxin receptor. *Nature* 435:446-451.

Koshioka, M., K. Taken, F. Beall, and R. Pharis (1983) Purification and separation of gibberilins from their precursors and glucosyl conjugates. *Plant. Physiol.* 73:398-406.

Law, D., and R. Hamilton (1982) A rapid isotope dilution method for analysis of indole-3-acetic acid and indoleacetyl aspartic acid from small amounts of plant tissue. *Biochem. Biophys. Res. Comm.* 106:1035-1041.

Letunic, I., R. Copley, B. Pils, S. Pinkert, J. Schultz, and P. Bork (2005) SMART 5: domains in the context of genomes and networks. *Nuc. Acid Res.* 34: D257-D260.

Leyser, O. (2002) Molecular genetics of auxin signaling. *Ann. Rev. Plant Biol.* 53:377-398

Livak, K. and T. Schmittgen (2001) Analysis of relative gene expression data using real-time quantitative PCR and the 2(-Delta Delta C(T)) method. *Methods* 25:402-408.

Lur, H.-S., and T. Setter (1993) Role of auxin in maize endospeim development: timing of nuclear DNA endoreduplication, zein expression, and cytokinin. *Plant Physiol.* 103:273-280

Magnus, V., J. Ozga, D. Reinecke, G Pierson, T. Lame, J. Cohen, and M. Brenner (1997) 4-chloroindole-3-acetic and indole-3-acetic acids in *Pisum sativum. Phytochem.* 46:675-681

Marumo, S., H. Hattori, H. Abe, and K. Munakata (1968) Isolation of a novel auxin, methyl 4-chloroindoleacetate from immature seeds of *Pisum sativum. Agr. Biol. Chem.* 32:117-118.

Nordström, A-C., F. Jacobs, and L. Eliasson (1991) Effect of exogenous indole-3-acetic acid and indole-3-butyric acid on internal levels of the respective auxins and their conjugation with aspartic acid during adventitious root formation in pea cuttings. *Plant Physiol.* 96:856-861.

Orzáez, D., R. Blay, and A. Granell (1999) Programme of senescence in petals and carpels of *Pisum sativum* L. flowers and its control by ethylene. *Planta* 208:220-226.

Ozga, J., D. Reinecke, B. Ayele, P. Ngo, C. Nadeau, and A. Wickramarathna (2009) Developmental and Hormonal Regulation of Gibberellin Biosynthesis and Catabolism in Pea Fruit. *Plant Physiol.* 150:448-462.

Ozga J., and M. Brenner (1992) The effect of 4-Cl-IAA on growth and GA metabolism in deseeded pea pericarp. *Plant Physiol.* 99:S-12.

Ozga, J., and D. Reinecke (1999) Interaction of 4-chloroindole-3-acetic acid and gibberellins in early pea fruit development. *Plant Growth Reg.* 27:33-38.

Ozga, J., M. Brenner, and D. Reinecke (1992) Seed effects on gibberellin metabolism in pea pericarp. *Plant Physiol.* 100:88-94.

Ozga, J., J. Yu, and D. Reinecke (2003) Pollination-, development- and auxin-specific regulation of gibberellin 3β-hydroxylase gene expression in pea fruit and seeds. *Plant Physiol.* 131:1137-1146.

Park, J., H. Kim, and J. Kim (2002) Mutation in domain II of IAA1 confers diverse auxin-related phenotypes and represses auxin-activated expression of Aux/IAA genes in steroid regulator-inducible systems. *Plant J.* 32:669-683.

Patterson, S. (2001) Cutting loose. Abscission and dehiscence in *Arabidopsis. Plant Physiol.* 126:494-500.

Pfaffl, M. (2006) "Relative quantification" in Real-time PCR (T. Dorak ed.) Published by International University Line, 63-82.

Reid, J., and J. Ross (1993) A mutant-based approach, using *Pisum sativum*, to understanding plant growth. *Int. J. Plant Sci.* 154:22-34.

Reinecke, D., J. Ozga, and V. Magnus (1995) Effect of halogen substitution of indole-3-acetic acid on biological activity in pea fruit. *Phytochem.* 40:1361-1366.

Reinecke, D., J. Ozga, N. The, V. Magnus, and B. Kojić-Prodié(1999) Molecular properties of 4-substituted indole-3-acetic acids affecting pea pericarp elongation. *Plant Growth Reg.* 27:39-48

Rose, T., J. Henikoff, and S. Henikoff (2003) CODEHOP (COnsensus-DEgenerate Hybrid Oligonuceotide Primer) PCR primer design. *Nuc. Acid Res.* 31:3763-3766

Schneider, E., C. Kazakoff, and F. Wightman (1985) Gas chromatography-mass spectrometry evidence for several endogenous auxins in pea seedlings organs. *Planta* 165: 232-241

Schultz, J., F. Milpetz, P. Bork, and C. Ponting (1998) SMART, a simple modular architecture research tool: Identification of signalling domains. *Proc. Nat. Acad. Sci. USA* 95:5857-5864

Tan., X., L. Calderon-Villalobos, M. Sharon, C. Zheng, C. Robinson, M. Estelle, and N. Zheng (2007) Mechanism of auxin perception by the TIR1 ubiquitin ligase. *Nature* 446:640-645.

Tiwari, S., X. Wang, G Hagen, and T. Guilfoyle (2001) AUX/IAA proteins are active repressors, and their stability and activity are modulated by auxin. *Plant Cell* 13:2809-2822.

Trique K et al. 2007. Characterization of *Arabidopsis thaliana* mismatch specific endonuclease: application to mutation discovery by TILLING in pea. The Plant J. 51:1116-1125.

Ulmasov, T., Z. Liu, G Hagen, and T. Guilfoyle (1995) Composite structure of auxin responsive elements. *Plant Cell* 7:1611-1623.

Ulmasov, T., G Hagen, and T. Guilfoyle (1999) Dimerization and DNA binding of auxin response factors. *Plant J.* 19:309-319.

van Huizen, R., J. Ozga, D. Reinecke, B. Twitchen, and L. Mander (1995) Seed and 4-chloroindole-3-acetic acid regulation of gibberellin metabolism in pea pericarp. *Plant Phys.* 109:1213-1217.

van Huizen, R., J. Ozga, and D. Reinecke (1997) Seed and hormonal regulation of Gibberellin-20 oxidase expression in pea pericarp. *Plant Phys.* 128:1379-1389.

Woodward, A., and B. Bartel (2005) Auxin: regulation, action, and interaction. *Ann. Bot.* 95:707-735.

SEQUENCE LISTING

<160> NUMBER OF SEQ ID NOS: 40

<210> SEQ ID NO 1
<211> LENGTH: 1716
<212> TYPE: DNA
<213> ORGANISM: Pisum sativum

<400> SEQUENCE: 1

| | | | | | |
|---|---|---|---|---|---|
| atgaattatt | ttccagacga | ggtaatagaa | catgtgtttg | actatgtggt | gtcacatagc | 60 |
| gacagaaaca | gtttgtcttt | ggtatgcaaa | agttggtata | gaatagaggg | atttacaagg | 120 |
| aaaagggtgt | tcataggaaa | ctgttactct | attagtcctg | agaggttggt | agagaggttt | 180 |
| cctgatttca | aatctttaac | tctaaaggga | aaacctcatt | ttgctgactt | cagtttggtt | 240 |
| cctcatggtt | ggggtggttt | tgtttatcca | tggattgaag | ctcttgctaa | gagtagagtt | 300 |
| gggttggagg | agcttaggtt | gaagaggatg | gttgtgtcag | atgagagcct | ggagctactg | 360 |
| tctcgttctt | tcatgaattt | taagtctttg | gttcttgtta | gctgtgaagg | gttcaccact | 420 |
| gatggacttg | ctgctgtagc | tgcaaattgc | aggtctctta | gggagctaga | tttgcaagag | 480 |
| aatgaagttg | aagatcacaa | aggacagtgg | ctaagttgtt | ttccggaaaa | ctgtacatca | 540 |
| ctcgtcgctc | ttaattttgc | ttgccttaaa | ggagagatta | acgtgggagc | acttgagaga | 600 |
| cttgtgcaa | gatcacctaa | cctcaagact | ctaaggttaa | accgttccgt | gccggctgat | 660 |
| gcacttcaaa | ggatactaat | gcgagcgcct | caaatagcag | atttgggtat | tggatcattt | 720 |
| atccatgatc | tcaattcaga | ggcctacata | aagcttaaga | ataccattct | tagatgccgg | 780 |
| tcaataacga | gtttgtccgg | attttttggaa | gtggctcctt | ttagccttgc | tgctgtgtat | 840 |
| ccaatttgcc | ggaacttaac | atccttgaac | ttgagctatg | cagcaagcat | tcagggcgct | 900 |
| gagcttatta | aacttattcg | ccattgcggc | aaactacagc | gcttatggat | aatggattgc | 960 |
| attggagaca | aaggactagt | tgctgtagct | actatatgta | aagagttgca | agaattgagg | 1020 |
| gtatttccat | cggcaccatt | tggaaatcaa | gcagctgtta | ccgaagtagg | acttgttgcg | 1080 |
| atatcaaagg | gatgcccaaa | gctccactcg | ttactctact | tctgccacca | gatgacaaat | 1140 |
| gctgctctca | taacagtagc | caagaactgt | ccaaattta | tccgatttag | gttatgcatc | 1200 |
| ctcgatgcaa | caaaacctga | ctccgacaca | atgcagccac | tggatgaagg | ttttggggca | 1260 |
| atcgtacagt | catgcaaacg | actgaggcgg | ctatcactct | ccggtcagtt | gaccgaccag | 1320 |
| gtcttccttt | acattggaat | gtacgcggag | cagcttgaaa | tgctatctat | tgcttttgct | 1380 |
| ggcgagagtg | acaagggaat | gctctatgta | ttgaatggtt | gcaaaaagct | tcgcaagctc | 1440 |
| gagataagag | actgcccttt | cggcgacaca | gcacttctga | cagacgtagg | gaagtatgaa | 1500 |
| acaatgcgat | cccttttggat | gtcgtcgtgt | gaggtgactg | taggagcatg | caagacattg | 1560 |
| gcgaagaaga | tgccgagttt | gaatgtggag | atcttcaatg | aaagtgaaca | agcagattgt | 1620 |
| tatgtggaag | atgggcaaag | agtggagaag | atgtatttgt | atcgttctgt | ggctggtaaa | 1680 |
| agggaagatg | caccagacta | tgtatggact | ctgtag | | | 1716 |

<210> SEQ ID NO 2
<211> LENGTH: 571
<212> TYPE: PRT
<213> ORGANISM: Pisum sativum

<400> SEQUENCE: 2

Met Asn Tyr Phe Pro Asp Glu Val Ile Glu His Val Phe Asp Tyr Val
1               5                   10                  15

-continued

Val Ser His Ser Asp Arg Asn Ser Leu Ser Leu Val Cys Lys Ser Trp
        20                  25                  30

Tyr Arg Ile Glu Gly Phe Thr Arg Lys Arg Val Phe Ile Gly Asn Cys
            35                  40                  45

Tyr Ser Ile Ser Pro Glu Arg Leu Val Glu Arg Phe Pro Asp Phe Lys
50                  55                  60

Ser Leu Thr Leu Lys Gly Lys Pro His Phe Ala Asp Phe Ser Leu Val
65                  70                  75                  80

Pro His Gly Trp Gly Phe Val Tyr Pro Trp Ile Glu Ala Leu Ala
                85                  90                  95

Lys Ser Arg Val Gly Leu Glu Glu Leu Arg Leu Lys Arg Met Val Val
            100                 105                 110

Ser Asp Glu Ser Leu Glu Leu Leu Ser Arg Ser Phe Met Asn Phe Lys
        115                 120                 125

Ser Leu Val Leu Val Ser Cys Glu Gly Phe Thr Thr Asp Gly Leu Ala
        130                 135                 140

Ala Val Ala Ala Asn Cys Arg Ser Leu Arg Glu Leu Asp Leu Gln Glu
145                 150                 155                 160

Asn Glu Val Glu Asp His Lys Gly Gln Trp Leu Ser Cys Phe Pro Glu
                165                 170                 175

Asn Cys Thr Ser Leu Val Ala Leu Asn Phe Ala Cys Leu Lys Gly Glu
            180                 185                 190

Ile Asn Val Gly Ala Leu Glu Arg Leu Val Ala Arg Ser Pro Asn Leu
        195                 200                 205

Lys Thr Leu Arg Leu Asn Arg Ser Val Pro Ala Asp Ala Leu Gln Arg
210                 215                 220

Ile Leu Met Arg Ala Pro Gln Ile Ala Asp Leu Gly Ile Gly Ser Phe
225                 230                 235                 240

Ile His Asp Leu Asn Ser Glu Ala Tyr Ile Lys Leu Lys Asn Thr Ile
                245                 250                 255

Leu Arg Cys Arg Ser Ile Thr Ser Leu Ser Gly Phe Leu Glu Val Ala
            260                 265                 270

Pro Phe Ser Leu Ala Ala Val Tyr Pro Ile Cys Arg Asn Leu Thr Ser
        275                 280                 285

Leu Asn Leu Ser Tyr Ala Ala Ser Ile Gln Gly Ala Glu Leu Ile Lys
        290                 295                 300

Leu Ile Arg His Cys Gly Lys Leu Gln Arg Leu Trp Ile Met Asp Cys
305                 310                 315                 320

Ile Gly Asp Lys Gly Leu Val Ala Val Ala Thr Ile Cys Lys Glu Leu
                325                 330                 335

Gln Glu Leu Arg Val Phe Pro Ser Ala Pro Phe Gly Asn Gln Ala Ala
            340                 345                 350

Val Thr Glu Val Gly Leu Val Ala Ile Ser Lys Gly Cys Pro Lys Leu
        355                 360                 365

His Ser Leu Leu Tyr Phe Cys His Gln Met Thr Asn Ala Ala Leu Ile
        370                 375                 380

Thr Val Ala Lys Asn Cys Pro Asn Phe Ile Arg Phe Arg Leu Cys Ile
385                 390                 395                 400

Leu Asp Ala Thr Lys Pro Asp Ser Asp Thr Met Gln Pro Leu Asp Glu
                405                 410                 415

Gly Phe Gly Ala Ile Val Gln Ser Cys Lys Arg Leu Arg Arg Leu Ser
            420                 425                 430

Leu Ser Gly Gln Leu Thr Asp Gln Val Phe Leu Tyr Ile Gly Met Tyr

```
                    435                 440                 445
Ala Glu Gln Leu Glu Met Leu Ser Ile Ala Phe Ala Gly Glu Ser Asp
        450                 455                 460

Lys Gly Met Leu Tyr Val Leu Asn Gly Cys Lys Lys Leu Arg Lys Leu
465                 470                 475                 480

Glu Ile Arg Asp Cys Pro Phe Gly Asp Thr Ala Leu Leu Thr Asp Val
                485                 490                 495

Gly Lys Tyr Glu Thr Met Arg Ser Leu Trp Met Ser Cys Glu Val
                500                 505                 510

Thr Val Gly Ala Cys Lys Thr Leu Ala Lys Lys Met Pro Ser Leu Asn
            515                 520                 525

Val Glu Ile Phe Asn Glu Ser Glu Gln Ala Asp Cys Tyr Val Glu Asp
        530                 535                 540

Gly Gln Arg Val Glu Lys Met Tyr Leu Tyr Arg Ser Val Ala Gly Lys
545                 550                 555                 560

Arg Glu Asp Ala Pro Glu Tyr Val Trp Thr Leu
                565                 570

<210> SEQ ID NO 3
<211> LENGTH: 1725
<212> TYPE: DNA
<213> ORGANISM: Pisum sativum

<400> SEQUENCE: 3
```

| | | | | | |
|---|---|---|---|---|---|
| atggaaccac | aaaccatgaa | tcccagttca | gtctttccag | atgaagtgct | ggagagaatt | 60 |
| ctcagcatgg | tgaagtcacg | caaagacaag | agttcggttt | cattggtttg | caaagactgg | 120 |
| ttcgacgctg | aaagatggtc | gagaaagaat | gtgttcatag | gtaactgtta | ttccgttaca | 180 |
| ccagagatct | tgactcaaag | atttccgaat | gttcgaagtg | ttacattgaa | agggaagcca | 240 |
| cgtttctctg | atttcaactt | ggttcctgct | aattggggtg | ctgatattca | tccatggctt | 300 |
| gttgttttcg | ctgaaaagta | ccctttttctt | gaagagttaa | ggcttaagag | aatggttgtt | 360 |
| actgatgaga | gtttagagtt | tctggctttt | tcgtttccga | attttaaagc | tctttctctt | 420 |
| ttgagctgtg | atggatttag | cactgatggt | ttagctgctg | ttgctactaa | ttgcaagaac | 480 |
| ttaactgagc | ttgacataca | agagaatggt | atcgaagaca | aaagcggtaa | ctggttgagt | 540 |
| tgcttcccag | aaagctttac | atcattggaa | gtgttgaact | tgccaaccct | aaccaatgaa | 600 |
| gtaaacatcg | acgcgctaga | gaaacttgtt | ggtaggtgca | aatcattgaa | gactttgaag | 660 |
| gttaacaaaa | gcgtaacgct | ggaacagttg | aaaaaacttc | ttgttcgcgc | ccctcagtta | 720 |
| tgtgagcttg | gcagtggctc | attttcgcaa | gagctgacat | ctcagcagta | tgcagagctc | 780 |
| gaaaccgcgt | tcaaaaattg | taaaagcctt | cacaccctgt | ctggtttatg | ggtggcttca | 840 |
| gcgcgatatc | ttcaagttct | ataccctgcg | tgcgcgaatc | tgactttttt | gaatttttagc | 900 |
| tatgctcctc | ttgacagtga | agatcttacc | aagattcttg | ttcactgtcc | taatcttcga | 960 |
| cgtctttggg | ttgttgacac | cgttgaagac | aagggacttg | aagcggttgg | atcgaactgt | 1020 |
| ccattgcttg | aggaactgcg | tgttttttcct | gcagatccgt | ttgacgagga | agctgaaggc | 1080 |
| ggggtgactg | aatcgggggtt | tgttgctgtc | tctgaaggat | gccggaagct | tcactatgtt | 1140 |
| ctctactttt | gtcgtcaaat | gaccaatgct | gctgtcgcta | ccgtagtcca | aaactgcccc | 1200 |
| gactttactc | atttccgcct | ctgcataatg | aaccctggcc | agcaagatta | cctgacggac | 1260 |
| gaacctatgg | acgaggcctt | cggagaagtt | gttaagaact | gcactaaact | tcagaggctc | 1320 |
| gctgtatcag | gttatctaac | ggacctcaca | ttcgagtata | taggaaagta | tgccaaaaac | 1380 |

```
ttggaaacgc tttcggtggc ttttgcagga agcagtgatt ggggaatgga gtgtgtactg    1440
gtcggatgtc cgaaactgag aaaactcgag ataagagaca gtccattcgg aaatgcagcg    1500
cttttggcag gtttggagaa gtacgagtcg atgaggtcac tttggatgtc gtcctgcaga    1560
ctgacgatga atggatgtag attttttggca ggagaaaagc cgaggttgaa tgtcgaagta    1620
atgcaggaag aaggaggcga tgatagtcgg gccgaaaaac tttatgttta tcgatctgtt    1680
gccgggccaa gaagggatgc acctcctttt gttctcactc tctga                   1725

<210> SEQ ID NO 4
<211> LENGTH: 524
<212> TYPE: PRT
<213> ORGANISM: Pisum sativum

<400> SEQUENCE: 4
```

Met Glu Pro Gln Thr Met Asn Pro Ser Ser Val Phe Pro Asp Glu Val
1               5                   10                  15

Leu Glu Arg Ile Leu Ser Met Val Lys Ser Arg Lys Asp Lys Ser Ser
            20                  25                  30

Val Ser Leu Val Cys Lys Asp Trp Phe Asp Ala Glu Arg Trp Ser Arg
        35                  40                  45

Lys Asn Val Phe Ile Gly Asn Cys Tyr Ser Val Thr Pro Glu Ile Leu
    50                  55                  60

Thr Gln Arg Phe Pro Asn Val Arg Ser Val Leu Glu Phe Leu Ala Phe
65                  70                  75                  80

Ser Phe Pro Asn Phe Lys Ala Leu Ser Leu Ser Cys Asp Gly Phe
                85                  90                  95

Ser Thr Asp Gly Leu Ala Ala Val Ala Thr Asn Cys Lys Asn Leu Thr
            100                 105                 110

Glu Leu Asp Ile Gln Glu Asn Gly Ile Glu Asp Lys Ser Gly Asn Trp
        115                 120                 125

Leu Ser Cys Phe Pro Glu Ser Phe Thr Ser Leu Glu Val Leu Asn Phe
    130                 135                 140

Ala Asn Leu Thr Asn Glu Val Asn Ile Asp Ala Leu Glu Lys Leu Val
145                 150                 155                 160

Gly Arg Cys Lys Ser Leu Lys Thr Leu Lys Val Asn Lys Ser Val Thr
                165                 170                 175

Leu Glu Gln Leu Lys Lys Leu Leu Val Arg Ala Pro Gln Leu Cys Glu
            180                 185                 190

Leu Gly Ser Gly Ser Phe Ser Gln Glu Leu Thr Ser Gln Gln Tyr Ala
        195                 200                 205

Glu Leu Glu Thr Ala Phe Lys Asn Cys Lys Ser Leu His Thr Leu Ser
    210                 215                 220

Gly Leu Trp Val Ala Ser Ala Arg Tyr Leu Gln Val Leu Tyr Pro Ala
225                 230                 235                 240

Cys Ala Asn Leu Thr Phe Leu Asn Phe Ser Tyr Ala Pro Leu Asp Ser
                245                 250                 255

Glu Asp Leu Thr Lys Ile Leu Val His Cys Pro Asn Leu Arg Arg Leu
            260                 265                 270

Trp Val Val Asp Thr Val Glu Asp Lys Gly Leu Glu Ala Val Gly Ser
        275                 280                 285

Asn Cys Pro Leu Leu Glu Glu Leu Arg Val Phe Pro Ala Asp Pro Phe
    290                 295                 300

Asp Glu Glu Ala Glu Gly Gly Val Thr Glu Ser Gly Phe Val Ala Val

```
                305                 310                 315                 320
Ser Glu Gly Cys Arg Lys Leu His Tyr Val Leu Tyr Phe Cys Arg Gln
            325                 330                 335

Met Thr Asn Ala Ala Val Ala Thr Val Val Gln Asn Cys Pro Asp Phe
            340                 345                 350

Thr His Phe Arg Leu Cys Ile Met Asn Pro Gly Gln Gln Asp Tyr Leu
            355                 360                 365

Thr Asp Glu Pro Met Asp Glu Ala Phe Gly Glu Val Val Lys Asn Cys
    370                 375                 380

Thr Lys Leu Gln Arg Leu Ala Val Ser Gly Tyr Leu Thr Asp Leu Thr
385                 390                 395                 400

Phe Glu Tyr Ile Gly Lys Tyr Ala Lys Asn Leu Glu Thr Leu Ser Val
                405                 410                 415

Ala Phe Ala Gly Ser Ser Asp Trp Gly Met Glu Cys Val Leu Val Gly
            420                 425                 430

Cys Pro Lys Leu Arg Lys Leu Glu Ile Arg Asp Ser Pro Phe Gly Asn
            435                 440                 445

Ala Ala Leu Leu Ala Gly Leu Glu Lys Tyr Glu Ser Met Arg Ser Leu
        450                 455                 460

Trp Met Ser Ser Cys Arg Leu Thr Met Asn Gly Cys Arg Phe Leu Ala
465                 470                 475                 480

Gly Glu Lys Pro Arg Leu Asn Val Glu Val Met Gln Glu Gly Gly
                485                 490                 495

Asp Asp Ser Arg Ala Glu Lys Leu Tyr Val Tyr Arg Ser Val Ala Gly
            500                 505                 510

Pro Arg Arg Asp Ala Pro Pro Phe Val Leu Thr Leu
            515                 520

<210> SEQ ID NO 5
<211> LENGTH: 25
<212> TYPE: DNA
<213> ORGANISM: Artificial Sequence
<220> FEATURE:
<223> OTHER INFORMATION: AFB-F, forward CODEHOP primer
<220> FEATURE:
<221> NAME/KEY: misc_feature
<222> LOCATION: (24)..(24)
<223> OTHER INFORMATION: n is a, c, g, or t

<400> SEQUENCE: 5
tggtgtagaa ggaaagtgat tggna                                         25

<210> SEQ ID NO 6
<211> LENGTH: 29
<212> TYPE: DNA
<213> ORGANISM: Artificial Sequence
<220> FEATURE:
<223> OTHER INFORMATION: AFB-R, reverse CODEHOP primer
<220> FEATURE:
<221> NAME/KEY: misc_feature
<222> LOCATION: (29)..(29)
<223> OTHER INFORMATION: n is a, c, g, or t

<400> SEQUENCE: 6
catcagcgaa aggacaatct ctaatytcn                                     29

<210> SEQ ID NO 7
<211> LENGTH: 24
<212> TYPE: DNA
<213> ORGANISM: Artificial Sequence
<220> FEATURE:
```

-continued

```
<223> OTHER INFORMATION: Primer used for PsAFB2 RLM-RACE; AFB2-5'RACE
      outer

<400> SEQUENCE: 7
agctacagca gcaagtccat cagt                                              24

<210> SEQ ID NO 8
<211> LENGTH: 24
<212> TYPE: DNA
<213> ORGANISM: Artificial Sequence
<220> FEATURE:
<223> OTHER INFORMATION: Primer used for PsAFB2 RLM-RACE; AFB2-5'RACE
      inner

<400> SEQUENCE: 8
aacctaagct cctccaaccc aact                                              24

<210> SEQ ID NO 9
<211> LENGTH: 24
<212> TYPE: DNA
<213> ORGANISM: Artificial Sequence
<220> FEATURE:
<223> OTHER INFORMATION: Primer used for PsAFB2 RLM-RACE; AFB2-3'RACE

<400> SEQUENCE: 9
caatgcagcc actggatgaa ggtt                                              24

<210> SEQ ID NO 10
<211> LENGTH: 45
<212> TYPE: RNA
<213> ORGANISM: Artificial Sequence
<220> FEATURE:
<223> OTHER INFORMATION: Primer used for PsAFB2 RLM-RACE; 5' RACE
      Adapter

<400> SEQUENCE: 10
gcugauggcg augaaugaac acugcguuug cuggcuuuga ugaaa                       45

<210> SEQ ID NO 11
<211> LENGTH: 35
<212> TYPE: DNA
<213> ORGANISM: Artificial Sequence
<220> FEATURE:
<223> OTHER INFORMATION: Primer used for PsAFB2 RLM-RACE; 3' RACE
      Adapter
<220> FEATURE:
<221> NAME/KEY: misc_feature
<222> LOCATION: (35)..(35)
<223> OTHER INFORMATION: n is a, c, g, or t

<400> SEQUENCE: 11
gcgagcacag aattaatacg actcactata ggtvn                                  35

<210> SEQ ID NO 12
<211> LENGTH: 24
<212> TYPE: DNA
<213> ORGANISM: Artificial Sequence
<220> FEATURE:
<223> OTHER INFORMATION: Primer used for PsAFB2 RLM-RACE; 5' RACE Outer

<400> SEQUENCE: 12
gctgatggcg atgaatgaac actg                                              24

<210> SEQ ID NO 13
<211> LENGTH: 35
<212> TYPE: DNA
<213> ORGANISM: Artificial Sequence
```

```
<220> FEATURE:
<223> OTHER INFORMATION: Primer used for PsAFB2 RLM-RACE; 5' RACE Inner

<400> SEQUENCE: 13
cgcggatccg aacactgcgt ttgctggctt tgatg                                  35

<210> SEQ ID NO 14
<211> LENGTH: 23
<212> TYPE: DNA
<213> ORGANISM: Artificial Sequence
<220> FEATURE:
<223> OTHER INFORMATION: Primer used for PsAFB2 RLM-RACE; 3' RACE Outer

<400> SEQUENCE: 14
gcgagcacag aattaatacg act                                               23

<210> SEQ ID NO 15
<211> LENGTH: 32
<212> TYPE: DNA
<213> ORGANISM: Artificial Sequence
<220> FEATURE:
<223> OTHER INFORMATION: Primer used for PsAFB2 RLM-RACE; 3' RACE Inner

<400> SEQUENCE: 15
cgcggatccg aattaatacg actcactata gg                                     32

<210> SEQ ID NO 16
<211> LENGTH: 27
<212> TYPE: DNA
<213> ORGANISM: Artificial Sequence
<220> FEATURE:
<223> OTHER INFORMATION: Primer used for PsAFB6 RACE; 5'-RACE CDS
<220> FEATURE:
<221> NAME/KEY: misc_feature
<222> LOCATION: (27)..(27)
<223> OTHER INFORMATION: n is a, c, g, or t

<400> SEQUENCE: 16
tttttttttt tttttttttt tttttvn                                           27

<210> SEQ ID NO 17
<211> LENGTH: 30
<212> TYPE: DNA
<213> ORGANISM: Artificial Sequence
<220> FEATURE:
<223> OTHER INFORMATION: Primer used for PsAFB6 RACE; 5'-Switch Oligo

<400> SEQUENCE: 17
aagcagtcgt atgaacgcag agtacgcggg                                        30

<210> SEQ ID NO 18
<211> LENGTH: 57
<212> TYPE: DNA
<213> ORGANISM: Artificial Sequence
<220> FEATURE:
<223> OTHER INFORMATION: Primer used for PsAFB6 RACE; 3'-RACE CDS
<220> FEATURE:
<221> NAME/KEY: misc_feature
<222> LOCATION: (57)..(57)
<223> OTHER INFORMATION: n is a, c, g, or t

<400> SEQUENCE: 18
aagcagtcgt atgaacgcag agtactttt tttttttttt tttttttttt tttttvn           57

<210> SEQ ID NO 19
<211> LENGTH: 22
<212> TYPE: DNA
```

```
<213> ORGANISM: Artificial Sequence
<220> FEATURE:
<223> OTHER INFORMATION: Primer used for PsAFB6 RACE; RACE Primer-Short

<400> SEQUENCE: 19
ctaatagcac tcactatagg gc                                              22

<210> SEQ ID NO 20
<211> LENGTH: 45
<212> TYPE: DNA
<213> ORGANISM: Artificial Sequence
<220> FEATURE:
<223> OTHER INFORMATION: Primer used for PsAFB6 RACE; RACE Primer-Long

<400> SEQUENCE: 20
ctaatagcac tcactatagg gcaagcagtc gtatgaacgc agagt                     45

<210> SEQ ID NO 21
<211> LENGTH: 23
<212> TYPE: DNA
<213> ORGANISM: Artificial Sequence
<220> FEATURE:
<223> OTHER INFORMATION: Primer used for PsAFB6 RACE; Nested RACE Primer

<400> SEQUENCE: 21
aagcagtcgt atgaacgcag agt                                             23

<210> SEQ ID NO 22
<211> LENGTH: 24
<212> TYPE: DNA
<213> ORGANISM: Artificial Sequence
<220> FEATURE:
<223> OTHER INFORMATION: Primer used for PsAFB6 RACE; AFB6-5'RACE

<400> SEQUENCE: 22
gctttctggg aagcaactca acca                                            24

<210> SEQ ID NO 23
<211> LENGTH: 24
<212> TYPE: DNA
<213> ORGANISM: Artificial Sequence
<220> FEATURE:
<223> OTHER INFORMATION: Primer used for PsAFB6 RACE; AFB6-3'RACE

<400> SEQUENCE: 23
aggatgccgg aagcttcact atgt                                            24

<210> SEQ ID NO 24
<211> LENGTH: 32
<212> TYPE: DNA
<213> ORGANISM: Artificial Sequence
<220> FEATURE:
<223> OTHER INFORMATION: Primer to amplify full-length coding region of
      PsAFB2; PsAFB2 FWD

<400> SEQUENCE: 24
atgaattatt ttccagacga ggtaatagaa ca                                   32

<210> SEQ ID NO 25
<211> LENGTH: 26
<212> TYPE: DNA
<213> ORGANISM: Artificial Sequence
<220> FEATURE:
<223> OTHER INFORMATION: Primer to amplify full-length coding region of
      PsAFB2; PsAFB2 REV

<400> SEQUENCE: 25
```

```
ctacagagtc catacatagt ctggtg                                          26

<210> SEQ ID NO 26
<211> LENGTH: 21
<212> TYPE: DNA
<213> ORGANISM: Artificial Sequence
<220> FEATURE:
<223> OTHER INFORMATION: Forward primer for PsAFB2 in qRT-PCR assay

<400> SEQUENCE: 26
tcgatgcaac aaaacctgac t                                               21

<210> SEQ ID NO 27
<211> LENGTH: 21
<212> TYPE: DNA
<213> ORGANISM: Artificial Sequence
<220> FEATURE:
<223> OTHER INFORMATION: Reverse primer for PsAFB2 in qRT-PCR assay

<400> SEQUENCE: 27
tcgtttgcat gactgtacga t                                               21

<210> SEQ ID NO 28
<211> LENGTH: 14
<212> TYPE: DNA
<213> ORGANISM: Artificial Sequence
<220> FEATURE:
<223> OTHER INFORMATION: Probe for PsAFB2 in qRT-PCR assay

<400> SEQUENCE: 28
tgcagccact ggat                                                       14

<210> SEQ ID NO 29
<211> LENGTH: 20
<212> TYPE: DNA
<213> ORGANISM: Artificial Sequence
<220> FEATURE:
<223> OTHER INFORMATION: Forward primer for PsAFB6 in qRT-PCR assay

<400> SEQUENCE: 29
tgtcgctacc gtagtccaaa                                                 20

<210> SEQ ID NO 30
<211> LENGTH: 17
<212> TYPE: DNA
<213> ORGANISM: Artificial Sequence
<220> FEATURE:
<223> OTHER INFORMATION: Reverse primer for PsAFB6 in qRT-PCR assay

<400> SEQUENCE: 30
tgcagaggcg gaaatga                                                    17

<210> SEQ ID NO 31
<211> LENGTH: 14
<212> TYPE: DNA
<213> ORGANISM: Artificial Sequence
<220> FEATURE:
<223> OTHER INFORMATION: Probe for PsAFB6 in qRT-PCR assay

<400> SEQUENCE: 31
ctgccccgac ttta                                                       14

<210> SEQ ID NO 32
<211> LENGTH: 20
<212> TYPE: DNA
```

```
<213> ORGANISM: Artificial Sequence
<220> FEATURE:
<223> OTHER INFORMATION: Forward primer for PsAFB2 (validation) in
      qRT-PCR assay

<400> SEQUENCE: 32
cagtagccaa gaactgtcca                                                  20

<210> SEQ ID NO 33
<211> LENGTH: 20
<212> TYPE: DNA
<213> ORGANISM: Artificial Sequence
<220> FEATURE:
<223> OTHER INFORMATION: Reverse primer for PsAFB2 (validation) in
      qRT-PCR assay

<400> SEQUENCE: 33
tcaactgacc ggagagtgat                                                  20

<210> SEQ ID NO 34
<211> LENGTH: 14
<212> TYPE: DNA
<213> ORGANISM: Artificial Sequence
<220> FEATURE:
<223> OTHER INFORMATION: Probe for PsAFB2 (validation) in qRT-PCR assay

<400> SEQUENCE: 34
tgcagccact ggat                                                        14

<210> SEQ ID NO 35
<211> LENGTH: 21
<212> TYPE: DNA
<213> ORGANISM: Artificial Sequence
<220> FEATURE:
<223> OTHER INFORMATION: Forward primer for PsAFB6 (validation) in
      qRT-PCR assay

<400> SEQUENCE: 35
gtcgtcaaat gaccaatgct g                                                21

<210> SEQ ID NO 36
<211> LENGTH: 22
<212> TYPE: DNA
<213> ORGANISM: Artificial Sequence
<220> FEATURE:
<223> OTHER INFORMATION: Reverse primer for PsAFB6 (validation) in
      qRT-PCR assay

<400> SEQUENCE: 36
gttcgtccgt caggtaatct tg                                               22

<210> SEQ ID NO 37
<211> LENGTH: 14
<212> TYPE: DNA
<213> ORGANISM: Artificial Sequence
<220> FEATURE:
<223> OTHER INFORMATION: Probe for PsAFB6 (validation) in qRT-PCR assay

<400> SEQUENCE: 37
ctgccccgac ttta                                                        14

<210> SEQ ID NO 38
<211> LENGTH: 20
<212> TYPE: DNA
<213> ORGANISM: Artificial Sequence
<220> FEATURE:
<223> OTHER INFORMATION: Forward primer for 18s rRNA in qRT-PCR assay
```

-continued

```
<400> SEQUENCE: 38
acgtccctgc cctttgtaca                                                    20

<210> SEQ ID NO 39
<211> LENGTH: 21
<212> TYPE: DNA
<213> ORGANISM: Artificial Sequence
<220> FEATURE:
<223> OTHER INFORMATION: Reverse primer for 18s rRNA in qRT-PCR assay

<400> SEQUENCE: 39
cacttcaccg gaccattcaa t                                                  21

<210> SEQ ID NO 40
<211> LENGTH: 20
<212> TYPE: DNA
<213> ORGANISM: Artificial Sequence
<220> FEATURE:
<223> OTHER INFORMATION: Probe for 18s rRNA in qRT-PCR assay

<400> SEQUENCE: 40
accgcccgtc gctcctaccg                                                    20
```

What is claimed is:

1. A polynucleotide construct comprising a polynucleotide encoding a polypeptide comprising an amino acid sequence selected from the group consisting of
    (a) an Auxin Signaling F-Box Protein 6 (AFB6) sequence having the amino acid sequence set forth in SEQ ID NO: 4 and (b) an Auxin Signaling F-Box Protein 2 (AFB2) sequence having the amino acid sequence set forth in SEQ ID NO: 2, wherein said polynucleotide is operably linked to a heterologous inducible promoter.

2. A vector comprising (i) a polynucleotide encoding a polypeptide comprising an amino acid sequence selected from the group consisting of (a) an AFB6 sequence having the amino acid sequence set forth in SEQ ID NO: 4 and (b) an AFB2 sequence having the amino acid sequence set forth in SEQ ID NO: 2, wherein said polynucleotide is in sense or antisense orientation, and (ii) a selectable marker.

3. A transgenic plant from the Fabaceae plant family, or any part thereof, comprising the polynucleotide construct according to claim 1.

4. The plant or any part thereof of claim 3, wherein said part is selected from the group consisting of a plant cell, plant seed, callus, plant embryo, microspore-derived embryo, and microspore.

5. The plant or any part thereof of claim 3, wherein the plant is a pea or soybean plant.

* * * * *